(12) United States Patent
Guibourt et al.

(10) Patent No.: US 8,993,808 B2
(45) Date of Patent: Mar. 31, 2015

(54) PHENYLCYCLOPROPYLAMINE DERIVATIVES AND THEIR MEDICAL USE

(75) Inventors: Nathalie Guibourt, Barcelona (ES); Alberto Ortega Munoz, Barcelona (ES); Julio Castro-Palomino Laria, Barcelona (ES)

(73) Assignee: Oryzon Genomics, S.A., Barcelona (ES)

( * ) Notice: Subject to any disclaimer, the term of this patent is extended or adjusted under 35 U.S.C. 154(b) by 275 days.

(21) Appl. No.: 13/138,143

(22) PCT Filed: Jan. 21, 2010

(86) PCT No.: PCT/EP2010/050697
§ 371 (c)(1),
(2), (4) Date: Sep. 12, 2011

(87) PCT Pub. No.: WO2010/084160
PCT Pub. Date: Jul. 29, 2010

(65) Prior Publication Data
US 2012/0004262 A1   Jan. 5, 2012

(30) Foreign Application Priority Data
Jan. 21, 2009   (EP) .................................. 09000790

(51) Int. Cl.
| C07C 211/40 | (2006.01) |
| C07D 213/38 | (2006.01) |
| C07C 217/58 | (2006.01) |
| C07C 217/74 | (2006.01) |
| C07C 255/58 | (2006.01) |
| C07D 213/61 | (2006.01) |
| C07D 277/28 | (2006.01) |
| C07D 333/20 | (2006.01) |
| C07D 333/28 | (2006.01) |

(52) U.S. Cl.
CPC ............ *C07D 213/38* (2013.01); *C07C 211/40* (2013.01); *C07C 217/58* (2013.01); *C07C 217/74* (2013.01); *C07C 255/58* (2013.01); *C07D 213/61* (2013.01); *C07D 277/28* (2013.01); *C07D 333/20* (2013.01); *C07D 333/28* (2013.01); *C07C 2101/02* (2013.01)
USPC .......................................... 564/384; 514/311

(58) Field of Classification Search
None
See application file for complete search history.

(56) References Cited

U.S. PATENT DOCUMENTS

| 3,106,578 | A | 10/1963 | Kaiser et al. |
| 3,365,458 | A | 1/1968 | Biel et al. |
| 3,471,522 | A | 10/1969 | Biel et al. |
| 3,532,712 | A | 10/1970 | Biel et al. |
| 3,532,749 | A | 10/1970 | Biel et al. |
| 3,758,684 | A | 9/1973 | Elion et al. |
| 4,409,243 | A | 10/1983 | Lieb |
| 4,522,811 | A | 6/1985 | Eppstein et al. |
| 4,530,901 | A | 7/1985 | Weissmann |
| 6,043,393 | A | 3/2000 | de Meijere et al. |
| 6,211,244 | B1 | 4/2001 | Van Wagenen et al. |
| 6,337,074 | B1 | 1/2002 | Marsden et al. |
| 6,809,120 | B1 | 10/2004 | Warrington et al. |
| 6,897,216 | B2 * | 5/2005 | Neustadt et al. .............. 514/250 |
| 7,399,825 | B2 | 7/2008 | Lipps et al. |
| 7,611,704 | B2 | 11/2009 | Thorpe et al. |
| 7,628,993 | B2 | 12/2009 | Vilalta et al. |
| 7,799,782 | B2 | 9/2010 | Munson et al. |
| 2003/0008844 | A1 | 1/2003 | Spero et al. |
| 2003/0236225 | A1 | 12/2003 | Protopopova et al. |
| 2004/0019117 | A1 | 1/2004 | Protopopova et al. |
| 2004/0033986 | A1 | 2/2004 | Protopopova et al. |
| 2004/0048802 | A1 | 3/2004 | Ripka et al. |
| 2004/0062601 | A1 | 4/2004 | Thompson |
| 2004/0132820 | A1 | 7/2004 | Gosselin et al. |
| 2004/0147741 | A1 | 7/2004 | Sundermann et al. |
| 2004/0162287 | A1 | 8/2004 | Sundermann et al. |
| 2004/0176469 | A1 | 9/2004 | Thomas |
| 2004/0229872 | A1 | 11/2004 | Friderichs et al. |
| 2004/0254158 | A1 | 12/2004 | Qiao et al. |
| 2005/0009832 | A1 | 1/2005 | Sun et al. |
| 2005/0154056 | A1 | 7/2005 | Yang et al. |
| 2005/0277662 | A1 * | 12/2005 | Dress et al. ................... 514/300 |
| 2006/0087206 | A1 | 4/2006 | Yamada |
| 2006/0116370 | A1 | 6/2006 | Dollinger et al. |
| 2006/0148904 | A1 | 7/2006 | Protopopova et al. |
| 2006/0211709 | A1 * | 9/2006 | Buhr et al. ............... 514/255.05 |
| 2006/0270673 | A1 * | 11/2006 | Duggan et al. ............. 514/235.2 |
| 2006/0275366 | A1 | 12/2006 | Malcolm et al. |
| 2006/0287287 | A1 | 12/2006 | Gerritz et al. |
| 2007/0025709 | A1 | 2/2007 | Gladnick et al. |

(Continued)

FOREIGN PATENT DOCUMENTS

| EP | 1 193 268 | 4/2002 |
| EP | 1704859 | 9/2006 |

(Continued)

OTHER PUBLICATIONS

PCT International Search Report, PCT/EP2010/050697, dated Mar. 19, 2010.
PCT International Search Report, PCT/EP2009/063685 dated Dec. 23, 2009.
"Histone Demethylation Mediated by the Nuclear Amine Oxidase Homolog LSD1" Y. Shi (2004) *Cell* 119, 941-953.
"Androgen receptor coactivators lysine-specific histone demethylase 1 and four and a half LIM domain protein 2 predict risk of prostate cancer recurrence." P. Kahl (2006) *Cancer Res.* 66(23), 11341-7.
"Role of the Lysine-Specific Demethylase 1 in the Proinflammatory Phenotype of Vascular Smooth Muscle Cells of Diabetic Mice" M. A. Reddy (2008) *Circ. Res.* 103, 615.

(Continued)

*Primary Examiner* — James D Anderson
(74) *Attorney, Agent, or Firm* — Finnegan, Henderson, Farabow, Garrett & Dunner

(57) ABSTRACT

The present invention relates to phenylcyclopropylamine derivatives. In particular, pharmaceutical compositions comprising phenylcyclopropylamine derivatives are provided. The compounds of this invention can, inter alia, be used for the treatment and the prevention of cancer as well as neurodegenerative diseases or disorders.

30 Claims, No Drawings

(56) References Cited

U.S. PATENT DOCUMENTS

| | | | |
|---|---|---|---|
| 2007/0213338 A1* | 9/2007 | Lebsack et al. | 514/252.05 |
| 2008/0139665 A1 | 6/2008 | Schuele et al. | |
| 2008/0242698 A1 | 10/2008 | Flor et al. | |
| 2008/0269228 A1 | 10/2008 | Moore et al. | |
| 2009/0203750 A1* | 8/2009 | Kozikowski et al. | 514/357 |
| 2009/0247530 A1 | 10/2009 | Nolte et al. | |
| 2010/0016262 A1 | 1/2010 | Mehai et al. | |
| 2010/0043721 A1 | 2/2010 | Cigan | |
| 2010/0240649 A1 | 9/2010 | Zhang | |
| 2010/0292225 A1 | 11/2010 | Chamoin et al. | |
| 2010/0324147 A1 | 12/2010 | McCafferty et al. | |
| 2012/0202810 A1 | 8/2012 | Nolte et al. | |
| 2013/0197095 A1 | 8/2013 | Nolte et al. | |

FOREIGN PATENT DOCUMENTS

| | | |
|---|---|---|
| EP | 1 741 708 | 1/2007 |
| EP | 2 233 495 | 9/2010 |
| GB | 1 307 341 | 2/1973 |
| JP | 2001-354563 | 12/2001 |
| NO | WO 2010/011845 | 1/2010 |
| SU | 230169 | 10/1968 |
| WO | WO 94/27947 | 12/1994 |
| WO | WO 96/38141 | 12/1996 |
| WO | WO 98/18459 | 5/1998 |
| WO | WO 99/05142 | 2/1999 |
| WO | WO 99/05143 | 2/1999 |
| WO | WO 99/31072 | 6/1999 |
| WO | WO 99/54440 | 10/1999 |
| WO | WO 99/67203 | 12/1999 |
| WO | WO 00/34283 | 6/2000 |
| WO | WO 01/92264 | 12/2001 |
| WO | WO 02/079152 | 10/2002 |
| WO | WO 03/087064 | 10/2003 |
| WO | WO 03/093297 | 11/2003 |
| WO | WO 03/096989 | 11/2003 |
| WO | WO 2004/020415 | 3/2004 |
| WO | WO 2004/055010 | 7/2004 |
| WO | WO2004062601 | 7/2004 |
| WO | WO 2004/065367 | 8/2004 |
| WO | WO 2004/072086 | 8/2004 |
| WO | WO 2005/009941 | 2/2005 |
| WO | WO 2005/023761 | 3/2005 |
| WO | WO2005/025558 A1 | 3/2005 |
| WO | WO 2005/037843 | 4/2005 |
| WO | WO 2005/058808 | 6/2005 |
| WO | WO 2005/058883 | 6/2005 |
| WO | WO 2005/058884 | 6/2005 |
| WO | WO 2005/103003 | 11/2005 |
| WO | WO 2006/071608 | 7/2006 |
| WO | WO2006087206 | 8/2006 |
| WO | WO 2007/000248 | 1/2007 |
| WO | WO2007005896 | 1/2007 |
| WO | WO 2007/015824 | 2/2007 |
| WO | WO 2007/025144 | 3/2007 |
| WO | WO2007025709 | 3/2007 |
| WO | WO 2007/021839 | 7/2007 |
| WO | WO 2007/106016 | 9/2007 |
| WO | WO 2007/134799 | 11/2007 |
| WO | WO 2008/033466 | 3/2008 |
| WO | WO 2008/116156 | 9/2008 |
| WO | WO 2008/127734 | 10/2008 |
| WO | WO 2009/001132 | 12/2008 |
| WO | WO 2009/023179 | 2/2009 |
| WO | WO 2009/039134 | 3/2009 |
| WO | WO 2009/052078 | 4/2009 |
| WO | WO 2009/097278 | 8/2009 |
| WO | WO 2009/109991 | 9/2009 |
| WO | WO 2009/117515 | 9/2009 |
| WO | WO 2009/145856 | 12/2009 |
| WO | WO 2009/153197 | 12/2009 |
| WO | WO 2010/014921 | 2/2010 |
| WO | WO 2010/030592 | 3/2010 |
| WO | WO2010043721 | 4/2010 |
| WO | WO 2010/084160 | 7/2010 |
| WO | WO 2010/085749 | 7/2010 |
| WO | WO 2010/099527 | 9/2010 |
| WO | WO/2010/139784 | 12/2010 |
| WO | WO2010/143582 | 12/2010 |
| WO | WO 2011/022489 | 2/2011 |
| WO | WO 2011/031934 | 3/2011 |
| WO | WO 2011/035941 | 3/2011 |
| WO | WO 2011/042217 | 4/2011 |
| WO | WO 2011/057262 | 5/2011 |
| WO | WO 2011/106105 | 9/2011 |
| WO | WO 2011/106106 | 9/2011 |
| WO | WO 2011/113005 | 9/2011 |
| WO | WO 2011/131576 | 10/2011 |
| WO | WO 2011/131697 | 10/2011 |
| WO | WO 2011/132083 | 10/2011 |
| WO | WO 2012/001531 | 1/2012 |
| WO | WO 2012/013727 | 2/2012 |
| WO | WO 2012/013728 | 2/2012 |
| WO | WO 2012/034116 | 3/2012 |
| WO | WO 2012/042042 | 4/2012 |
| WO | WO 2012/045883 | 4/2012 |
| WO | WO 2012/072713 | 6/2012 |
| WO | WO 2012/107498 | 8/2012 |
| WO | WO 2012/107499 | 8/2012 |
| WO | WO 2012/135113 | 10/2012 |
| WO | WO 2012/156531 | 11/2012 |
| WO | WO 2012/156537 | 11/2012 |
| WO | WO 2013/057320 | 4/2013 |
| WO | WO 2013/057322 | 4/2013 |

OTHER PUBLICATIONS

"Histone H3 lysine 4 demethylation is a target of nonselective antidepressive medications". M. G. Lee (2006) Chem. Biol. 13(6), 563-7.

"trans-2-Phenylcyclopropylamine Is a Mechanism-Based Inactivator of the Histone Demethylase LSD1" D.M.Z. Schmidt (2007) Biochemistry 46 (14), 4408-4416.

"Facile synthesis of substituted trans-2-arylcyclopropylamine inhibitors of the human histone demethylase LSD1 and monoamine oxidases A and B". D.M. Gooden (2008) Bioorg Med Chem Lett. 18, 3047-51.

"Inhibition of lysine-specific demethylase 1 by polyamine analogues results in reexpression of aberrantly silenced genes" Y. Huang (2007) PNAS 104 (19), 8023-8028.

"Inhibition of cell growth by EGR-1 in human primary cultures from malignant glioma" A. Calogero (2004) Cancer Cell Int. 4.

"Sustained Expression of Early Growth Response Protein-1 Blocks Angiogenesis and Tumor Growth" M. Lucerna (2006) Cancer Res. 66, 6708-6713.

"EGR1 Predicts PTEN and Survival in Patients With Non-Small-Cell Lung Cancer" B. Ferraro (2005) J. Clin. Oncol 23(9), 1921-1926.

"The lysine-specific demethylase 1 is required for cell proliferation in both p53-dependent and -independent manners". A. Scoumanne (2007) J. Biol. Chem. 282, 15471-15475.

"Mutation of Drosophila LSD1 disrupts H3-K4 methylation, resulting in tissue-specific defects during development". L. Di Stefano (2007) Curr Biol. 17(9), 808-12.

"LSD1 demethylates repressive histone marks to promote androgen-receptor-dependent transcription". E. Metzger (2005) Nature 437, 436-9.

"2-Substituted Cyclopropylamines. I. Derivatives and Analogs of 2-Phenylcyclopropylamine" Kaiser (1962) J. Med. Chem. 5 (6), 1243-1265.

"2-Substituted cyclopropylamines. II. Effects of structure upon monoamine oxidase-inhibitory activity as measured in vivo by potentiation of tryptamine convulsions." Zirkle (1962) J. Med. Chem. 5(6), 1265-1284.

"Fluorinated phenylcyclopropylamines. Part 3: Inhibition of monoamine oxidase A and B." S. Yoshida (2004) Bioorg. Med. Chem. 12(10), 2645-2652.

"Fluorinated phenylcyclopropylamines. Part 5: Effects of electron-withdrawing or -donating aryl substituents on the inhibition of monoamine oxidases A and B by 2-aryl-2-fluoro-cyclopropylamines" S. Hruschkaa (2008) Bioorg. Med. Chem. 16(15), 7148-7166.

(56) References Cited

OTHER PUBLICATIONS

"Monoamine oxidase inhibitors: reappraisal of dietary considerations". D. G. Folks (1983) *J. Clin.Psychopharmacol.* Abstract, 3(4), 249-52.
"Protein methylation: a new mechanism of p53 tumor suppressor regulation" A. Scoumanne (2008) *Histol Histopathol* 23, 1143-1149.
"Structural Basis for the Inhibition of the LSD1 Histone Demethylase by the Antidepressant trans-2-Phenylcyclopropylamine" M. Yang (2007) *Biochemistry* 46 (27), 8058-8065.
"Crystal structure of histone demethylase LSD1 and tranylcypromine at 2.25 Å" S. Mimasu (2008) *Biochemical and Biophysical Research Communications* 366, 15-22.
"Structural basis of histone demethylation by LSD1 revealed by suicide inactivation" M. Yang (2007) *Nature Structural & Molecular Biology* 14(6), 535-539.
"The lysine demethylase LSD1 (KDM1) is required for maintenance of global DNA methylation" J. Wang (2009) *Nature Genetics* 41(1), 125-129.
"LSD1: oxidative chemistry for multifaceted functions in chromatin Regulation." F. Forneris (2008) *Trends in Biochemical Sciences* 33(4), 181-189.
"Synthesis, Stereochemical Identification, and Selective Inhibitory Activity against Human Monoamine Oxidase-B of 2-Methylcyclohexylidene-(4-arylthiazol-2-yl)hydrazones". Franco Chimenti (2008) *J. Med. Chem.* 51 (16), 4874-4880.
"Lysine-Specific Demethylase I is strongly expressed in poorly differentiated neuroblastoma: implications for therapy". J.H Schulte (2009) *Cancer Res.* 69 (5), 2065-2071.
"Synthesis and structure-activity relationship of 4-(2-arylcyclopropylamino)-quinoline-3-carbonitriles as EGFR tyrosine kinase inhibitors". M. Pannala (2007) *Bioorganic & Medicinal Chemistry Letters* 17 (21), 5978-5082.
"Mechanisms involved in the regulation of histone lysine demethylases". F. Lan, 2008 *Current Opinion in Cell Biology*, 20 316-325.
"Histone demethylase LSD1 is required to induce skeletal muscle differentiation by regulating myogenic factors" J. Choi (2010) *Biochemical and Biophysical Research Communications* 401(3), 327-332.
"Cancer Therapy: Preclinical Novel Oligoamine Analogues Inhibit Lysine-Specific Demethylase 1 and Induce Reexpression of Epigenetically Silenced Genes" Y. Huang (2009) *Clin. Cancer Res.* 15(23), 7217-28.
"Structurally designed trans-2-phenylcyclopropylamine derivatives potently inhibit histone demethylase LSD1/KDM1". S. Mimasu (2010) *Biochemistry* 49 (30), 6494-503.
"Biochemical, Structural, and Biological Evaluation of Tranylcypromine Derivatives as Inhibitors of Histone Demethylases LSD1 and LSD2". C. Binda (2010) *JACS* 132, 6827-6833.
"LSD1 Is a Subunit of the NuRD Complex and Targets the Metastasis Programs in Breast Cancer" Y. Wang (2009) *Cell* 138, 660-672.
"(Bis)urea and (Bis)thiourea Inhibitors of Lysine-Specific Demethylase 1 as Epigenetic Modulators" S. K. Sharma (2010) *J. Med. Chem.* 53 (14), 5197-5212.
"Identification of Cell-Active Lysine Specific Demethylase 1-Selective Inhibitors" R. Ueda (2009) *J. Am. Chem Soc* 131(48), 17536-17537.
"N-Substituted derivatives of 2-aminoethanethiol and 2-hydrazinoethanethiol" R.D. Westland 1968 *J Med Chem* 11(4) 824-829.
"Lysine-specific demethylase 1 (LSD1) is highly expressed in ER-negative breast cancers and a biomarker predicting aggressive biology" LIM 2010 *Carcinogenesis* 31(3) 512-520.
"Modulation of breast cancer resistance protein (BCRP/ABCG2) by non-basic chalcone analogues" Han 2008 *Eur. J. Pharma.* 35(1-2) 30-41.
"Combinatorial lead optimization of [1,2]-diamines based on ethambutol as potential antituberculosis preclinical candidates" Abstract, R. E. Lee (2003) *J. Comb. Chem.* 5(2), 172-187.

English language abstract of JP 2001-354563, Dec. 25, 2001.
English translation of Russian Patent No. SU 230169, dated Oct. 30, 1968.
International Search Report of PCT/EP2010/050697, Mar. 19, 2010.
XP-002568777, Aurora Screen Library, Aug. 20, 2009.
Co-pending U.S. Appl. No. 13/497,994, filed Mar. 31, 2011.
Co-pending U.S. Appl. No. 13/066,616, filed Apr. 18, 2011.
Co-pending U.S. Appl. No. 13/641,916, filed Oct. 27, 2011.
Co-pending U.S. Appl. No. 13/812,366, filed Feb. 2, 2012.
Co-pending U.S. Appl. No. 13/500,687, filed Jul. 2, 2012.
Co-pending U.S. Appl. No. 13/580,710, filed Jan. 4, 2013.
Co-pending U.S. Appl. No. 13/580,553, filed Jan. 4, 2013.
Co-pending U.S. Appl. No. 13/876,485, national stage entry Mar. 28, 2013.
Co-pending U.S. Appl. No. 13/990,182, national stage entry Mar. 29, 2013.
Co-pending U.S. Appl. No. 13/812,386, filed Apr. 4, 2013.
Co-pending U.S. Appl. No. 13/877,919, national stage entry Apr. 16, 2013.
Ahmed Khaleel et al., "Ticagrelor: A New Reversible Oral Antiplatelet Agent," International Research Journal of Pharmacy, 1(1), pp. 62-69, 2010.
Y.P. Arya et al., "Syntehsis of 5H-Dibenzo[1,d]cycloheptene Derivatives with Diverse Biological Activities," Indian Journal of Chemistry vol. 16B, pp. 220-235, 1978.
Orit Bar-Am et al., "Regulation of Bcl-2 family proteins, neurotrophic factors, and APP processing in the neurorescue activity of propargylamine," The FASEB Journal, 19(13), pp. 1899-1901, 2005.
Fabrice Barlési et al, "Global Histone Modifications Predict Prognosis of Resected Non-Small-Cell Lung Cancer," Journal of Clinical Oncology, vol. 25, No. 28, pp. 4358-4364, 2007.
Hanae Benelkebir et al., "Enantioselective synthesis of tranylcypromine analogues as lysine demethylase (LSD1) Inhibitors," Bioorganic & Medicinal Chemistry, vol. 19, pp. 3709-3716, 2011.
Vanja Radisic Biljak, "Platelet cunt, mean platelet volume and smoking status in stable chronic obstructive pulmonary disease," Platelets, 22(6), pp. 468-470, 2011.
Allessandra Bisi et al., "Multidrug resistance reverting activity and antitumor profile of new phenothiazine derivatives," Bioorganic & medicinal Chemistry, vol. 16. pp. 6474-6482, 2008.
Eric Bollard et al., "Platelets Amplify Inflammation in Arthritis via Collagen-Dependent Microparticle Production," Science, 327(5965), pp. 580-583, 2010.
I.G. Bolesov et al, "Cyclopropanes and Cyclobutanes," J. Organic Chem USSR, 10(6), pp. 1678-1684, 1974.
Andrea H. Brand, Targeted gene expression as a means of altering cell fates and generating dominant phenotypes, Development, 118, pp. 401-419, 1993.
Lena Brydon et al, "Platelets, coronary heart disease, and stress," Brain, Behavior, and Immunity, 20, pp. 113-119, 2006.
E.A. Burakova et al., "N- and O-Alkylation of 3-indolylcyclopropylacetic acid derivatives," Russian Chemical Bulletin, International Edition, vol. 51, No. 10. po. 1829-1840, 2002.
K. Burk et al, "Cognitive deficits in spinocerebellar ataxia 2," Brain, 122, pp. 769-777, 1999.
Gulfidan Cakmak M al., "Platelets: Indicator of inflammation in COPD," International Journal of Medicine and Medical Sciences, vol. 1(5), pp. 227-229, 2009.
Robert A. Casero Jr., "Recent Advances in the Development of Polyamine Analogues as Antitumor Agents," J. Med. Chem., 52, pp. 455-4573, 2009.
Liang Kung Chen et al, "Association of Insulin Resistance and Hematologic Parameters: Study of a Middle-aged and Elderly Chinese Population in Taiwan," J. Chin. Med. Accoc., vol. 69, No. 6, pp. 248-253, 2006.
Q.L. Choo et al., "Genetic organization and diversity of the hepatitis C. virus," Proc. Natl. Acad. Sci, USA, vol. 88, pp. 2451-2455, 1991.
Jeffrey C. Culhane et al., "A Mechanism-Based Inactivator for Histone Demethylase LSD1,"J. Am. Chem. Soc, 128, pp. 4536-4537, 2006.

(56) References Cited

OTHER PUBLICATIONS

Jeffrey C. Culhane et al., "Comparative Analysis of Small Molecules and Histone Substrate Analogues as LSD1 Lysine Demethylase Inhibitors," J Am. Chem, Soc., 132(9), pp. 3164-3176, 2010.

Silvio Danese, MD, et al., "Platelets in Inflammatory Bowel Disease: Clinical, Pathogenic, and Therapeutic Implications" American Journal of Gastroenterology 99(5). pp. 938-945, 2004.

Stephen P. East et al., "An orally bioavailable positive allosteric modulator of the mGlu$_4$ receptor with efficacy in an animal model of motor dysfunction," Bioorganic 7 Medicinal Chemistry letters, 20. pp. 4901-4905, 2010.

Michael C. Ellis, et al., "Expression of *Drosophilia* glass protein and evidence for negative regulation of its activity in non-neuronal cells by another DNA-binding protein,"Development, 119, pp. 855-865, 1993.

Somaia E. Elsheikh, et al., "Global Histone Modifications in Breast Cancer Correlate with Tumor Phenotypes, Prognostic Factors, and Patients Outcome,"Cancer Research, 69, pp. 3802-3809, 2009.

Angela Erazo et al, "Varicella-Zoster Virus Open reading Frame 66 Protein Kinase Is Required for Efficient Viral Growth in Primary Human Corneal Stromal Fibroblast Celts," Journal of Virology, pp. 7653-7665, 2008.

Catherine A Faler et al., "The Kulinkovich Reaction in the Synthesis of Constrained N,N-Dialkyl Neurotransmitter Analogues," Organic Letters, vol. 9, No. 10, 2007, 1987-1990.

J. Ferlay et al., "Estimates of the Cancer Incidence and Mortality in Europe in 2006," Annals of Oncology, 18, pp. 581-592, 2007.

Andre Fischer, "Recovery of learning and memory is associated with chromatin remodeling," Nature, Vo. 447(1), pp. 178-182, 2007.

Meinrad Gawaz et al., "Platelets in inflammation and atherogenesis," The Journal of Clinical Investigation, vol. 155, No. 12, pp. 3378-3384, 2005.

Young Su Han et al., "Antidepressants reveal differential effect against 1-methyl-4-phenylpyridinium toxicity in differentiated PC12 cells," Eur. J. Pharmacol., 604,(1-3), pp. 36-44, 2008.

Shinya Hayami et al, "Overexpression of LSD1 contributes to human carcinogensis through chromatin regulation in various cancers," J. Cancer, 128(3), pp. 574-586, 2011.

Jing Huang et al, "p53 is regulated by the lysine demethylase LSD1," Nature, 449, pp. 105-108, 2007.

George R. Jackson, et al., "Polyglutamine-Expanded Human Huntingtin Transgenes Induce Degeneration of *Drosophila* Photoreceptor Neurons," Neuron., vol. 21, pp. 633-642, 1998.

Rainer Kiefmann et al, "Red blood cells induce hypoxic lung inflammation," Blood 111(10); pp. 5205-5214, 2008.

K.N. Kornerup et al, "The role of platelets in the pathophysiology of asthma," Platelets, 18(5), pp. 319-328, 2007.

Nicole Krieger et al., "Enhancement of hepatitis C Virus RNA Replication by Cell Culture-Adaptive Mutations," Journal of Virology, 75(10), pp. 4614-4624, 2001.

Richard E. Lee et al., "Combinatorial Lead Optimization of [1,2]-Diamines Based Ethambutol as Potential Antituberculosis Preclinical Candidates," J. Comb. Chem, 5, pp. 172-187, 2003.

Dong-bao Li et al., "Association between inflammatory mediators and angiographic morphologic features indicating thrombus formation in patients with acute myocardial infarction," Chin. Med. J., 122(15), pp. 1736-1742, 2009.

Yu Liang et al., "Inhibition of the histone demethylase LSD1 blocks α-herpesvirus lytic replication and reactivation from latency," Nat. Med., 15(11), 1212-1317, 2009.

Anca Roxana Lupu, Md, Ph.D., "Up-to-date in the hematological malignancies treatment," Medica, A Journal of Clinical Medicine, vol. 1, No. 1, pp, 63-65, 2006.

John D. Maclay et al, "Increased platelet activation in patients with stable and acute exacerbation of COPD," Thorax, 66, pp, 769-774, 2011.

P.F. Mannalonic et al. "Platelets and inflammation: Role of platelet-derived growth factor, adhesion molecules and histamine," Inflamm. Res. 46, pp. 4-18, 1997.

Archibald McNicol et al., "Beyond Hemostais: The Role of Platelets in Inflammation, Malignancy and Infection," Cariovascular & Haematological Disorders-Drug Targets, 8, pp. 99-117, 2008.

Nicholas A. Meanwell, Synopsis of Some Recent Tactical Application of Bioisosteres in Drug Design, Journal of Medicinal Chemistry, 54(8), pp. 2529-2591, 2011.

Chie Moritani et al., "Activation of Platelets in Bronchial Asthma,"Chest, 113, pp. 452-458, 1998.

Ramesh Neelamegam et al, "Brain-Penetrant LSD1 Inhibitors Can Block Memory Consolidation,"ACS Chemical Neuroscience, 3(2), pp. 120-128, 2012.

Daisuke Ogasawara et al., "Synthesis and biological activity of optically active NCL-1, a lysine-specific demethylase 1 selective inhibitor," Bioorganic & Medicinal Chemistry, doi:10.1016, 2010.

Brian P. O'Sullivan et al., "The Inflammatory Role of Platelets in Cystic Fibrosis,"Am. J. Respir. Crit. Care Med., 173, pp. 483-490, 2006.

Simon C. Pitchford et al, "Platelet P-selectin is required for pulmonary eosinophil and lymphocyte recruitment in a murine model of allergic inflammation," Blood, 105, pp. 2074-2081, 2005.

Julie A. Pollock et al, "Lysine-Specific Histone Demethylase 1 Inhibitors Control Breast Cancer Proliferation in Erα-Dependent and -Independent Manners," ACS Chem Biol., 7, pp. 1221-1231, 2012.

Bernard Ravine, MD, MSCE et al, "The Relationship Between CAG Repeat Length and Clinical Progression in Huntington's Disease," Movement Disorders, vol. 23, No. 9, pp. 1223-1227, 2008.

Thomas N. Riley et al., "Absolute Configuration of (+)- and (−)-trans-2-Phenylcyclopropylamine Hydrochloride", Journal of Medicinal Chemistry, vol. 15, No 11, pp. 1187-1188, 1972.

Henry M. Rinder et al. "Correlation of Thrombosis With Increased Platelet Turnover in Thrombocytosis,"Blood, 91. pp. 1288-1294, 1998.

David B. Seligson et al, "Global histone modification patterns predict risk of prostate cancer recurrence," Nature, vol. 435, No. 30, 2005.

David M. Seligson et al, "Global Levels of Histone Modifications Predict Prognosis in Different Cancers," The American Journal of Pathology, vol. 174, No. 5, 2009.

Philip J. Stephens, "The Determination of the Absolute Configurations of Chiral Molecules Using Vibrational Circular Dichroism (VOD) Spectroscopy,"Chirality, 20(5), pp. 643-663, 2008.

Nadine Stoffel et al., "Leukocyte count and risk of thrombosis in patients undergoing haematopoietic stem cell transplantation or intensive chemotherapy," Thrombosis and Haemostasis, 103)6), pp. 1228-1232, 2010.

Bernd Stratmann et al., "Pathobiology and cell interations of platelets in diabetes," Diabetes and Vascular Disease Research, 2(1), pp. 16-23, 2005.

Lawrence M. Szewczuk et al., "Mechanistic Analysis of a Suicide Inactivator of Histone Demethylase LSD1," Biochemistry, 46, pp. 6892-6902, 2007.

Risa Tamagawa-Mineoka et al, "Elevated Platelet Activation in Patients with Atopic Dermatitis and Psoriasis: Increased Plasma Levels of β-Thromboglobulin and Platelet Factor 4," Allergology International, 57, pp. 391-396, 2008.

Shannon L. Taylor et al.. "Roscovitine, a cyclin-Dependent Kinase Inhibitor, Prevents Replication of Varicella-Zoster Virus," Journal of Virology, vol. 78, No, 6, pp. 2853-2862, 2004.

E. Thaulow et al., "Blood platelet count and function are related to total and cardiovascular death in apparently healthy men," Circulation, 84, pp. 613-617, 1991.

Denisa D. Wagner et al., "Platelets in Inflammation and Thrombosis," Arteriosclerosis, Thrombosis and Vascular Biology, 23, pp. 2131-2137, 2003.

Orly Weinreb et al., "Novel Neuroprotective Mechanism of Action of Rasagiline Is Associated with Its Propargyl Moiety: Interation of Bel-2 Family members with PKC Pathway," Ann NY Acad Sci., 1053, pp. 346-355, 2005.

Camille G. Wermuth, "Molecular Variations Based on Isosteric Replacements," The Practice of Medicinal Chemisty ($2^{nd}$ edition), Academic Press, London, pp. 189-214, 2003.

Zackary W. Whitlow et al, "Recruitment of the Transcriptional Coactivator HCF-1 to Viral Immediate-Early Promoters During

(56) References Cited

OTHER PUBLICATIONS

Initiaion of Reactivation from latency of Herpes Simplex Virus Type 1," Journal of Virology, vol. 83, No. 18, pp. 9591-9595, 2009.
Scott Willoughby et al, "Platelets and cardiovascular disease," Eur. Journal of Cardiovascular Nursing, pp. 273-288, 2002.
M. Nabil Aboul-Enein et al, "Synthesis of some 4-substituted amino-1-methylpiperidines structurally related to antihistaminics", Pharmaceutica Acta Helvetiae, 1973, 48(3): 151-156.
O. Kinzel et al, "Identification of MK-5710 ((8aS)-8a-methyl-1,3-dioxo-2-[(1S,2R)-2-phenylcyclopropyl]-N-(1-phenyl-1H-pyrazol-5-yl)hexahydro-imidazo[1,5-a]pyrazine-7-(1H)-carboxamide), a potent smoothened antagonist for use in Hedgehog pathway dependent malignancies: Part 2", Bioorg Med Chem Lett 2011, 21(15), 4429-4435.
J Kim et al, "Flavin chemical models for monoamine oxidase inactivation by cyclopropylamines, α-silylamines, and hydrazines", J Am Chem Soc 1995, 117, 100-105.
Co-pending U.S. Appl. No. 13/983,840, national stage entry Aug. 6, 2013.
Co-pending U.S. Appl. No. 13/983,844, national stage entry Aug. 6, 2013.
Co-pending U.S. Appl. No. 14/118,323, national stage entry Nov. 18, 2013.
Co-pending U.S. Appl. No. 14/118,330, national stage entry Nov. 18, 2013.
Co-pending U.S. Appl. No. 14/096,557, filed Dec. 4, 2013.
I.G. Bolesov et al., "Cyclopropanes and Cyclobutanes, LXIX, Synthesis and Properties of (β-hydroxyalkylamino)cyclopropanes," Translated from Zhurnal Organicheskoi Khimii 10(10), 2122-2128 (1974).
Y. Shi, "Histone lysine demethylases: emerging roles in development, physiology and disease," Nature Reviews|Genetics, vol. 8, pp. 829-833 (2007).
J. Vagner et al., "Peptidomimetics, a synthetic tool of drug discovery," Current Opinion in Chemical Biology, vol. 12, pp. 292-296 (2008).

Cancer definition—MedicineNet.com, Medical References for Patients, p. 1 (2005).
CAPLUS, Document No. 157:576967, "Preparation of Cyclopropylamines as LSD1 inhibitors in the treatment of cancer," 2012.
HCAPLUS, Document No. 132:49802, "Preparation of 1-(N-subsituted aminomethyl)-4-quanidinomethyicyclohexanes useful in pain management," 1999.
CAS Registry No. RN903487-42-3, entered STN Aug. 23, 2006.
CAS Registry No. RN1251130-23-0, entered STN Nov. 3, 2010.
CAS Registry No. RN1281596-19-7, entered STN Apr. 17, 2011.
CAS Registry No. RN1281615-78-8, entered STN Apr. 17, 2011.
CAS Registry No. RN1282425-35-7, entered STN Apr. 19, 2011.
CAS Registry No. RN220351-33-7, entered STN Mar. 11, 1999.
CAS Registry No. RN844655-03-4, entered STN Mar. 9, 2005.
CAS Registry No. RN846596-02-9, entered STN Mar. 22, 2005.
CAS Registry No. RN848204-13-7, entered STN Apr. 11, 2005.
CAS Registry No. RN848732-87-6, entered STN Apr. 19, 2005.
CAS Registry No. RN848742-47-2, entered STN Apr. 19, 2005.
CAS Registry No. RN848753-47-9, entered STN Apr. 19, 2005.
CAS Registry No. RN918305-55-2, entered STN Jan. 24, 2007.
CAS Registry No. RN959071-98-8, entered STN Dec. 20, 2007.
CAS Registry No. RN1026299-47-7, entered STN Jun. 8, 2008.
CAS Registry No. RN1157140-28-7, entered STN Jun. 14, 2009.
J. Wang et al, Novel histone demethylase LSD1 inhibitors selectivity target cancer cells with pluripotent stem cell properties, Cancer Research, 2001, 71(23):7238-49.
F Zaragoza Dörwald "Side reactions in Organic Synthesis: a guide to successful synthesis design" Wiley-VCH Verlag GmbH & Co, KGaA, Wilenheim, Chapter 1, 2005.
M Youdim et al, "Bifunctional drug derivatives of MAO-B inhibitor rasagiline and iron chelator VK-28 as a more effective approach to treatment of brain ageing and ageing neurodegenerative diseases", Mechanisms of Ageing and Development, 2005, 126: 317-326.

\* cited by examiner

PHENYLCYCLOPROPYLAMINE DERIVATIVES AND THEIR MEDICAL USE

The present invention relates to phenylcyclopropylamine derivatives. In particular, pharmaceutical compositions comprising phenylcyclopropylamine derivatives are provided. The compounds of this invention can, inter alia, be used for the treatment and the prevention of cancer as well as neurodegenerative diseases or disorders.

Cancer is prevalent: there were about 3.2 million cancer cases diagnosed (53% men, 47% women) and 1.7 million deaths from cancer (56% men, 44% women) in Europe (Ferlay et al. (2007) Ann. Oncol. 18(3):581-92). In the United States, the probability of developing invasive cancer is 38% for females and 46% for males that live to be 70 years older and older. In the US about 1.4 million new cases of cancer are expected for 2006. Although the five year survival rate for cancer is now 65%, up from about 50% in the mid-nineteen seventies, cancer is deadly. It is estimated that 565,000 people in the United States will die from cancer in 2006 (American Cancer Society, Surveillance Research, 2006). Despite tremendous advances in cancer treatment and diagnosis, cancer remains a major public health concern. Accordingly, there is a need for new therapeutics with activity in cancer.

Another health crisis is facing industrialized nations. As the population in these countries age, neurodegenerative diseases are affecting more and more people, posing a tremendous economic burden to national health systems. Alzheimer's disease is the largest neurodegenerative disease; disease modifying drugs have long been sought, but to-date, none have been identified. Other neurodegenerative conditions include Parkinson's disease, Huntington's disease, Lewy Body dementia, and which are all characterized by disease progression which robs the patients of their ability to perform normal daily activities, eventually leading to death.

One similar characteristic amongst many cancers and neurodegenerative diseases is aberrant gene expression. A number of compounds have been shown to alter gene expression, including histone deacetylase inhibitors which alter the histone acetylation profile of chromatin. Histone deacetylase inhibitors have been shown to alter gene expression. Another modification that is involved in regulating gene expression is lysine methylation. Methylation of histone lysines has recently been shown to be important in regulating gene expression. A group of enzymes known as lysine demethylases are involved in this histone modification. One particular human histone lysine demethylase enzyme called Lysine Specific Demethylase-1 (LSD1) was recently discovered (Shi et al. (2004) Cell 119:941). LSD1 is also involved in regulating the methylation of some non-histone lysines. LSD1 has a fair degree of structural similarity, and amino acid identity/homology to monoamine oxidases, all of which (i.e., MAO-A, MAO-B and LSD1) are flavin dependent oxidases. Recent experiments with LSD1 have shown that it is involved in diverse process such as carcinogenesis (Kahl et al. (2006) Cancer Res. 66:1341-11347) and vascular inflammation (Reddy et al. (2008) Circ. Res. 103:615). It was found that a commercially available antidepressant, Parnate®, which targets monoamine oxidase (MAO), also inhibits LSD1 at clinically relevant concentrations (Lee et al. (2006) Chem. Biol. 13:563-567). Lee et al. initially reported that Parnate was a better inhibitor of LSD1 than either MAO-A and MAO-B but subsequent study by some of the same authors found "$IC_{50}$ values for 2-PCPA of 20.7±2.1 μM for LSD1, 2.3±0.2 μM for MAO A, and 0.95±0.07 μM for MAO B." See Schmidt et al. (2007) Biochemistry 46(14)4408-4416. Thus, Parnate (2-PCPA; tranylcypromine) is a better inhibitor of MAO-A and MAO-B as compared to LSD1. Monoamine oxidase inhibitors are useful for treating a number of conditions including depression and neurodegenerative conditions like Parkinson's disease. Parnate is part of a class of compounds known as phenylcyclopropylamines which are related to another group of clinical useful MAO inhibitors called propargylamines, exemplified by Pargyline which also inhibits LSD1. Additionally, derivatives of Parnate also can inhibit LSD1 (Gooden et al. (2008) Bioorg. Med. Chem. Let. 18:3047-3051). Another class of compounds was recently disclosed to inhibit LSD1 activity: polyamines (Huang et al. (2007) PNAS 104:8023-8028). The polyamines inhibit LSD1 modestly and were shown to cause the reexpression of genes aberrantly silenced in cancer cells.

Lee et al. ((2006) Chem. Biol. 13:563-567) reported that tranylcypromine inhibits histone H3K4 demethylation and can derepress Egr1 gene expression in some cancer lines. A body of evidence is accumulating that Egr-1 is a tumor suppressor gene in many contexts. Calogero et al ((2004) Cancer Cell International 4:1) reported that Egr-1 is downregulated in brain cancers and exogenous expression of Egr-1 resulted in growth arrest and eventual cell death in primary cancer cell lines. Lucerna et al. ((2006) Cancer Research 66, 6708-6713) showed that sustained expression of Egr-1 causes antiangiogenic effects and inhibits tumor growth in some models. Ferraro et al ((2005) J Clin Oncol. March 20; 23(9):1921-6) reported that Egr-1 is down-regulated in lung cancer patients with a higher risk of recurrence and may be more resistant to therapy. Scoumanne et al. ((2007) J Biol Chem. May 25; 282(21):15471-5) observed that LSD1 is required for cell proliferation. They found that deficiency in LSD1 leads to a partial cell cycle arrest in G2/M and sensitizes cells to growth suppression induced by DNA damage. Kahl et al ((2006) Cancer Res. 66(23):11341-7) found that LSD1 expression is correlated with prostate cancer aggressiveness. Metzger et al. ((2005) Nature 15; 437(7057):436-9) reported that LSD1 modulation by siRNA and pargyline regulates androgen receptor (AR) and may have therapeutic potential in cancers where AR plays a role, like prostate, testis, and brain cancers. Thus, a body of evidence has implicated LSD1 in a number of cancers, which suggests that LSD1 is a therapeutic target for cancer.

The phenylcyclopropylamines have been the subject of many studies designed to elucidate an SAR for MAO inhibition. Kaiser et al. ((1962) J. Med. Chem. 5:1243-1265) and Zirkle et al. ((1962) J. Med. Chem. 1265-1284) have disclosed the synthesis and activity of a number of phenylcyclopropylamine related compounds. Zirkle et al. ((1962) J. Med. Chem. 1265-1284) reported that mono- and disubstitution of the amino group of trans-2-phenylcyclopropylamine with methyl decreases the activity only slightly whereas monosubstitution with larger groups like alkyl and aralkyl groups results in considerable loss of activity in the tryptamine potentiation assay for MAO activity. Studies have also been conducted with phenylcyclopropylamine related compounds to determine selectivity for MAO-A versus MAO-B since MAO-A inhibitors can cause dangerous side-effects (see e.g., Yoshida et al. (2004) Bioorg. Med Chem. 12(10):2645-2652; Hruschka et al. (2008) Biorg Med Chem. (16):7148-7166; Folks et al. (1983) J. Clin. Psychopharmacol. (3)249; and Youdim et al. (1983) Mod. Probl. Pharmacopsychiatry (19): 63). Other phenylcyclopropylamine type compounds are disclosed in Bolesov et al ((1974) Zhurnal Organicheskoi Khimii 10:8 1661-1669) and Russian Patent No. 230169 (19681030). Gooden et al. ((2008) Bioorg. Med. Chem. Let. 18:3047-3051) describe the synthesis of phenylcyclopropylamine derivatives and analogs as well as their activity against MAO-A, MAO-B, and LSD1. None of the compounds made in Gooden et al. showed a lower Ki for LSD1 as compared to either MAO-A or MAO-B. Additionally, most of the Gooden et al. phenylcyclopropylamine derivatives were better inhibitors of MAO-A as compared to MAO-B. Recently, Han et al. (Euro. J. Pharma. (2008) doi:10.1016/j.ejphar.2008.12.025) reported that phenylcyclopropylamine displays neuroprotective activity in PC12 cells.

Phenylcyclopropylamine derivatives are also disclosed in U.S. Pat. No. 3,106,578, U.S. Pat. No. 6,211,244, US-A-2003/236225, WO 03/093297, WO 2007/025144, and in Westland R D, et al. J Med Chem. 1968. 11(4): 824-829.

In view of the lack of adequate treatments for conditions such as cancer and neurodegeneration, there is a desperate need for disease modifying drugs and drugs that work by inhibiting novel targets. There is a need for the development of LSD1 selective inhibitors particularly those which selectively inhibit LSD1 and those which are dual inhibitors of MAO-B/LSD1.

This problem is solved by the embodiments of the present invention as characterized herein below, in the appended examples and the claims.

The present invention relates to phenylcyclopropylamine derivatives. In particular, pharmaceutical compositions comprising phenylcyclopropylamine derivatives are provided. The compounds of this invention can, inter alia, be used for the treatment and the prevention of diseases. The present invention provides compounds of Formula I, pharmaceutical compositions comprising a compound of Formula I and a pharmaceutically acceptable carrier, and their use for treating and/or preventing diseases. One use of the compounds of Formula I is for treating cancer. Another use for the compounds of Formula I is to inhibit LSD1. Another use of the compounds of Formula I is as dual inhibitors of MAO-B and LSD1. Compounds of Formula I can have monoamine oxidase inhibition activity and therefore can be used to treat and/or prevent disease like depression and Parkinson's disease as well as other neurodegenerative conditions.

In one embodiment, the invention provides a pharmaceutical composition comprising a compound of Formula I and a pharmaceutically acceptable carrier:

FORMULA I

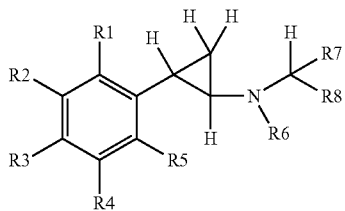

wherein
each of R1-R5 is independently chosen from —H, halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
R6 is chosen from —H and alkyl;
R7 is chosen from —H, alkyl, and cycloalkyl;

R8 is -L-heterocyclyl or -L-aryl, wherein the ring or ring system of said -L-heterocyclyl or -L-aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
each L is independently chosen from —$(CH_2)_n$—$(CH_2)_n$—, —$(CH_2)_n$NH$(CH_2)_n$—, —$(CH_2)_nO(CH_2)_n$—, and —$(CH_2)_nS(CH_2)_n$—, where each n is independently chosen from 0, 1, 2, and 3; and pharmaceutically acceptable salts thereof.

In one specific aspect of the pharmaceutical compositions of this embodiment, R8 is -L-heterocyclyl wherein said heterocyclyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In a more specific aspect, R8 is -L-heteroaryl wherein said heteroaryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In an even more specific aspect, R8 is heteroaryl (L is a bond) wherein said heteroaryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. Unless otherwise specified, according to the aspects described in this paragraph each L is independently chosen from —$(CH_2)_n$—$(CH_2)_n$—, —$(CH_2)_nNH(CH_2)_n$—, —$(CH_2)_nO(CH_2)_n$—, and —$(CH_2)_nS(CH_2)_n$—, and where each n is independently chosen from 0, 1, 2, and 3. In a more specific definition, L is independently chosen from —$(CH_2)_n$—$(CH_2)_n$— and —$(CH_2)_nO(CH_2)_n$—, where each n is independently chosen from 0, 1, 2, and 3. In a more specific definition, L is chosen from a covalent bond or —$CH_2$—. In a more specific definition, L is a covalent bond.

In one specific aspect of the pharmaceutical compositions of this embodiment, R8 is -L-aryl wherein said aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In a more specific aspect, R8 is aryl (L is a bond) wherein said aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In an even more specific aspect, R8 is a phenyl group wherein said phenyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. Unless otherwise specified, according to the aspects described in this paragraph each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3. In a more specific definition, L is independently chosen from —(CH$_2$)$_n$—(CH$_2$)$_n$— and —(CH$_2$)$_n$O(CH$_2$)$_n$—, where each n is independently chosen from 0, 1, 2, and 3. In a more specific definition, L is chosen from a covalent bond or —CH$_2$—. In a more specific definition, L is a covalent bond.

The invention provides a pharmaceutical composition comprising a pharmaceutically acceptable carrier and a compound of Formula I which is a selective inhibitor of LSD1. LSD1 selective inhibitors have IC50 values for LSD1 which are at least 2-fold lower than the IC50 value for MAO-A and/or MAO-B.

The invention also provides a pharmaceutical composition comprising a pharmaceutically acceptable carrier and a compound of Formula I which is a dual inhibitor selective for LSD1 and MAO-B. Dual LSD1/MAO-B selective inhibitors have IC50 values for LSD1 and MAO-B which are at least 2-fold lower than the IC50 value for MAO-A.

In one embodiment, the invention provides a compound of Formula I for treating and/or preventing cancer:

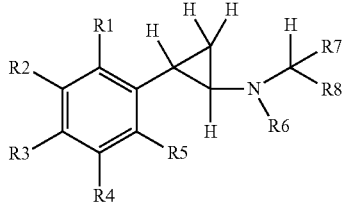

FORMULA I wherein
each of R1-R5 is independently chosen from —H, halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
R6 is chosen from —H and alkyl;
R7 is chosen from —H, alkyl, and cycloalkyl;
R8 is -L-heterocyclyl or -L-aryl, wherein the ring or ring system of said -L-heterocyclyl or -L-aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3; and pharmaceutically acceptable salts thereof.

In one specific aspect of this embodiment, the cancer is prostate cancer. In another specific aspect of this embodiment, the cancer is brain cancer. In yet another specific aspect of this embodiment, the cancer is breast cancer. In yet another specific aspect of this embodiment, the cancer is lung cancer. In yet another specific aspect of this embodiment, the cancer is testicular cancer. In yet another specific aspect of this embodiment, the cancer is colorectal cancer. In yet another specific aspect of this embodiment, the cancer is blood cancer (e.g., leukemia). In yet another specific aspect of this embodiment, the cancer is skin cancer.

In one specific aspect of this embodiment the invention provides a compound of Formula I for treating and/or preventing cancer where R8 is -L-heterocyclyl wherein said heterocyclyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In a more specific aspect of this embodiment the invention provides a compound of Formula I for treating and/or preventing cancer where R8 is -L-heteroaryl wherein said heteroaryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In an even more specific aspect of this embodiment the invention provides a compound of Formula I for treating and/or preventing cancer where R8 is heteroaryl (L is a bond) wherein said heteroaryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. Unless otherwise specified, according to the aspects described in this paragraph each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3. In a more specific definition, L is independently chosen from —(CH$_2$)$_n$—(CH$_2$)$_n$— and —(CH$_2$)$_n$O(CH$_2$)$_n$—, where each n is independently chosen from 0, 1, 2, and 3. In a more specific definition, L is chosen from a covalent bond or —CH$_2$—. In a more specific definition, L is a covalent bond.

In one specific aspect of this embodiment the invention provides a compound of Formula I for treating and/or preventing cancer where R8 is -L-aryl wherein said aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In a more specific aspect of this embodiment the invention provides a compound of Formula I for treating and/or preventing cancer where R8 is aryl (L is a bond) wherein said aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In an even more specific aspect of this embodiment the invention provides a compound of Formula I for treating and/or preventing cancer where R8 is a phenyl group wherein said phenyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. Unless otherwise specified, according to the aspects described in this paragraph each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3. In a more specific definition, L is independently chosen from —(CH$_2$)$_n$—(CH$_2$)$_n$—, and —(CH$_2$)$_n$O(CH$_2$)$_n$—, where each n is independently chosen from 0, 1, 2, and 3. In a more specific definition, L is chosen from a covalent bond or —CH$_2$—. In a more specific definition, L is a covalent bond.

In one embodiment, the invention provides a compound of Formula I for treating and/or preventing a neurodegenerative disease or disorder:

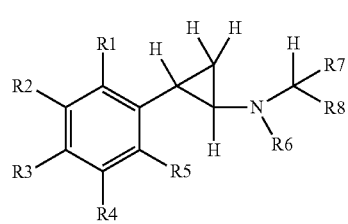

FORMULA I wherein
each of R1-R5 is independently chosen from —H, halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
R6 is chosen from —H and alkyl;
R7 is chosen from —H, alkyl, and cycloalkyl;
R8 is -L-heterocyclyl or -L-aryl, wherein the ring or ring system of said -L-heterocyclyl or -L-aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
each L is independently chosen from —(CH$_2$)$_n$—, —(CH$_2$)$_n$—, —(CH$_2$)$_n$NH(CH$_2$)$_n$—, —(CH$_2$)$_n$—O(CH$_2$)$_n$—, and —(CH$_2$)$_n$S(CH$_2$)$_n$—, where each n is independently chosen from 0, 1, 2, and 3; and pharmaceutically acceptable salts thereof.

In one specific aspect of this embodiment the invention provides a compound of Formula I for treating and/or preventing a neurodegenerative disease or disorder where R8 is -L-heterocyclyl wherein said heterocyclyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In a more specific aspect of this embodiment the invention provides a compound of Formula I for treating and/or preventing a neurodegenerative disease or disorder where R8 is -L-heteroaryl wherein said heteroaryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In an even more specific aspect of this embodiment the invention provides a compound of Formula I for treating and/or preventing a neurodegenerative disease or disorder where R8 is heteroaryl (L is a bond) wherein said heteroaryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. Unless otherwise specified, according to the aspects described in this paragraph each L is independently chosen from —(CH$_2$)$_n$— (CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3. In a more specific definition, L is independently chosen from —(CH$_2$)$_n$—(CH$_2$)$_n$— and —(CH$_2$)$_n$O(CH$_2$)$_n$—, where each n is independently chosen from 0, 1, 2, and 3. In a more specific definition, L is chosen from a covalent bond or —CH$_2$—. In a more specific definition, L is a covalent bond.

In one specific aspect of this embodiment the invention provides a compound of Formula I for treating and/or preventing a neurodegenerative disease or disorder where R8 is -L-aryl wherein said aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In a more specific aspect of this embodiment the invention provides a compound of Formula I for treating and/or preventing a neurodegenerative disease or disorder where R8 is aryl (L is a bond) wherein said aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In an even more specific aspect of this embodiment the invention provides a compound of Formula I for treating and/or preventing a neurodegenerative disease or disorder where R8 is a phenyl group wherein said phenyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. Unless otherwise specified, according to the aspects described in this paragraph each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3. In a more specific definition, L is independently chosen from —(CH$_2$)$_n$—(CH$_2$)$_n$— and —(CH$_2$)$_n$O(CH$_2$)$_n$—, where each n is independently chosen from 0, 1, 2, and 3. In a more specific definition, L is chosen from a covalent bond or —CH$_2$—. In a more specific definition, L is a covalent bond.

In one embodiment, the invention provides a compound of Formula I:

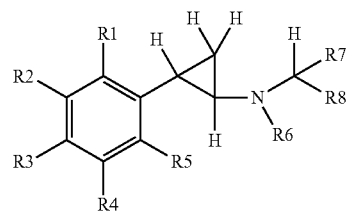

wherein
each of R1-R5 is independently chosen from —H, halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
R6 is chosen from —H and alkyl;
R7 is chosen from —H, alkyl, and cycloalkyl;
R8 is a -L-heterocyclyl or -L-aryl, wherein the ring or ring system of said -L-heterocyclyl or -L-aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3; and pharmaceutically acceptable salts thereof; with the provision that when R1, R2, R3, R4, R5, R6, and R7 are all hydro and L is a bond, then R8 is not 2,4-dimethoxyphenyl, 4-nitrophenyl, phenyl, 4-bromophenyl, 4-methoxyphenyl, 4-chlorophenyl, or furan-2-yl, and also when R1, R2, R3, R4, R5, and R7 are all hydro, L is a bond and R8 is phenyl, then R6 is not methyl, ethyl or isopentyl.

In one aspect of this embodiment, the invention provides a pharmaceutical composition comprising a pharmaceutically acceptable carrier and a compound of Formula I as defined above.

In one specific aspect of this embodiment the invention provides a compound of Formula I where R8 is -L-heterocyclyl wherein said heterocyclyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In a more specific aspect of this embodiment the invention provides a compound of Formula I where R8 is -L-heteroaryl wherein said heteroaryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In an even more specific aspect of this embodiment the invention provides a compound of Formula I where R8 is heteroaryl (L is a bond) wherein said heteroaryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. Unless otherwise specified, according to the aspects described in this paragraph each L is independently chosen from $-(CH_2)_n-(CH_2)_n-$, $-(CH_2)_nNH(CH_2)_n-$, $-(CH_2)_nO(CH_2)_n-$, and $-(CH_2)_nS(CH_2)_n-$, and where each n is independently chosen from 0, 1, 2, and 3. In a more specific definition, L is independently chosen from $-(CH_2)_n-(CH_2)_n-$ and $-(CH_2)_nO(CH_2)_n-$, where each n is independently chosen from 0, 1, 2, and 3. In a more specific definition, L is chosen from a covalent bond or $-CH_2-$. In a more specific definition, L is a covalent bond.

In one specific aspect of this embodiment the invention provides a compound of Formula I where R8 is -L-aryl wherein said aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In a more specific aspect of this embodiment the invention provides a compound of Formula I where R8 is aryl (L is a bond) wherein said aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In an even more specific aspect of this embodiment the invention provides a compound of Formula I where R8 is a phenyl group wherein said phenyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. According to the aspects described in this paragraph each L is independently chosen from $-(CH_2)_n-(CH_2)_n-$, $-(CH_2)_nNH(CH_2)_n-$, $-(CH_2)_nO(CH_2)_n-$, and $-(CH_2)_nS(CH_2)_n-$, and where each n is independently chosen from 0, 1, 2, and 3. In a more specific definition, L is independently chosen from $-(CH_2)_n-(CH_2)_n-$ and $-(CH_2)_nO(CH_2)_n-$, where each n is independently chosen from 0, 1, 2, and 3. In a more specific definition, L is chosen from a covalent bond or $-CH_2-$. In a more specific definition, L is a covalent bond.

In one embodiment, the invention provides a compound of Formula I wherein
R8 is heterocyclyl having from 0-3 substituents independently chosen from halo, alkyl, alkoxy, cycloalkoxy, haloalkyl, haloalkoxy, -L-aryl, -L-heteroaryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido; with the provision that when R1, R2, R3, R4, R5, R6, and R7 are all hydro, then R8 is not furan-2-yl.

In one embodiment, the invention provides compounds of Formula I wherein R6 and R7 are hydro.

In one embodiment, the invention provides a compound of Formula I wherein
R1-R7 are each hydro and R8 is aryl group having from 0-3 substituents independently chosen from halo, alkyl, alkoxy, cycloalkoxy, haloalkyl, haloalkoxy, -L-aryl, -L-heteroaryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido; with the provision that when R1, R2, R3, R4, R5, R6, and R7 are all hydro, then R8 is not 2,4-dimethoxyphenyl, 4-nitrophenyl, phenyl, 4-bromophenyl, 4-methoxyphenyl, or 4-chlorophenyl.

In one embodiment, the invention provides a compound of Formula I wherein the phenyl ring attached to the cyclopropyl ring has at least one substituent that is not hydro, i.e. at least one of R1 to R5 is not hydro.

In one embodiment, the invention provides a method of treating a cancer comprising administering, to a patient in need of treatment, a therapeutically effective amount of a composition comprising a compound of Formula I and a pharmaceutically acceptable carrier. Accordingly, in one embodiment, the invention provides a method for treating or preventing a cancer comprising the administration of a therapeutically effective amount of a compound of Formula I or a pharmaceutical composition comprising said compound and a pharmaceutically acceptable carrier to a subject (e.g. a human) in need of such a treatment or prevention. In a related embodiment, the invention provides a compound of Formula I for treating and/or preventing cancer. In another related embodiment, the invention provides for the use of a compound of Formula I for the manufacture of a medicament for treating and/or preventing cancer. In a specific aspect of the embodiments of this paragraph, the cancer is chosen from breast cancer, lung cancer, prostate cancer, testicular cancer, brain cancer, colorectal cancer, blood cancer (e.g., leukemia), or skin cancer. In a more specific aspect of the embodiments of this paragraph, the cancer is chosen from breast cancer, lung cancer, prostate cancer, testicular cancer, or brain cancer.

In one embodiment, the invention provides a method of inhibiting LSD1 activity comprising administering, to a patient in need of treatment, an amount of a composition comprising a compound of Formula I and a pharmaceutically acceptable carrier sufficient to inhibit LSD1 activity. In a related embodiment, the invention provides a compound of Formula I for inhibiting LSD1. In another related embodiment, the invention provides for the use of a compound of Formula I for the manufacture of a medicament for inhibiting LSD1.

In one embodiment, the invention provides a method of treating a neurodegenerative disease or disorder comprising administering, to a patient in need of treatment, a therapeutically effective amount of a composition comprising a compound of Formula I and a pharmaceutically acceptable carrier. Accordingly, in one embodiment, the invention provides a method for treating or preventing a neurodegenerative disease comprising the administration of a therapeutically effective amount of a compound of Formula I or a pharmaceutical composition comprising said compound and a pharmaceutically acceptable carrier to a subject (e.g. a human) in need of such a treatment or prevention. In a related embodiment, the invention provides a compound of Formula I for treating and/or preventing a neurodegenerative disease. In another related embodiment, the invention provides for the use of a compound of Formula I for the manufacture of a medicament for treating and/or preventing a neurodegenerative disease. In a specific aspect of the embodiments of this paragraph, the neurodegenerative disease or disorder is chosen from Alzheimer's disease, Parkinson's disease, Huntington's disease, or Lewy Body dementia.

In one embodiment, the invention provides a method of inhibiting monoamine oxidase activity comprising administering, to a patient in need of treatment, an amount of a composition comprising a compound of Formula I and a pharmaceutically acceptable carrier sufficient to inhibit monoamine oxidase activity. In a related embodiment, the invention provides a compound of Formula I for treating and/or preventing Parkinson's disease and/or depression. In another related embodiment, the invention provides for the use of a compound of Formula I for the manufacture of a medicament for inhibiting monoamine oxidase. In one specific aspect of this embodiment, the monoamine oxidase is MAO-B.

In one embodiment, the invention provides a method for identifying LSD1 selective inhibitors comprising determining the ability of a test compound to inhibit LSD1 and monoamine oxidase (MAO-A and/or MAO-B) wherein a test compound that inhibits LSD1 better than monoamine oxidase (MAO-A and/or MAO-B) is LSD1 selective. In one aspect of this embodiment, the test compound is chosen from a phenylcyclopropylamine derivative, homolog or analog.

In one embodiment, the invention provides a method for identifying a dual inhibitor selective for LSD1/MAO-B as compared to MAO-A comprising determining the ability of a test compound to inhibit LSD1 and monoamine oxidase (MAO-A and MAO-B) wherein a test compound that inhibits LSD1 and MAO-B better than LSD1 and monoamine oxidase (MAO-A and/or MAO-B) is a dual LSD1/MAO-B selective inhibitor. In one aspect of this embodiment, the test compound is chosen from a phenylcyclopropylamine derivative, homolog or analog.

Phenylcyclopropylamine derivatives, homologs, and analogs can be made by methods known in the art e.g., including, but not limited to the methods disclosed herein and in the references cited herein.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following detailed description, and from the claims.

The present invention relates to compounds, the identification of compounds and their use for treating and/or preventing diseases. The present invention provides compounds of Formula I, pharmaceutical compositions comprising a compound of Formula I and a pharmaceutically acceptable carrier, and their use for treating and/or preventing diseases. One use of the compounds of Formula I is to treat and/or prevent cancer. Compounds of the invention also inhibit monoamine oxidases, and can therefore be used for treating and/or preventing a disease in which monoamine oxidase inhibition is useful. Some compounds of Formula I can be used as LSD1 selective inhibitors that inhibit LSD1 to a greater extent than MAO-A and/or MAO-B. Some compounds of Formula I can be used as dual LSD1/MAO-B selective inhibitors that inhibit LSD1 and MAO-B to a greater extent than MAO-A. Some of the compounds of Formula I can be used as inhibitors of MAO-A, MAO-B and LSD1. In particular it was surprisingly found that phenylcyclopropylamine derivatives with monosubstitution on the amine group with ring bearing substituents yields compounds with unexpectedly potent LSD1 inhibition. For example, some of the compounds of Formula I have IC50 values for LSD1 inhibition of less than 1 micromolar (see Table 1) which makes them at least 20-30-fold more potent than tranylcypromine for LSD1 inhibition. Furthermore, these types of compounds also are potent inhibitors of the monoamine oxidases.

In one embodiment, the invention provides a pharmaceutical composition comprising a compound of Formula I and a pharmaceutically acceptable carrier:

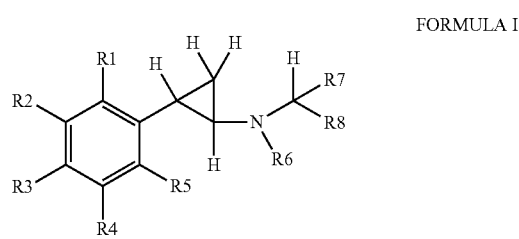

FORMULA I wherein
each of R1-R5 is independently chosen from —H, halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;

R6 is chosen from —H and alkyl;

R7 is chosen from —H, alkyl, and cycloalkyl;

R8 is -L-heterocyclyl or -L-aryl, wherein the ring or ring system of said -L-heterocyclyl or -L-aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;

each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3; and pharmaceutically acceptable salts thereof.

In one specific aspect of the pharmaceutical compositions of this embodiment, R8 is -L-heterocyclyl wherein said heterocyclyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In a more specific aspect, R8 is -L-heteroaryl wherein said heteroaryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In an even more specific aspect, R8 is heteroaryl (L is a bond) wherein said heteroaryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. Unless otherwise specified, according to the aspects described in this paragraph each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3. In a more specific definition, L is independently chosen from —(CH$_2$)$_n$—(CH$_2$)$_n$— and —(CH$_2$)$_n$O(CH$_2$)$_n$—, where each n is independently chosen from 0, 1, 2, and 3. In a more specific definition, L is chosen from a covalent bond or —CH$_2$—. In a more specific definition, L is a covalent bond.

In one specific aspect of the pharmaceutical compositions of this embodiment, R8 is -L-aryl wherein said aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In a more specific aspect, R8 is aryl (L is a bond) wherein said aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In an even more specific aspect, R8 is a phenyl group wherein said phenyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkynyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. Unless otherwise specified, according to the aspects described in this paragraph each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3. In a more specific definition, L is independently chosen from —(CH$_2$)$_n$—(CH$_2$)$_n$— and —(CH$_2$)$_n$O(CH$_2$)$_n$—, where each n is independently chosen from 0, 1, 2, and 3. In a more specific definition, L is chosen from a covalent bond or —CH$_2$—. In a more specific definition, L is a covalent bond.

In one aspect of this embodiment, the 0-3 substituents on the ring or ring system of R8 are independently chosen from hydroxyl, halo, alkyl, alkoxy, cycloalkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$, —CF$_3$, —CN, —NH$_2$, and —NO$_2$. In a more specific aspect, the R8 ring or ring system has 1 substituent chosen from hydroxyl, halo, alkyl, alkoxy, cycloalkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$—CF$_3$, —CN, —NH$_2$, and —NO$_2$. In an even more specific aspect, the R8 ring or ring system has 1 substituent chosen from halo, alkyl, alkoxy, haloalkyl, cyano, and hydroxyl.

In one aspect of this embodiment, the ring or ring system of R8 has 0-3 substituents. In a more specific aspect, the ring or ring system of R8 has 1-3 substituents. In a more specific aspect, the ring or ring system of R8 has 1 or 2 substituents. In an even more specific aspect, the ring or ring system of R8 has 1 substituent.

In a further aspect of this embodiment, the aforementioned substituent(s) on the ring or ring system of R8 are/is independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido, wherein each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and further wherein each n is independently chosen from 0, 1, 2, and 3. In a more specific aspect of this embodiment, the aforementioned substituent(s) on the ring or ring system of R8 are/is independently chosen from hydroxyl, halo, alkyl, alkoxy, cycloalkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$, —CF$_3$, —CN, —NH$_2$, and —NO$_2$. In an even more specific aspect, the aforementioned substituent(s) on the ring or ring system of R8 are/is independently chosen from halo, alkyl, alkoxy, haloalkyl, cyano, and hydroxyl.

In one aspect of this embodiment, R7 is chosen from —H and cycloalkyl. In a more specific aspect of this embodiment, R7 is —H.

In one aspect of this embodiment, L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3. In a more specific aspect, L is independently chosen from —(CH$_2$)$_n$—(CH$_2$)$_n$— and —(CH$_2$)$_n$O(CH$_2$)$_n$—, where each n is independently chosen from 0, 1, 2, and 3. In a more specific aspect, L is chosen from a covalent bond or —CH$_2$—. In an even more specific aspect, L is a covalent bond.

The invention provides a pharmaceutical composition comprising a pharmaceutically acceptable carrier and a compound of Formula I, as defined herein above, which is a selective inhibitor of LSD1. LSD1 selective inhibitors have IC50 values for LSD1 which are at least 2-fold lower than the IC50 value for MAO-A and/or MAO-B.

The invention also provides a pharmaceutical composition comprising a pharmaceutically acceptable carrier and a compound of Formula I, as defined herein above, which is a dual inhibitor selective for LSD1 and MAO-B. Dual LSD1/MAO-B selective inhibitors have IC50 values for LSD1 and MAO-B which are at least 2-fold lower than the IC50 value for MAO-A.

In one embodiment, the invention provides a compound of Formula I for treating and/or preventing cancer:

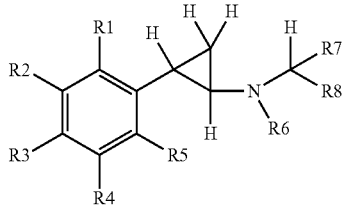

FORMULA I wherein
each of R1-R5 is independently chosen from —H, halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
R6 is chosen from —H and alkyl;
R7 is chosen from —H, alkyl, and cycloalkyl;
R8 is -L-heterocyclyl or -L-aryl, wherein the ring or ring system of said -L-heterocyclyl or -L-aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3; and pharmaceutically acceptable salts thereof.

In one aspect of this embodiment the invention provides a compound of Formula I for treating and/or preventing cancer, wherein the 0-3 substituents on the R8 ring or ring system are independently chosen from hydroxyl, halo, alkyl, alkoxy, cycloalkoxy, haloalkyl, haloalkoxy, alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$, —CF$_3$, —CN, —NH$_2$, and —NO$_2$. In a more specific aspect, the R8 ring or ring system has 1 substituent chosen from hydroxyl, halo, alkyl, alkoxy, cycloalkoxy, haloalkyl, haloalkoxy, —N(C$_{1-3}$ alkyl)$_2$, —NH (C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$, —CF$_3$, —CN, —NH$_2$, and —NO$_2$. In an even more specific aspect, the R8 ring or ring system has from 1 substituent chosen from halo, alkyl, alkoxy, haloalkyl, cyano, and hydroxyl.

In one aspect of this embodiment, the ring or ring system of R8 has 0-3 substituents. In a more specific aspect, the ring or ring system of R8 has 1-3 substituents. In a more specific aspect, the ring or ring system of R8 has 1 or 2 substituents. In an even more specific aspect, the ring or ring system of R8 has 1 substituent.

In a further aspect of this embodiment, the aforementioned substituent(s) on the ring or ring system of R8 are/is independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido, wherein each L is independently chosen from —(CH$_2$)$_n$—(CH$_2$)$_n$—, —(CH$_2$)$_n$NH(CH$_2$)$_n$—, —(CH$_2$)$_n$O $(CH_2)_n$—, and —$(CH_2)_nS(CH_2)_n$—, and further wherein each n is independently chosen from 0, 1, 2, and 3. In a more specific aspect of this embodiment, the aforementioned substituent(s) on the ring or ring system of R8 are/is independently chosen from hydroxyl, halo, alkyl, alkoxy, cycloalkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(O)$_2$N($C_{1-3}$ alkyl)$_2$, —S(=O)$_2$NH($C_{1-3}$ alkyl), —CHF$_2$, —OCF$_3$, —OCHF$_2$, —CN, —NH$_2$, and —NO$_2$. In an even more specific aspect, the aforementioned substituent (s) on the ring or ring system of R8 are/is independently chosen from halo, alkyl, alkoxy, haloalkyl, cyano, and hydroxyl.

In one aspect of this embodiment, R7 is chosen from —H and cycloalkyl. In a more specific aspect of this embodiment, R7 is —H.

In one aspect of this embodiment, L is independently chosen from —$(CH_2)_n$—$(CH_2)_n$—, —$(CH_2)_n$NH$(CH_2)_n$—, —$(CH_2)_nO(CH_2)_n$—, and —$(CH_2)_nS(CH_2)_n$—, where each n is independently chosen from 0, 1, 2, and 3. In a more specific aspect, L is independently chosen from —$(CH_2)_n$—$(CH_2)_n$— and —$(CH_2)_nO(CH_2)_n$—, where each n is independently chosen from 0, 1, 2, and 3. In a more specific aspect, L is chosen from a covalent bond or —CH$_2$—. In an even more specific aspect, L is a covalent bond.

In one specific aspect of this embodiment, the cancer is prostate cancer. In another specific aspect of this embodiment, the cancer is brain cancer. In yet another specific aspect of this embodiment, the cancer is breast cancer. In yet another specific aspect of this embodiment, the cancer is lung cancer. In yet another specific aspect of this embodiment, the cancer is testicular cancer. In yet another specific aspect of this embodiment, the cancer is colorectal cancer. In yet another specific aspect of this embodiment, the cancer is blood cancer (e.g., leukemia). In yet another specific aspect of this embodiment, the cancer is skin cancer.

In one specific aspect of this embodiment the invention provides a compound of Formula I for treating and/or preventing cancer where R8 is -L-heterocyclyl wherein said heterocyclyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In a more specific aspect of this embodiment the invention provides a compound of Formula I for treating and/or preventing cancer where R8 is -L-heteroaryl wherein said heteroaryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In an even more specific aspect of this embodiment the invention provides a compound of Formula I for treating and/or preventing cancer where R8 is heteroaryl (L is a bond) wherein said heteroaryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. Unless otherwise specified, according to the aspects described in this paragraph each L is independently chosen from —$(CH_2)_n$—$(CH_2)_n$—, —$(CH_2)_n$NH$(CH_2)_n$—, —$(CH_2)_nO(CH_2)_n$—, and —$(CH_2)_nS(CH_2)_n$—, and where each n is independently chosen from 0, 1, 2, and 3. In a more specific definition, L is independently chosen from —$(CH_2)_n$—$(CH_2)_n$— and —$(CH_2)_nO(CH_2)_n$—, where each n is independently chosen from 0, 1, 2, and 3. In a more specific definition, L is chosen from a covalent bond or —CH$_2$—. In a more specific definition, L is a covalent bond.

In one aspect of this embodiment, the invention provides a compound of Formula I for treating and/or preventing cancer, wherein the 0-3 substituents on the R8 ring or ring system are independently chosen from hydroxyl, halo, alkyl, alkoxy, cycloalkoxy, haloalkyl, haloalkoxy, alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(O)$_2$N($C_{1-3}$ alkyl)$_2$, —S(=O)$_2$NH($C_{1-3}$ alkyl), —CHF$_2$, —OCF$_3$, —OCHF$_2$, —CF$_3$, —CN, —NH$_2$, and —NO$_2$. In a more specific aspect, the R8 ring or ring system has 1 substituent chosen from hydroxyl, halo, alkyl, alkoxy, cycloalkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(O)$_2$N($C_{1-3}$ alkyl)$_2$, S(=O)$_2$NH($C_{1-3}$ alkyl), —CHF$_2$, —OCF$_3$, —OCHF$_2$, —CF$_3$, —CN, —NH$_2$, and —NO$_2$. In an even more specific aspect, the R8 ring or ring system has from 1 substituent chosen from halo, alkyl, alkoxy, haloalkyl, cyano, and hydroxyl.

In one aspect of this embodiment, the ring or ring system of R8 has 0-3 substituents. In a more specific aspect, the ring or ring system of R8 has 1-3 substituents. In a more specific aspect, the ring or ring system of R8 has 1 or 2 substituents. In an even more specific aspect, the ring or ring system of R8 has 1 substituent.

In a further aspect of this embodiment, the aforementioned substituent(s) on the ring or ring system of R8 are/is independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido, wherein each L is independently chosen from —$(CH_2)_n$—$(CH_2)_n$—, —$(CH_2)_n$NH$(CH_2)_n$—, —$(CH_2)_nO(CH_2)_n$—, and —$(CH_2)_nS(CH_2)_n$—, and further wherein each n is independently chosen from 0, 1, 2, and 3. In a more specific aspect of this embodiment, the aforementioned substituent(s) on the ring or ring system of R8 are/is independently chosen from hydroxyl, halo, alkyl, alkoxy, cycloalkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(O)$_2$N($C_{1-3}$ alkyl)$_2$, —S(=O)$_2$NH($C_{1-3}$ alkyl), —CHF$_2$, —OCF$_3$, —OCHF$_2$, —CF$_3$, —CN, —NH$_2$, and —NO$_2$. In an even more specific aspect, the aforementioned substituent(s) on the ring or ring system of R8 are/is independently chosen from halo, alkyl, alkoxy, haloalkyl, cyano, and hydroxyl.

In one aspect of this embodiment, R7 is chosen from —H and cycloalkyl. In a more specific aspect of this embodiment, R7 is —H.

In one aspect of this embodiment, L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3. In a more specific aspect, L is independently chosen from —(CH$_2$)$_n$—(CH$_2$)$_n$— and —(CH$_2$)$_n$O(CH$_2$)$_n$—, where each n is independently chosen from 0, 1, 2, and 3. In a more specific aspect, L is chosen from a covalent bond or —CH$_2$—. In an even more specific aspect, L is a covalent bond.

In one specific aspect of this embodiment the invention provides a compound of Formula I for treating and/or preventing cancer, wherein R8 is -L-aryl wherein said aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In a more specific aspect of this embodiment the invention provides a compound of Formula I for treating and/or preventing cancer where R8 is aryl (L is a bond) wherein said aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In an even more specific aspect of this embodiment the invention provides a compound of Formula I for treating and/or preventing cancer where R8 is a phenyl group wherein said phenyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. According to the aspects described in this paragraph each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3. In a more specific definition, L is independently chosen from —(CH$_2$)$_n$—(CH$_2$)$_n$— and —(CH$_2$)$_n$O(CH$_2$)$_n$—, where each n is independently chosen from 0, 1, 2, and 3. In a more specific definition, L is chosen from a covalent bond or —CH$_2$—. In a more specific definition, L is a covalent bond.

In one specific aspect of this embodiment the invention provides a compound of Formula I for treating and/or preventing cancer, wherein R8 is -L-aryl wherein said aryl has from 1-3 (i.e. 1, 2 or 3) substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In a more specific aspect of this embodiment the invention provides a compound of Formula I for treating and/or preventing cancer where R8 is aryl (L is a bond) wherein said aryl has from 1-3 (i.e. 1, 2 or 3) substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In an even more specific aspect of this embodiment the invention provides a compound of Formula I for treating and/or preventing cancer where R8 is a phenyl group wherein said phenyl has from 1-3 (i.e. 1, 2 or 3) substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. According to the aspects described in this paragraph each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3. In a more specific definition, L is independently chosen from —(CH$_2$)$_n$—(CH$_2$)$_n$— and —(CH$_2$)$_n$O(CH$_2$)$_n$—, where each n is independently chosen from 0, 1, 2, and 3. In a more specific definition, L is chosen from a covalent bond or —CH$_2$—. In a more specific definition, L is a covalent bond.

In one aspect of this embodiment, the invention provides a compound of Formula I for treating and/or preventing cancer, wherein the 0-3 substituents or the 1-3 substituents on the R8 ring or ring system are independently chosen from hydroxyl, halo, alkyl, alkoxy, cycloalkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$, —C$_3$, —CN, —NH$_2$, and —NO$_2$. In a more specific aspect, the R8 ring or ring system has 1 substituent chosen from hydroxyl, halo, alkyl, alkoxy, cycloalkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$, —CF$_3$, —CN, —NH$_2$, and —NO$_2$. In an even more specific aspect, the R8 ring or ring system has from 1 substituent chosen from halo, alkyl, alkoxy, haloalkyl, cyano, and hydroxyl.

In one aspect of this embodiment, the ring or ring system of R8 has 0-3 substituents. In a more specific aspect, the ring or ring system of R8 has 1-3 substituents. In a more specific aspect, the ring or ring system of R8 has 1 or 2 substituents. In an even more specific aspect, the ring or ring system of R8 has 1 substituent.

In a further aspect of this embodiment, the aforementioned substituent(s) on the ring or ring system of R8 are/is independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido, wherein each L is independently chosen from —$(CH_2)_n$—$(CH_2)_n$—, —$(CH_2)_n NH(CH_2)_n$—, —$(CH_2)_n O(CH_2)_n$—, and —$(CH_2)_n S(CH_2)_n$—, and further wherein each n is independently chosen from 0, 1, 2, and 3. In a more specific aspect of this embodiment, the aforementioned substituent(s) on the ring or ring system of R8 are/is independently chosen from hydroxyl, halo, alkyl, alkoxy, cycloalkoxy, haloalkyl, haloalkoxy, —$N(C_{1-3}$ alkyl$)_2$, —$NH(C_{1-3}$ alkyl), —$C(=O)NH_2$, —$C(=O)NH(C_{1-3}$ alkyl), —$C(=O)N(C_{1-3}$ alkyl$)_2$, —$S(=O)_2(C_{1-3}$alkyl), —$S(=O)_2 NH_2$, —$S(O)_2 N(C_{1-3}$ alkyl$)_2$, —$S(=O)_2 NH(C_{1-3}$ alkyl), —$CHF_2$, —$OCF_3$, —$OCHF_2$, —$CF_3$, —CN, —$NH_2$, and —$NO_2$. In an even more specific aspect, the aforementioned substituent(s) on the ring or ring system of R8 are/is independently chosen from halo, alkyl, alkoxy, haloalkyl, cyano, and hydroxyl.

In one aspect of this embodiment, R7 is chosen from —H and cycloalkyl. In a more specific aspect of this embodiment, R7 is —H.

In one aspect of this embodiment, L is independently chosen from —$(CH_2)_n$—$(CH_2)_n$—, —$(CH_2)_n NH(CH_2)_n$—, —$(CH_2)_n O(CH_2)_n$—, and —$(CH_2)_n S(CH_2)_n$—, where each n is independently chosen from 0, 1, 2, and 3. In a more specific aspect, L is independently chosen from —$(CH_2)_n$—$(CH_2)_n$— and —$(CH_2)_n O(CH_2)_n$—, where each n is independently chosen from 0, 1, 2, and 3. In a more specific aspect, L is chosen from a covalent bond or —$CH_2$—. In an even more specific aspect, L is a covalent bond.

In one aspect of this embodiment, the invention provides a pharmaceutical composition comprising a pharmaceutically acceptable carrier and a compound of Formula I as defined in the above described embodiment.

In a preferred aspect of this embodiment, the invention provides a compound of Formula I for use in treating and/or preventing cancer:

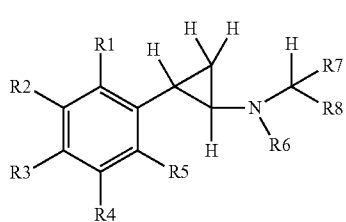

FORMULA I wherein:
each of R1-R5 is independently chosen from —H, halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;

R6 is chosen from —H and alkyl;
R7 is chosen from —H, alkyl, and cycloalkyl;
R8 is a -L-heterocyclyl wherein the ring or ring system of said -L-heterocyclyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido; or R8 is -L-aryl wherein the ring or ring system of said -L-aryl has from 1-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;

each L is independently chosen from —$(CH_2)_n$—$(CH_2)_n$—, —$(CH_2)_n NH(CH_2)_n$—, —$(CH_2)_n O(CH_2)_n$—, and —$(CH_2)_n S(CH_2)_n$—, and where each n is independently chosen from 0, 1, 2, and 3; or a pharmaceutically acceptable salt thereof.

In another more preferred aspect, R8 is a -L-heterocyclyl wherein the ring or ring system of said -L-heterocyclyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido.

In another more preferred aspect, R8 is -L-heterocyclyl wherein said -L-heterocyclyl is -L-heteroaryl wherein the ring or ring system of said -L-heteroaryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido.

In another more preferred aspect, R8 is a -L-heterocyclyl wherein the ring or ring system of said -L-heterocyclyl has from 0-3 substituents and further wherein said ring or ring system is chosen from pyridyl, thiazolyl, thiophenyl, quiolinyl, indolyl, oxadiazolyl, 2,3-dihydrobenzofuranyl, benzo[d][1,3]dioxolyl, 2,3-dihydrobenzo[b][1,4]dioxinyl, 3,4-dihydro-2H-benzo[b][1,4]dioxepinyl, and chromanyl.

In another more preferred aspect, R8 is a -L-heteroaryl wherein the ring or ring system of said -L-heteroaryl has from 0-3 substituents and further wherein said ring or ring system is chosen from pyridyl, thiazolyl, thiophenyl, quiolinyl, indolyl, and oxadiazolyl. In another more preferred aspect, R8 is a -L-heteroaryl wherein the ring or ring system of said -L-heteroaryl has from 0-3 substituents and further wherein said ring or ring system is pyridyl.

In another more preferred aspect, R8 is -L-aryl wherein the ring or ring system of said -L-aryl has from 1-3 (i.e. 1, 2 or 3) substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido.

In another more preferred aspect, R8 is aryl (L is a bond) wherein said aryl has from 1-3 (i.e. 1, 2 or 3) substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido.

In another more preferred aspect, L is independently chosen from —$(CH_2)_n$—$(CH_2)_n$— and —$(CH_2)_nO(CH_2)_n$—, wherein each n is independently chosen from 0, 1, 2, and 3. In another more preferred aspect, L is —$CH_2$— or a covalent bond. In another more preferred aspect, L is a covalent bond.

In another more preferred aspect, R6 and R7 are hydro.

In another more preferred aspect, at least one of R1 to R5 is not hydro. In another more preferred aspect, one of R1-R5 is chosen from -L-aryl, -L-heterocyclyl, and -L-carbocyclyl.

In another more preferred aspect, the substituent or the substituents on the R8 ring or ring system are chosen from hydroxyl, halo, alkyl, alkoxy, cycloalkoxy, haloalkyl, haloalkoxy, —$N(C_{1-3}$ alkyl$)_2$, —$NH(C_{1-3}$ alkyl), —$C(=O)NH_2$, —$C(=O)NH(C_{1-3}$ alkyl), —$C(=O)N(C_{1-3}$ alkyl$)_2$, —$S(=O)_2(C_{1-3}$alkyl), —$S(=O)_2NH_2$, —$S(O)_2N(C_{1-3}$ alkyl$)_2$, —$S(=O)_2NH(C_{1-3}$ alkyl), —CN, —$NH_2$, and —$NO_2$. In another more preferred aspect, the R8 ring or ring system has 1 substituent chosen from halo, alkyl, alkoxy, haloalkyl, cyano, and hydroxyl.

In another more preferred aspect, the cancer to be treated and/or prevented is chosen from breast cancer, lung cancer, prostate cancer, testicular cancer, brain cancer, colorectal cancer, blood cancer, and skin cancer.

In one embodiment, the invention provides a compound of Formula I:

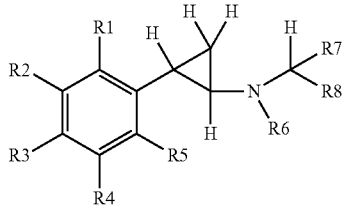

FORMULA I wherein
each of R1-R5 is independently chosen from —H, halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;

R6 is chosen from —H and alkyl;
R7 is chosen from —H, alkyl, and cycloalkyl;
R8 is a -L-heterocyclyl or -L-aryl, wherein the ring or ring system of said -L-heterocyclyl or -L-aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;

each L is independently chosen from —$(CH_2)_n$—$(CH_2)_n$—, —$(CH_2)_nNH(CH_2)_n$—, —$(CH_2)_nO(CH_2)_n$—, and —$(CH_2)_nS(CH_2)_n$—, and where each n is independently chosen from 0, 1, 2, and 3; and pharmaceutically acceptable salts thereof; with the provision that when R1, R2, R3, R4, R5, R6, and R7 are all hydro and L is a bond, then R8 is not 2,4-dimethoxyphenyl, 4-nitrophenyl, phenyl, 4-bromophenyl, 4-methoxyphenyl, 4-chlorophenyl or furan-2-yl, and also when R1, R2, R3, R4, R5, and R7 are all hydro, R8 is phenyl and L is a bond, then R6 is not methyl, ethyl or isopentyl.

In one aspect of this embodiment, the invention provides a pharmaceutical composition comprising a pharmaceutically acceptable carrier and a compound of Formula I as defined in the above described embodiment.

In one specific aspect of this embodiment the invention provides a compound of Formula I where R8 is -L-heterocyclyl wherein said heterocyclyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In a more specific aspect of this embodiment the invention provides a compound of Formula I where R8 is -L-heteroaryl wherein said heteroaryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In an even more specific aspect of this embodiment the invention provides a compound of Formula I where R8 is heteroaryl (L is a bond) wherein said heteroaryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. Unless otherwise specified, according to the aspects described in this paragraph each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3. In a more specific definition, L is independently chosen from —(CH$_2$)$_n$—(CH$_2$)$_n$— and —(CH$_2$)$_n$O(CH$_2$)$_n$—, where each n is independently chosen from 0, 1, 2, and 3. In a more specific definition, L is chosen from a covalent bond or —CH$_2$—. In a more specific definition, L is a covalent bond.

In one specific aspect of this embodiment the invention provides a compound of Formula I where R8 is -L-aryl wherein said aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In a more specific aspect of this embodiment the invention provides a compound of Formula I where R8 is aryl (L is a bond) wherein said aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In an even more specific aspect of this embodiment the invention provides a compound of Formula I where R8 is a phenyl group wherein said phenyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. Unless otherwise specified, according to the aspects described in this paragraph each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3. In a more specific definition, L is independently chosen from —(CH$_2$)$_n$—(CH$_2$)$_n$— and —(CH$_2$)$_n$O(CH$_2$)$_n$—, where each n is independently chosen from 0, 1, 2, and 3. In a more specific definition, L is chosen from a covalent bond or —CH$_2$—. In a more specific definition, L is a covalent bond.

In one specific aspect of this embodiment the invention provides a compound of Formula I where R8 is -L-aryl wherein said aryl has from 1-3 (i.e. 1, 2 or 3) substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In a more specific aspect of this embodiment the invention provides a compound of Formula I where R8 is aryl (L is a bond) wherein said aryl has from 1-3 (i.e. 1, 2 or 3) substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In an even more specific aspect of this embodiment the invention provides a compound of Formula I where R8 is a phenyl group wherein said phenyl has from 1-3 (i.e. 1, 2 or 3) substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. Unless otherwise specified, according to the aspects described in this paragraph each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3. In a more specific definition, L is independently chosen from —(CH$_2$)$_n$—(CH$_2$)$_n$— and —(CH$_2$)$_n$O(CH$_2$)$_n$—, where each n is independently chosen from 0, 1, 2, and 3. In a more specific definition, L is chosen from a covalent bond or —CH$_2$—. In a more specific definition, L is a covalent bond.

In one aspect of this embodiment, the invention provides a compound of Formula I wherein the 0-3 substituents or the 1-3 substituents on the R8 ring or ring system are independently chosen from hydroxyl, halo, alkyl, alkoxy, cycloalkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$, —CF$_3$, —CN, —NH$_2$, and —NO$_2$. In a more specific aspect, the R8 ring or ring system has 1 substituent chosen from hydroxyl, halo, alkyl, alkoxy, cycloalkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$, —CF$_3$, —CN, —NH$_2$, and —NO$_2$. In an even more specific aspect, the R8 ring or ring system has from 1 substituent chosen from halo, alkyl, alkoxy, haloalkyl, cyano, and hydroxyl.

In one aspect of this embodiment, the ring or ring system of R8 has 0-3 substituents. In a more specific aspect, the ring or ring system of R8 has 1-3 substituents. In a more specific aspect, the ring or ring system of R8 has 1 or 2 substituents. In an even more specific aspect, the ring or ring system of R8 has 1 substituent.

In a further aspect of this embodiment, the aforementioned substituent(s) on the ring or ring system of R8 are/is independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido, wherein each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and further wherein each n is independently chosen from 0, 1, 2, and 3. In a more specific aspect of this embodiment, the aforementioned substituent(s) on the ring or ring system of R8 are/is independently chosen from hydroxyl, halo, alkyl, alkoxy, cycloalkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$NH(C$_{1-3}$ alkyl)$_2$, —S(=O)$_2$NH(C$_{1-3}$ alkyl), —CHF$_2$, —OCF$_3$, —OCHF$_2$, —CF$_3$, —CN, —NH$_2$, and —NO$_2$. In an even more specific aspect, the aforementioned substituent(s) on the ring or ring system of R8 are/is independently chosen from halo, alkyl, alkoxy, haloalkyl, cyano, and hydroxyl.

In one aspect of this embodiment, R7 is chosen from —H and cycloalkyl. In a more specific aspect of this embodiment, R7 is —H.

In one aspect of this embodiment, L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3. In a more specific aspect, L is independently chosen from —(CH$_2$)$_n$—(CH$_2$)$_n$— and —(CH$_2$)$_n$O(CH$_2$)$_n$—, where each n is independently chosen from 0, 1, 2, and 3. In a more specific aspect, L is chosen from a covalent bond or —CH$_2$—. In an even more specific aspect, L is a covalent bond.

In a preferred aspect of this embodiment, the invention provides a compound of Formula I:

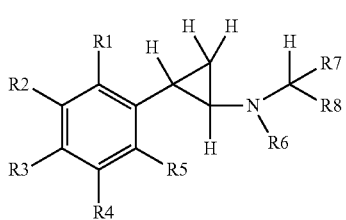

FORMULA 1 wherein:
each of R1-R5 is independently chosen from —H, halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;

R6 is chosen from —H and alkyl;
R7 is chosen from —H, alkyl, and cycloalkyl;
R8 is a -L-heterocyclyl wherein the ring or ring system of said -L-heterocyclyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido; or
R8 is -L-aryl wherein the ring or ring system of said -L-aryl has from 1-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and each n is independently chosen from 0, 1, 2, and 3; or a pharmaceutically acceptable salt thereof;
with the provision that when L is a bond and R1, R2, R3, R4, R5, R6, and R7 are all hydro, then R8 is not 2,4-dimethoxyphenyl, 4-nitrophenyl, phenyl, 4-bromophenyl, 4-methoxyphenyl, 4-chlorophenyl, or furan-2-yl, and also when R1, R2, R3, R4, R5, and R7 are all hydro, L is a bond and R8 is phenyl, then R6 is not methyl, ethyl, or isopentyl.

In a more preferred aspect, L is independently chosen from —(CH$_2$)$_n$—(CH$_2$)$_n$— and —(CH$_2$)$_n$O(CH$_2$)$_n$—, wherein each n is independently chosen from 0, 1, 2, and 3. In another more preferred aspect, L is —CH$_2$— or a covalent bond. In another more preferred aspect, L is a covalent bond.

In another more preferred aspect, R6 and R7 are each hydro.

In another more preferred aspect, R8 is an -L-heterocycyl wherein the ring or ring system of said -L-heterocyclyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido.

In another more preferred aspect, R8 is an -L-heterocyclyl wherein said -L-heterocyl is a -L-heteroaryl and wherein the ring or ring system of said -L-heteroaryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido.

In another more preferred aspect, R8 is a -L-heterocyclyl wherein the ring or ring system of said -L-heterocyclyl has from 0-3 substituents and further wherein said ring or ring system is chosen from pyridyl, thiazolyl, thiophenyl, quiolinyl, indolyl, oxadiazolyl, 2,3-dihydrobenzofuranyl, benzo[d][1,3]dioxolyl, 2,3-dihydrobenzo[b][1,4]dioxinyl, 3,4-dihydro-2H-benzo[b][1,4]dioxepinyl, and chromanyl.

In another more preferred aspect, R8 is a -L-heteroaryl wherein the ring or ring system of said -L-heteroaryl has from 0-3 substituents and further wherein said ring or ring system is chosen from pyridyl, thiazolyl, thiophenyl, quiolinyl, indolyl, and oxadiazolyl. In another more preferred aspect, R8 is a -L-heteroaryl wherein the ring or ring system of said -L-heteroaryl has from 0-3 substituents and further wherein said ring or ring system is pyridyl.

In another more preferred aspect, R8 is -L-aryl wherein the ring or ring system of said -L-aryl has from 1-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido.

In another more preferred aspect, R8 is an -L-aryl that has 3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido.

In another more preferred aspect, one of R1, R2, R3, R4, and R5 is not a hydro.

In another more preferred aspect, one of R1, R2, R3, R4, and R5 is chosen from -L-heterocyclyl, -L-aryl, and -L-carbocyclyl.

In another more preferred aspect, the substituent or the substituents on the R8 ring or ring system are chosen from hydroxyl, halo, alkyl, alkoxy, cycloalkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$NH$_2$, —S(O)$_2$N($C_{1-3}$ alkyl)$_2$, —S(=O)$_2$NH($C_{1-3}$ alkyl), —CN, —NH$_2$, and —NO$_2$.

In another more preferred aspect, the R8 ring or ring system has 1 substituent chosen from halo, alkyl, alkoxy, haloalkyl, cyano, and hydroxyl.

In one embodiment, the invention provides a compound of Formula I for treating and/or preventing cancer:

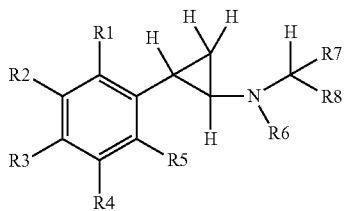

FORMULA I wherein
each of R1-R5 is independently chosen from —H, halo, alkyl, alkoxy, cycloalkoxy, haloalkyl, haloalkoxy, -L-aryl, -L-heteroaryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;

R6 is chosen from —H and alkyl;

R7 is chosen from —H, alkyl, and cycloalkyl;

R8 is chosen from -L-heterocyclyl and -L-aryl wherein the ring or ring system of said -L-heterocyclyl or -L-aryl has from 0-3 substituents independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;

each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3; and pharmaceutically acceptable salts thereof; with the provision that when R1, R2, R3, R4, R5, R6, and R7 are all hydro and L is a bond, then R8 is not 2,4-dimethoxyphenyl, 4-nitrophenyl, phenyl, 4-bromophenyl, 4-methoxyphenyl, 4-chlorophenyl, or furan-2-yl, and also when R1, R2, R3, R4, R5, and R7 are all hydro, R8 is phenyl and L is a bond, then R6 is not methyl, ethyl or isopentyl.

In one aspect of this embodiment, the invention provides a compound of Formula I for treating and/or preventing cancer wherein the 0-3 substituents on the R8 ring or ring system are independently chosen from hydroxyl, halo, alkyl, alkoxy, cycloalkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(O)$_2$N($C_{1-3}$ alkyl)$_2$, —S(=O)$_2$NH($C_{1-3}$ alkyl), —CHF$_2$, —OCHF$_2$, —CF$_3$, —CN, —NH$_2$, and —NO$_2$. In a more specific aspect, the R8 ring or ring system has 1 substituent chosen from hydroxyl, halo, alkyl, alkoxy, cycloalkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(O)$_2$N($C_{1-3}$ alkyl)$_2$, —S(=O)$_2$NH($C_{1-3}$ alkyl), —CHF$_2$, —OCF$_3$, —OCHF$_2$, —CF$_3$, —CN, —NH$_2$, and —NO$_2$. In an even more specific aspect, the R8 ring or ring system has from 1 substituent chosen from halo, alkyl, alkoxy, haloalkyl, cyano, and hydroxyl.

In one aspect of this embodiment, the ring or ring system of R8 has 0-3 substituents. In a more specific aspect, the ring or ring system of R8 has 1-3 substituents. In a more specific aspect, the ring or ring system of R8 has 1 or 2 substituents. In an even more specific aspect, the ring or ring system of R8 has 1 substituent.

In a further aspect of this embodiment, the aforementioned substituent(s) on the ring or ring system of R8 are/is independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido, wherein each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and further wherein each n is independently chosen from 0, 1, 2, and 3. In a more specific aspect of this embodiment, the aforementioned substituent(s) on the ring or ring system of R8 are/is independently chosen from hydroxyl, halo, alkyl, alkoxy, cycloalkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$, —CF$_3$, —CN, —NH$_2$, and —NO$_2$. In an even more specific aspect, the aforementioned substituent(s) on the ring or ring system of R8 are/is independently chosen from halo, alkyl, alkoxy, haloalkyl, cyano, and hydroxyl.

In one aspect of this embodiment, R7 is chosen from —H and cycloalkyl. In a more specific aspect of this embodiment, R7 is —H.

In one aspect of this embodiment, L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3. In a more specific aspect, L is independently chosen from —(CH$_2$)$_n$—(CH$_2$)$_n$— and —(CH$_2$)$_n$O(CH$_2$)$_n$—, where each n is independently chosen from 0, 1, 2, and 3. In a more specific aspect, L is chosen from a covalent bond or —CH$_2$—. In an even more specific aspect, L is a covalent bond.

In one embodiment, the invention provides a pharmaceutical composition comprising a pharmaceutically acceptable carrier and a compound of Formula I wherein
each of R1-R5 is independently chosen from —H, halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
R6 is chosen from —H and alkyl;
R7 is chosen from —H, alkyl, and cycloalkyl;
R8 is chosen from -L-heterocyclyl and -L-aryl wherein the ring or ring system of said -L-heterocyclyl or -L-aryl has from 0-3 substituents independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3; and pharmaceutically acceptable salts thereof; with the provision that when R1, R2, R3, R4, R5, R6, and R7 are all hydro and L is a bond, then R8 is not 2,4-dimethoxyphenyl, 4-nitrophenyl, phenyl, 4-bromophenyl, 4-methoxyphenyl, 4-chlorophenyl or furan-2-yl, and also when R1, R2, R3, R4, R5, and R7 are all hydro, R8 is phenyl and L is a bond, then R6 is not methyl, ethyl or isopentyl.

In one aspect of this embodiment, the invention provides a pharmaceutical composition comprising a pharmaceutically acceptable carrier and a compound of Formula I wherein the 0-3 substituents on the R8 ring or ring system are independently chosen from hydroxyl, halo, alkyl, alkoxy, cycloalkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$, —CF$_3$, —CN, —NH$_2$, and —NO$_2$. In a more specific aspect, the R8 ring or ring system has 1 substituent chosen from hydroxyl, halo, alkyl, alkoxy, cycloalkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$, —CF$_3$, —CN, —NH$_2$, and —NO$_2$. In an even more specific aspect, the R8 ring or ring system has from 1 substituent chosen from halo, alkyl, alkoxy, haloalkyl, cyano, and hydroxyl.

In one aspect of this embodiment, the ring or ring system of R8 has 0-3 substituents. In a more specific aspect, the ring or ring system of R8 has 1-3 substituents. In a more specific aspect, the ring or ring system of R8 has 1 or 2 substituents. In an even more specific aspect, the ring or ring system of R8 has 1 substituent.

In a further aspect of this embodiment, the aforementioned substituent(s) on the ring or ring system of R8 are/is independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido, wherein each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and further wherein each n is independently chosen from 0, 1, 2, and 3. In a more specific aspect of this embodiment, the aforementioned substituent(s) on the ring or ring system of R8 are/is independently chosen from hydroxyl, halo, alkyl, alkoxy, cycloalkoxy, haloalkyl, haloalkoxy, —N(C$_{1-3}$ alkyl)$_2$, —NH(C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$, —CF$_3$, —CN, —NH$_2$, and —NO$_2$. In an even more specific aspect, the aforementioned substituent(s) on the ring or ring system of R8 are/is independently chosen from halo, alkyl, alkoxy, haloalkyl, cyano, and hydroxyl.

In one aspect of this embodiment, R7 is chosen from —H and cycloalkyl. In a more specific aspect of this embodiment, R7 is —H.

In one aspect of this embodiment, L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)S(CH$_2$)$_n$—, where each n is independently chosen from 0, 1, 2, and 3. In a more specific aspect, L is independently chosen from —(CH$_2$)$_n$—(CH$_2$)$_n$— and —(CH$_2$)$_n$O(CH$_2$)$_n$—, where each n is independently chosen from 0, 1, 2, and 3. In a more specific aspect, L is chosen from a covalent bond or —CH$_2$—. In an even more specific aspect, L is a covalent bond.

In one embodiment, the invention provides a compound of Formula I wherein
each of R1-R5 is independently chosen from —H, halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
R6 is chosen from —H and $C_{1-6}$ alkyl;
R7 is chosen from —H, alkyl, and cycloalkyl;
R8 is -L-heterocyclyl or -L-aryl wherein the ring or ring system of said -L-heterocyclyl or -L-aryl has from 0-3 substituents wherein said substituents are chosen from hydroxyl, halo, alkyl, alkoxy, cycloalkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(O)$_2$N(C alkyl)$_2$, —S(=O)$_2$NH($C_{1-3}$ alkyl), —CHF$_2$, —OCF$_3$, —OCHF$_2$, —CF$_3$, —CN, —NH$_2$, and —NO$_2$;
each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3; and pharmaceutically acceptable salts thereof;
with the provision that when R1, R2, R3, R4, R5, R6, and R7 are all hydro and L is a bond, then R8 is not 2,4-dimethoxyphenyl, 4-nitrophenyl, phenyl, 4-bromophenyl, 4-methoxyphenyl, 4-chlorophenyl or furan-2-yl, and also when R1, R2, R3, R4, R5, and R7 are all hydro, R8 is phenyl and L is a bond, then R6 is not methyl, ethyl or isopentyl.

In one aspect of this embodiment, R7 is chosen from —H and cycloalkyl. In a more specific aspect of this embodiment, R7 is —H.

In a more specific aspect of this embodiment, R6 and R7 are each hydro. In an even more specific aspect, R1, R2, R3, R4, R5, R6, and R7 are each hydro.

In a specific aspect of this embodiment, R8 is a heteroaryl having from 0-3 substituents. In a specific aspect, the heteroaryl ring is chosen from thiazolyl, pyridyl, thiophenyl, and quinolinyl. In one specific aspect, R8 is a heteroaryl that has from 1 to 3 substituents independently chosen from hydroxyl, halo, alkyl, alkoxy, cycloalkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(O)$_2$N($C_{1-3}$ alkyl)$_2$, —S(=O)$_2$NH($C_{1-3}$ alkyl), —CHF$_2$, —OCF$_3$, —OCHF$_2$, —CF$_3$, —CN, —NH$_2$, and —NO$_2$. In a more specific aspect, R8 is a heteroaryl that has from 1-3 substituents independently chosen from halo, alkyl, alkoxy, haloalkyl, cyano, and hydroxyl.

In one aspect of this embodiment, R8 is not an unsubstituted furan-2-yl or phenyl group when L is a bond.

In one specific aspect of this embodiment, the invention provides a compound of Formula I wherein R1, R2, R3, R4, R5, R6 and R7 are each hydro and R8 is an -L-aryl group having from 0 to 3 substituents on the ring or ring system of said -L-aryl, the substituents being independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3; and pharmaceutically acceptable salts thereof;
provided that when L is a bond, R8 is not 2,4-dimethoxyphenyl, phenyl, 4-nitrophenyl, 4-bromophenyl, 4-methoxyphenyl or 4-chlorophenyl.

In a more specific aspect, R8 is a phenyl group having from 1 to 3 substituents. In a more specific aspect, the substituents on the R8 phenyl ring are chosen from halo, alkyl, alkoxy, cycloalkoxy, cyano, haloalkyl and hydroxyl. In another more specific aspect the substituents on the R8 ring are chosen from —F, —Cl, —Br, —CH$_3$, —OH, —CF$_3$, cyano, and —OCH$_3$.

Each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3; and pharmaceutically acceptable salts thereof;
provided that when L is a bond, R8 is not 2,4-dimethoxyphenyl, 4-nitrophenyl, 4-bromophenyl, 4-methoxyphenyl or 4-chlorophenyl.

In one aspect of this embodiment, the invention provides a pharmaceutical composition comprising a pharmaceutically acceptable carrier and a compound of Formula I as defined above.

In one embodiment, the invention provides a compound of Formula I wherein:
one of R1-R5 is chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
and the others of R1-R5 are independently chosen from —H, halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
R6 is chosen from —H and alkyl;
R7 is chosen from —H, alkyl, and cycloalkyl;
R8 is chosen from -L-heterocyclyl and -L-aryl wherein the ring or ring system of said -L-heterocyclyl or -L-aryl has from 0-3 substituents independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3; and pharmaceutically acceptable salts thereof.

In one aspect of this embodiment, the ring or ring system of R8 has 0-3 substituents. In a more specific aspect, the ring or ring system of R8 has 1-3 substituents. In a more specific aspect, the ring or ring system of R8 has 1 or 2 substituents. In an even more specific aspect, the ring or ring system of R8 has 1 substituent.

In a further aspect of this embodiment, the aforementioned substituent(s) on the ring or ring system of R8 are/is independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido, wherein each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and further wherein each n is independently chosen from 0, 1, 2, and 3. In a more specific aspect of this embodiment, the aforementioned substituent(s) on the ring or ring system of R8 are/is independently chosen from hydroxyl, halo, alkyl, alkoxy, cycloalkoxy, haloalkyl, haloalkoxy, —N(C$_{1-3}$ alkyl)$_2$, —NH (C$_{1-3}$ alkyl), —C(=O)NH$_2$, —C(=O)NH(C$_{1-3}$ alkyl), —C(=O)N(C$_{1-3}$ alkyl)$_2$, —S(=O)$_2$(C$_{1-3}$alkyl), —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$, —CF$_3$, —CN, —NH$_2$, and —NO$_2$. In an even more specific aspect, the aforementioned substituent(s) on the ring or ring system of R8 are/is independently chosen from halo, alkyl, alkoxy, haloalkyl, cyano, and hydroxyl.

In one aspect of this embodiment, R7 is chosen from —H and cycloalkyl. In a more specific aspect of this embodiment, R7 is —H.

In one aspect of this embodiment, L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3. In a more specific aspect, L is independently chosen from —(CH$_2$)$_n$—(CH$_2$)$_n$— and —(CH$_2$)$_n$O(CH$_2$)$_n$—, where each n is independently chosen from 0, 1, 2, and 3. In a more specific aspect, L is chosen from a covalent bond or —CH$_2$—. In an even more specific aspect, L is a covalent bond.

In one aspect of this embodiment, the invention provides a compound of Formula I wherein one of R1-R5 is a substituent chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
and the others of R1-R5 are each hydro;
R6 and R7 are each hydro; and
R8 is chosen from aryl or heterocyclyl wherein the ring or ring system of said aryl or heterocyclyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3; and pharmaceutically acceptable salts thereof.

In one aspect of this embodiment, the ring or ring system of R8 has 1-3 substituents as described and defined above. In a more specific aspect, the ring or ring system of R8 has 1 or 2 substituents as defined above. In an even more specific aspect, the ring or ring system of R8 has 1 substituent as defined above.

In one specific aspect of this embodiment, R8 has from 1-3 substituents independently chosen from hydroxyl, halo, alkyl, alkoxy, cycloalkoxy, haloalkyl, haloalkoxy, —N(C$_{1-3}$ alkyl)$_2$, —NH(C$_{1-3}$ alkyl), —C(=O)NH$_2$, —C(=O)NH (C$_{1-3}$ alkyl), —C(=O)N(C$_{1-3}$ alkyl)$_2$, —S(=O)$_2$(C$_{1-3}$ alkyl), —S(=O)$_2$NH$_2$, —S(O)$_2$N(C$_{1-3}$ alkyl)$_2$, —S(=O)$_2$NH(C$_{1-3}$ alkyl), —CHF$_2$, —OCF$_3$, —OCHF$_2$, —CF$_3$, —CN, —NH$_2$, and —NO$_2$.

In one specific aspect of this embodiment, the one of R1-R5 is chosen from -L-aryl, -L-heterocyclyl, and -L-carbocyclyl. In an even more specific aspect, the one of R1-R5 is -L-aryl. In an even more specific aspect, the one of R1-R5 is benzyloxy.

In one specific aspect of this embodiment, the substituent(s) on R8 are independently chosen from halo, alkyl, alkoxy, cycloalkoxy, cyano, haloalkyl, and hydroxyl.

In one aspect of this embodiment, the invention provides a pharmaceutical composition comprising a pharmaceutically acceptable carrier and a compound of Formula I as defined above.

In one embodiment, the invention provides a compound of Formula I wherein:
each of R1-R5 is independently chosen from —H, halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
R6 is —H;
R7 is —H;
R8 is chosen from -L-heterocyclyl and -L-aryl, wherein the ring or ring system of said -L-heterocyclyl or -L-aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3; and pharmaceutically acceptable salts thereof;

with the provision that when R1, R2, R3, R4, and R5 are all hydro and L is a bond, then R8 is not 2,4-dimethoxyphenyl, 4-nitrophenyl, 4-bromophenyl, 4-methoxyphenyl, 4-chlorophenyl, or furan-2-yl.

In one aspect of this embodiment, L is independently chosen from —$(CH_2)_n$—$(CH_2)_n$—, —$(CH_2)_n NH(CH_2)_n$—, —$(CH_2)_n O(CH_2)_n$—, and —$(CH_2)_n S(CH_2)_n$—, where each n is independently chosen from 0, 1, 2, and 3. In a more specific aspect, L is independently chosen from —$(CH_2)_n$—$(CH_2)_n$— and —$(CH_2)_n O(CH_2)_n$—, where each n is independently chosen from 0, 1, 2, and 3. In a more specific aspect, L is chosen from a covalent bond or —$CH_2$—. In an even more specific aspect, L is a covalent bond.

In one aspect of this embodiment, the ring or ring system of R8 has 0-3 substituents. In a more specific aspect, the ring or ring system of R8 has 1-3 substituents. In a more specific aspect, the ring or ring system of R8 has 1 or 2 substituents. In an even more specific aspect, the ring or ring system of R8 has 1 substituent.

In a further aspect of this embodiment, the aforementioned substituent(s) on the ring or ring system of R8 are/is independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido, wherein each L is independently chosen from —$(CH_2)_n$—$(CH_2)_n$—, —$(CH_2)_n NH(CH_2)_n$—, —$(CH_2)_n O(CH_2)_n$—, and —$(CH_2)_n S(CH_2)_n$—, and further wherein each n is independently chosen from 0, 1, 2, and 3. In a more specific aspect of this embodiment, the aforementioned substituent(s) on the ring or ring system of R8 are/is independently chosen from hydroxyl, halo, alkyl, alkoxy, cycloalkoxy, haloalkyl, haloalkoxy, —$N(C_{1-3}$ alkyl$)_2$, —$NH(C_{1-3}$ alkyl$)$, —$C(=O)NH_2$, —$C(=O)NH(C_{1-3}$ alkyl$)$, —$C(=O)N(C_{1-3}$ alkyl$)_2$, —$S(=O)_2(C_{1-3}$alkyl$)$, —$S(=O)_2 NH_2$, —$S(O)_2 N(C_{1-3}$ alkyl$)_2$, —$S(=O)_2 NH(C_{1-3}$ alkyl$)$, —$CHF_2$, —$OCF_3$, —$OCHF_2$, —$CF_3$, —CN, —$NH_2$, and —$NO_2$. In an even more specific aspect, the aforementioned substituent(s) on the ring or ring system of R8 are/is independently chosen from halo, alkyl, alkoxy, haloalkyl, cyano, and hydroxyl.

In one aspect of this embodiment, the invention provides a compound of Formula I wherein the 0-3 substituents on the R8 ring or ring system are independently chosen from halo, alkoxy, cycloalkoxy, cyano, and alkyl. In a more specific aspect the R8 ring or ring system has 1 or 2 substituents independently chosen from halo, alkoxy, cycloalkoxy, cyano, and alkyl. In an even more specific aspect, the R8 ring or ring system has 1 substituent independently chosen from halo, alkoxy, cyano, and alkyl.

In one aspect of this embodiment, the invention provides a compound of Formula I wherein the 0-3 substituents on the R8 ring or ring system are independently chosen from —Cl, —Br, —F, cyano, and methoxy. In a more specific aspect the R8 ring or ring system has 1 or 2 substituents independently chosen from —Cl, —Br, —F, cyano, and methoxy. In an even more specific aspect, the R8 ring or ring system has 1 substituent independently chosen from —Cl, —Br, —F, cyano, and methoxy.

In one aspect of this embodiment, the invention provides a compound of Formula I wherein R8 is chosen from phenyl, thiazolyl, pyridyl, thiophenyl, and quinolinyl.

In one aspect of this embodiment, the invention provides a pharmaceutical composition comprising a pharmaceutically acceptable carrier and a compound of Formula I as defined above.

In one embodiment, the invention provides compounds of Formula I wherein
each of R1-R5 is independently chosen from —H, halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
R6 is chosen from —H and alkyl;
R7 is chosen from —H, alkyl, and cycloalkyl;
R8 is chosen from -L-heterocyclyl and -L-aryl wherein the ring or ring system of said -L-heterocyclyl or -L-aryl has from 0-3 substituents independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
each L is independently chosen from —$(CH_2)_n$—$(CH_2)_n$—, —$(CH_2)_n NH(CH_2)_n$—, —$(CH_2)_n O(CH_2)_n$—, and —$(CH_2)_n S(CH_2)_n$—, and where each n is independently chosen from 0, 1, 2, and 3; and pharmaceutically acceptable salts thereof;
with the provision that when R1 to R7 are all hydro and L is a bond, then R8 is not an unsubstituted phenyl group, a 4-halophenyl group, a 4-methoxyphenyl group, a 2,4-dimethoxyphenyl group, a 4-nitrophenyl group or a furanyl group, and also when R1 to R5 and R7 are all hydro, R8 is phenyl and L is a bond, then R6 is not methyl, ethyl or isopentyl.

In one aspect of this embodiment, R7 is chosen from —H and cycloalkyl. In a more specific aspect of this embodiment, R7 is —H.

In one aspect of this embodiment, the ring or ring system of R8 has 1-3 substituents as described and defined above. In a more specific aspect, the ring or ring system of R8 has 1 or 2 substituents as defined above. In an even more specific aspect, the ring or ring system of R8 has 1 substituent as defined above.

In one aspect of this embodiment, the invention provides a compound of Formula I wherein R8 is aryl wherein the ring or ring system of said aryl has from 0-3 substituents independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido.

In one aspect of this embodiment, the invention provides a compound of Formula I wherein R8 is heteroaryl wherein the ring or ring system of said heteroaryl has from 0-3 substituents independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido.

In one aspect of this embodiment, the invention provides a compound of Formula I wherein R8 is heterocyclyl wherein the ring or ring system of said heterocyclyl has from 0-3 substituents independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cyclo alkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, hetero arylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido.

In one aspect of this embodiment, the invention provides a compound of Formula I wherein R8 is chosen from phenyl, pyridinyl, thiazolyl, and thiophenyl, wherein the ring of said group has from 0-3 substituents independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido.

In one aspect of this embodiment, the invention provides a compound of Formula I wherein the substituents on the R8 ring or ring system are independently chosen from hydroxyl, halo, alkyl, alkoxy, cycloalkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(O)$_2$N($C_{1-3}$ alkyl)$_2$, —S(=O)$_2$NH($C_{1-3}$ alkyl), —CHF$_2$, —OCF$_3$, —OCHF$_2$, —CF$_3$, —CN, —NH$_2$, and —NO$_2$.

In one aspect of this embodiment, the invention provides a compound of Formula I wherein the 0-3 substituents on the R8 ring or ring system are independently chosen from halo, alkoxy, cycloalkoxy, cyano, and alkyl. In a more specific aspect, the R8 ring or ring system has 1 or 2 substituents independently chosen from halo, alkoxy, cycloalkoxy, cyano, and alkyl. In an even more specific aspect, the R8 ring or ring system has 1 substituent chosen from halo, alkoxy, cyano, and alkyl.

In one aspect of this embodiment, the invention provides a compound of Formula I wherein the 0-3 substituents on the R8 ring or ring system are independently chosen from —Cl, —Br, —F, cyano, and methoxy. In a more specific aspect the R8 ring or ring system has 1 or 2 substituents independently chosen from —Cl, —Br, —F, cyano, and methoxy. In an even more specific aspect, the R8 ring or ring system has 1 substituent chosen from —Cl, —Br, —F, cyano, and methoxy.

In one aspect of this embodiment, the invention provides a pharmaceutical composition comprising a pharmaceutically acceptable carrier and a compound of Formula I as defined above.

In one embodiment, the invention provides a compound of Formula I wherein
R1, R2, R3, R4, and R5 are each hydro;
R6 is chosen from —H and alkyl;
R7 is chosen from —H, alkyl, and cycloalkyl;
R8 is chosen from -L-heterocyclyl and -L-aryl wherein the ring or ring system of said -L-heterocyclyl or -L-aryl has from 0-3 substituents independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido;
each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3; and pharmaceutically acceptable salts thereof, with the provision that when R6 and R7 are both hydro and L is a bond, then R8 is not 2,4-dimethoxyphenyl, 4-nitrophenyl, phenyl, 4-bromophenyl, 4-methoxyphenyl, 4-chlorophenyl, or furan-2-yl, and also when R7 is hydro, L is a bond and R8 is phenyl, then R6 is not methyl, ethyl or isopentyl.

In one aspect of this embodiment, R7 is chosen from —H and cycloalkyl. In a more specific aspect of this embodiment, R7 is —H.

In one aspect of this embodiment, the ring or ring system of R8 has 0-3 substituents. In a more specific aspect, the ring or ring system of R8 has 1-3 substituents. In a more specific aspect, the ring or ring system of R8 has 1 or 2 substituents. In an even more specific aspect, the ring or ring system of R8 has 1 substituent.

In a further aspect of this embodiment, the aforementioned substituent(s) on the ring or ring system of R8 are/is independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido, wherein each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and further wherein each n is independently chosen from 0, 1, 2, and 3. In a more specific aspect of this embodiment, the aforementioned substituent(s) on the ring or ring system of R8 are/is independently chosen from hydroxyl, halo, alkyl, alkoxy, cycloalkoxy, haloalkyl, haloalkoxy, —N($C_{1-3}$ alkyl)$_2$, —NH ($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(O)$_2$N($C_{1-3}$ alkyl)$_2$, —S(=O)$_2$NH($C_{1-3}$ alkyl), —CHF$_2$, —OCF$_3$, —OCHF$_2$, —CF$_3$, —CN, —NH$_2$, and —NO$_2$. In an even more specific aspect, the aforementioned substituent(s) on the ring or ring system of R8 are/is independently chosen from halo, alkyl, alkoxy, haloalkyl, cyano, and hydroxyl.

In one aspect of this embodiment, L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, where each n is independently chosen from 0, 1, 2, and 3. In a more specific aspect, L is independently chosen from —(CH$_2$)$_n$—

$(CH_2)_n$— and —$(CH_2)_nO(CH_2)_n$—, where each n is independently chosen from 0, 1, 2, and 3. In a more specific aspect, L is chosen from a covalent bond or —$CH_2$—. In an even more specific aspect, L is a covalent bond.

In one aspect of this embodiment, the invention provides a pharmaceutical composition comprising a pharmaceutically acceptable carrier and a compound of Formula I as defined above.

In one embodiment, the invention provides a compound of Formula I wherein
one of R1, R2, R3, R4, and R5 is chosen from halo, alkyl, alkoxyl, haloalkyl, haloalkoxy, cyano, amino, alkylamino, -L-heterocyclyl, -L-aryl, and -L-carbocyclyl; and the others of R1, R2, R3, R4, and R5 are chosen from —H, halo, alkyl, alkoxyl, haloalkyl, haloalkoxy, cyano, amino, alkylamino, -L-heterocyclyl, -L-aryl, and -L-carbocyclyl;
R6 is chosen from —H and alkyl;
R7 is chosen from —H, alkyl, and cycloalkyl;
R8 is chosen from heteroaryl and aryl, wherein the ring or ring system of said heteroaryl or aryl has from 0-3 substituent independently chosen from halo, alkyl, alkoxy, cycloalkoxy, haloalkyl, haloalkoxy, -L-aryl, -L-heteroaryl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido;
each L is independently chosen from —$(CH_2)_n$—$(CH_2)_n$—, —$(CH_2)_nNH(CH_2)_n$—, —$(CH_2)_nO(CH_2)_n$—, and —$(CH_2)_nS(CH_2)_n$—, and where each n is independently chosen from 0, 1, 2, and 3; and pharmaceutically acceptable salts thereof.

In one aspect of this embodiment, R7 is chosen from —H and cycloalkyl. In a more specific aspect of this embodiment, R7 is —H.

In one aspect of this embodiment, the ring or ring system of R8 has 0-3 substituents. In a more specific aspect, the ring or ring system of R8 has 1-3 substituents. In a more specific aspect, the ring or ring system of R8 has 1 or 2 substituents. In an even more specific aspect, the ring or ring system of R8 has 1 substituent.

In a further aspect of this embodiment, the aforementioned substituent(s) on the ring or ring system of R8 are/is independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido, wherein each L is independently chosen from —$(CH_2)_n$—$(CH_2)_n$—, —$(CH_2)_nNH(CH_2)_n$—, —$(CH_2)_nO(CH_2)_n$—, and —$(CH_2)_nS(CH_2)_n$—, and further wherein each n is independently chosen from 0, 1, 2, and 3. In a more specific aspect of this embodiment, the aforementioned substituent(s) on the ring or ring system of R8 are/is independently chosen from hydroxyl, halo, alkyl, alkoxy, cycloalkoxy, haloalkyl, haloalkoxy, —$N(C_{1-3}$ alkyl$)_2$, —NH$(C_{1-3}$ alkyl), —C(=O)NH$_2$, —C(=O)NH$(C_{1-3}$ alkyl), —C(=O)N$(C_{1-3}$ alkyl$)_2$, —S(=O)$_2(C_{1-3}$alkyl), —S(=O)$_2$NH$_2$, —S(O)$_2$N$(C_{1-3}$ alkyl$)_2$, —S(=O)$_2$NH$(C_{1-3}$ alkyl), —CHF$_2$, —OCF$_3$, —OCHF$_2$, —CF$_3$, —CN, —NH$_2$, and —NO$_2$. In an even more specific aspect, the aforementioned substituent(s) on the ring or ring system of R8 are/is independently chosen from halo, alkyl, alkoxy, haloalkyl, cyano, and hydroxyl.

In one aspect of this embodiment, L is independently chosen from —$(CH_2)_n$—$(CH_2)_n$—, —$(CH_2)_nNH(CH_2)_n$—, —$(CH_2)_nO(CH_2)_n$—, and —$(CH_2)_nS(CH_2)_n$—, where each n is independently chosen from 0, 1, 2, and 3. In a more specific aspect, L is independently chosen from —$(CH_2)_n$—$(CH_2)_n$— and —$(CH_2)_nO(CH_2)_n$—, where each n is independently chosen from 0, 1, 2, and 3. In a more specific aspect, L is chosen from a covalent bond or —$CH_2$—. In an even more specific aspect, L is a covalent bond.

In one specific aspect of this embodiment, the invention provides a compound of Formula I wherein one of R1, R2, R3, R4, and R5 is chosen from -L-heterocyclyl, -L-aryl, and -L-carbocyclyl. In a more specific aspect of this embodiment, one of R1, R2, R3, R4, and R5 is chosen from -L-heterocyclyl, -L-aryl, and -L-carbocyclyl, and the others are hydro. In an even more specific aspect L is a covalent bond.

In one specific aspect of this embodiment, the invention provides a compound of Formula I wherein R6 and R7 are hydro, and one of R1, R2, R3, R4, and R5 is chosen from -L-heterocyclyl, -L-aryl, and -L-carbocyclyl. In a more specific aspect of this embodiment, R6 and R7 are hydro, one of R1, R2, R3, R4, and R5 is chosen from -L-heterocyclyl, -L-aryl, and -L-carbocyclyl, and the others of R1 to R5 are hydro. In an even more specific aspect L is a covalent bond.

In one aspect of this embodiment, the invention provides a pharmaceutical composition comprising a pharmaceutically acceptable carrier and a compound of Formula I as defined above.

Furthermore, in one aspect of all the embodiments provided herein, the ring or ring system of R8 has at least one substituent chosen from the substituents described and defined in the respective embodiments.

In one aspect of all the embodiments provided herein, the ring or ring system of R8 has three substituents chosen from the substituents described and defined in the respective embodiments. For example, said three substituents may be independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido.

In one aspect of all the embodiments provided herein, R8 is aryl (such as, e.g., phenyl) or heterocyclyl (such as, e.g., pyridinyl, thiazolyl, or thiophenyl), wherein the ring or ring system of said aryl has 1-3 substituents (such as, e.g., 1 or 2 substituents) and further wherein the ring or ring system of said heterocyclyl has from 0-3 substituents (such as, e.g., 1 or 2 substituents), said substituents being independently chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido. In a more specific aspect, said substituents are independently chosen from hydroxyl, halo, alkyl, alkoxy, cycloalkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$alkyl), —S(=O)$_2$NH$_2$, —S(O)$_2$N($C_{1-3}$ alkyl)$_2$, —S(=O)$_2$NH($C_{1-3}$ alkyl), —CHF$_2$, —OCF$_3$, —OCHF$_2$, —CF$_3$, —CN, —NH$_2$, and —NO$_2$. In an even more specific aspect, said substituents are independently chosen from halo, alkyl, alkoxy, cycloalkoxy, and cyano.

In one specific aspect of all the embodiments provided herein, one of R1-R5 is chosen from -L-aryl, -L-heterocyclyl, and -L-carbocyclyl. In a more specific aspect, one of R1-R5 is -L-aryl. In an even more specific aspect, one of R1-R5 is benzyloxy.

In a further aspect of all the embodiments provided herein, R3 is benzyloxy and each of R1, R2, R4 and R5 is hydro.

In one aspect of all the embodiments provided herein, a compound wherein R1 to R7 are hydro and R8 is unsubstituted phenyl is excluded.

In one preferred aspect of all the embodiments provided herein, when the ring or ring system of R8 is a heterocycyl said ring system is chosen from pyridyl, thiazolyl, thiophenyl, quiolinyl, indolyl, oxadiazolyl, 2,3-dihydrobenzofuranyl, benzo[d][1,3]dioxolyl, 2,3-dihydrobenzo[b][1,4]dioxinyl, 3,4-dihydro-2H-benzo[b][1,4]dioxepinyl, and chromanyl.

In one preferred aspect of all the embodiments provided herein, when the ring or ring system of R8 is a heteroaryl said ring system is chosen from pyridyl, thiazolyl, thiophenyl, quiolinyl, indolyl, and oxadiazolyl. In an even more preferred aspect R8 is pyridyl.

In one embodiment, the invention provides a compound of Formula I (or a pharmaceutically acceptable salt thereof), a pharmaceutical composition comprising a pharmaceutically acceptable carrier and a compound of Formula I (or a pharmaceutically acceptable salt thereof), and a compound of Formula I (or a pharmaceutically acceptable salt thereof) for use in treating or preventing cancer, wherein: R1 to R7 are hydro and R8 is phenyl having 1, 2 or 3 substituents chosen from hydroxyl, halo, alkyl, alkoxy, cycloalkoxy, haloalkyl, haloalkoxy, —N($C_{1-3}$ alkyl)$_2$, —NH($C_{1-3}$ alkyl), —C(=O)NH$_2$, —C(=O)NH($C_{1-3}$ alkyl), —C(=O)N($C_{1-3}$ alkyl)$_2$, —S(=O)$_2$($C_{1-3}$ alkyl), —S(=O)$_2$NH$_2$, —S(O)$_2$N($C_{1-3}$ alkyl)$_2$, —S(=O)$_2$NH($C_{1-3}$ alkyl), —CN, —NH$_2$, and —NO$_2$.

In one aspect of all the embodiments provided herein, the compound of Formula I is chosen from:
(trans)-N-(4-fluorobenzyl)-2-phenylcyclopropanamine;
(trans)-N-(4-fluorobenzyl)-2-phenylcyclopropanaminium;
4-(((trans)-2-phenylcyclopropylamino)methyl)benzonitrile;
(trans)-N-(4-cyanobenzyl)-2-phenylcyclopropanaminium;
(trans)-2-phenyl-N-(4-(trifluoromethyl)benzyl)cyclopropanamine;
(trans)-2-phenyl-N-(4-(trifluoromethyl)benzyl)cyclopropanaminium;
(trans)-2-phenyl-N-(pyridin-2-ylmethyl)cyclopropanamine;
(trans)-2-phenyl-N-(pyridin-3-ylmethyl)cyclopropanamine;
(trans)-2-phenyl-N-(pyridin-4-ylmethyl)cyclopropanamine;
(trans)-N-((6-methylpyridin-2-yl)methyl)-2-phenylcyclopropanamine;
(trans)-2-phenyl-N-(thiazol-2-ylmethyl)cyclopropanamine;
(trans)-2-phenyl-N-(thiophen-2-ylmethyl)cyclopropanamine;
(trans)-N-((3-bromothiophen-2-yl)methyl)-2-phenylcyclopropanamine;
(trans)-N-((4-bromothiophen-2-yl)methyl)-2-phenylcyclopropanamine;
(trans)-N-(3,4-dichlorobenzyl)-2-phenylcyclopropanamine;
(trans)-N-(3-fluorobenzyl)-2-phenylcyclopropanaminium;
(trans)-N-(2-fluorobenzyl)-2-phenylcyclopropanamine;
(trans)-2-phenyl-N-(quinolin-4-ylmethyl)cyclopropanamine;
(trans)-N-(3-methoxybenzyl)-2-phenylcyclopropanamine;
(trans)-2-phenyl-N-((6-(trifluoromethyl)pyridin-3-yl)methyl)cyclopropanamine;
(trans)-N-((6-chloropyridin-3-yl)methyl)-2-phenylcyclopropanamine;
(trans)-N-((4-methylpyridin-2-yl)methyl)-2-phenylcyclopropanamine;
(trans)-N-((6-methoxypyridin-2-yl)methyl)-2-phenylcyclopropanamine;
2-(((trans)-2-phenylcyclopropylamino)methyl)pyridin-3-ol;
(trans)-N-((6-bromopyridin-2-yl)methyl)-2-phenylcyclopropanamine;
4-(((trans)-2-(4-(benzyloxy)phenyl)cyclopropylamino)methyl)benzonitrile;
(trans)-N-(4-(benzyloxy)benzyl)-2-phenylcyclopropanamine;
(trans)-N-benzyl-2-(4-(benzyloxy)phenyl)cyclopropanamine;
(trans)-2-(4-(benzyloxy)phenyl)-N-(4-methoxybenzyl)cyclopropanamine;
(trans)-2-(4-(benzyloxy)phenyl)-N-(4-fluorobenzyl)cyclopropanamine; and
pharmaceutically acceptable salts thereof.

Accordingly, the invention provides a compound of Formula I chosen from the above compounds, in particular for use as a medicament and also for use in treating and/or preventing cancer.

In one aspect of all the embodiments provided herein, the compound of Formula I is chosen from:
(trans)-2-phenyl-N-(quinolin-2-ylmethyl)cyclopropanamine;
(trans)-2-phenyl-N-((5-(trifluoromethyl)pyridin-2-yl)methyl)cyclopropanamine;
(trans)-N-((3-fluoropyridin-2-yl)methyl)-2-phenylcyclopropanamine;
(trans)-2-phenyl-N-(quinolin-3-ylmethyl)cyclopropanamine;
(trans)-N-((6-methoxypyridin-3-yl)methyl)-2-phenylcyclopropanamine;
(trans)-N-((5-methoxypyridin-3-yl)methyl)-2-phenylcyclopropanamine;
(trans)-N-((2-methoxypyridin-3-yl)methyl)-2-phenylcyclopropanamine;
(trans)-N-((3H-indol-3-yl)methyl)-2-phenylcyclopropanamine;
3-(((trans)-2-phenylcyclopropylamino)methyl)benzonitrile;
(trans)-N-(2-methoxybenzyl)-2-phenylcyclopropanamine;
3-(((trans)-2-phenylcyclopropylamino)methyl)pyridin-2-amine
(trans)-N-((2-chloropyridin-3-yl)methyl)-2-phenylcyclopropanamine;
(trans)-N-(3,4-dimethoxybenzyl)-2-phenylcyclopropanamine;
(trans)-N-((2,3-dihydrobenzofuran-5-yl)methyl)-2-phenylcyclopropanamine;
(trans)-N-(benzo[d][1,3]dioxol-5-ylmethyl)-2-phenylcyclopropanamine;
(trans)-N-((2,3-dihydrobenzo[b][1,4]dioxin-6-yl)methyl)-2-phenylcyclopropanamine;
(trans)-N-(2,6-difluoro-4-methoxybenzyl)-2-phenylcyclopropanamine;
(trans)-2-phenyl-N-(4-(trifluoromethoxy)benzyl)cyclopropanamine;
(trans)-N-(5-fluoro-2-methoxybenzyl)-2-phenylcyclopropanamine;

(trans)-N-(2-fluoro-4-methoxybenzyl)-2-phenylcyclopropanamine;
(trans)-N-((4-methoxynaphthalen-1-yl)methyl)-2-phenylcyclopropanamine;
(trans)-N-(2-fluoro-6-methoxybenzyl)-2-phenylcyclopropanamine;
(trans)-N-((2-methoxynaphthalen-1-yl)methyl)-2-phenylcyclopropanamine;
(trans)-N-((4,7-dimethoxynaphthalen-1-yl)methyl)-2-phenylcyclopropanamine;
(trans)-N-(4-methoxy-3-methylbenzyl)-2-phenylcyclopropanamine;
(trans)-N-(3-chloro-4-methoxybenzyl)-2-phenylcyclopropanamine;
(trans)-N-(3-fluoro-4-methoxybenzyl)-2-phenylcyclopropanamine;
(trans)-N-(4-methoxy-2-methylbenzyl)-2-phenylcyclopropanamine;
(trans)-N-((3,4-dihydro-2H-benzo[b][1,4]dioxepin-6-yl)methyl)-2-phenylcyclopropanamine;
(trans)-N-((3,4-dihydro-2H-benzo[b][1,4]dioxepin-7-yl)methyl)-2-phenylcyclopropanamine;
(trans)-N-((2,2-dimethylchroman-6-yl)methyl)-2-phenylcyclopropanamine;
(trans)-N-(4-methoxy-2,3-dimethylbenzyl)-2-phenylcyclopropanamine;
(trans)-N-(4-methoxy-2,5-dimethylbenzyl)-2-phenylcyclopropanamine;
(trans)-N-(2-fluoro-4,5-dimethoxybenzyl)-2-phenylcyclopropanamine;
(trans)-N-(3-chloro-4,5-dimethoxybenzyl)-2-phenylcyclopropanamine;
(trans)-N-(2-chloro-3,4-dimethoxybenzyl)-2-phenylcyclopropanamine;
(trans)-N-(2,4-dimethoxy-6-methylbenzyl)-2-phenylcyclopropanamine;
(trans)-N-(2,5-dimethoxybenzyl)-2-phenylcyclopropanamine;
(trans)-N-(2,3-dimethoxybenzyl)-2-phenylcyclopropanamine;
(trans)-N-(2-chloro-3-methoxybenzyl)-2-phenylcyclopropanamine;
(trans)-N-((1H-indol-5-yl)methyl)-2-phenylcyclopropanamine;
(trans)-2-(4-(benzyloxy)phenyl)-N-(pyridin-2-ylmethyl)cyclopropanamine;
(trans)-2-(4-(benzyloxy)phenyl)-N-(2-methoxybenzyl)cyclopropanamine;
(trans)-N-(1-(4-methoxyphenyl)ethyl)-2-phenylcyclopropanamine;
(trans)-N-(1-(3,4-dimethoxyphenyl)ethyl)-2-phenylcyclopropanamine;
(trans)-N-(1-(2,3-dihydrobenzo[b][1,4]dioxin-6-yl)ethyl)-2-phenylcyclopropanamine;
(trans)-N-(1-(5-fluoro-2-methoxyphenyl)ethyl)-2-phenylcyclopropanamine;
(trans)-N-(1-(3,4-dimethoxyphenyl)propan-2-yl)-2-phenylcyclopropanamine;
(trans)-N-((3-methyl-1,2,4-oxadiazol-5-yl)methyl)-2-phenylcyclopropanamine; and
pharmaceutically acceptable salts thereof.

Accordingly, the invention provides a compound of Formula I chosen from the above compounds, in particular for use as a medicament and also for use in treating and/or preventing cancer.

The invention provides compounds of Formula I which are selective inhibitors of LSD1. LSD1 selective inhibitors have IC50 values for LSD1 which are at least 2-fold lower than the IC50 value for MAO-A and/or MAO-B. In some embodiments, the LSD1 selective inhibitors have IC50 values which are at least 5-fold lower for LSD1 as compared to MAO-A and MAO-B. In some embodiments, the LSD1 selective inhibitors have IC50 values which are at least 10-fold lower for LSD1 as compared to MAO-A and MAO-B.

The invention also provides compounds of Formula I which are dual inhibitors selective for LSD1 and MAO-B. Dual LSD1/MAO-B selective inhibitors have IC50 values for LSD1 and MAO-B which are at least 2-fold lower than the IC50 value for MAO-A. In some embodiments, the dual LSD1/MAO-B selective inhibitors have IC50 values which are at least 5-fold lower for LSD1 and MAO-B as compared to MAO-A. In some embodiments, the dual LSD1/MAO-B selective inhibitors have IC50 values which are at least 10-fold lower for LSD1 and MAO-B as compared to MAO-A. In one aspect of this embodiment, the LSD1/MAO-B inhibitor avoids the deleterious side-effects associated with inhibition of MAO-A.

In one embodiment, the invention provides a method of treating a cancer comprising administering, to a patient in need of treatment, a therapeutically effective amount of a composition comprising a compound of Formula I and a pharmaceutically acceptable carrier. In a related embodiment, the invention provides a compound of Formula I for treating and/or preventing cancer. In another related embodiment, the invention provides for the use of a compound of Formula I for the manufacture of a medicament for treating and/or preventing cancer.

Previous reports of LSD1 have found that it is involved in cell proliferation and growth. Some studies have implicated LSD1 as a therapeutic target for cancer. Huang et al. (2007) *PNAS* 104:8023-8028 found that polyamines inhibitors of LSD1 modestly cause the reexpression of genes aberrantly silenced in cancer cells and particularly colorectal cancer (Huang et al. *Clin Cancer Res.* (2009) December 1; 15(23): 7217-28. Epub 2009 Nov. 24. PMID: 19934284). Scoumanne et al. ((2007) *J. Biol. Chem.* May 25; 282(21):15471-5) found that deficiency in LSD1 leads to a partial cell cycle arrest in G2/M and sensitizes cells to growth suppression induced by DNA damage. Kahl et al. ((2006) *Cancer Res.* 66(23):11341-7) found that LSD1 expression is correlated with prostate cancer aggressiveness. Metzger et al. reported that LSD1 modulation by siRNA and pargyline regulates androgen receptor (AR) and may have therapeutic potential in cancers where AR plays a role, like prostate, testis, and brain cancers. Lee et al. ((2006) *Chem. Biol.* 13:563-567) reported that tranylcypromine derepresses Egr-1 gene expression in some cancer lines. A body of evidence is accumulating that Egr-1 is a tumor suppressor gene in many contexts (see e.g., Calogero et al. (2004) *Cancer Cell International* 4:1 exogenous expression of EGR-1 resulted in growth arrest and eventual cell death in primary cancer cell lines; Lucerna et al. (2006) *Cancer Research* 66, 6708-6713 show that sustained expression of Egr-1 causes antiangiogenic effects and inhibits tumor growth in some models; Ferraro et al. ((2005) *J. Clin. Oncol.* March 20; 23(9):1921-6) reported that Egr-1 is downregulated in lung cancer patients with a higher risk of recurrence and may be more resistant to therapy. Thus, increasing Egr-1 expression via inhibition of LSD1 is a therapeutic approach for some cancers. Recent studies have also implicated LSD1 in brain cancer (Schulte et al. (2009) Cancer Res. March 1; 69(5):2065-71). Other studies have implicated LSD1 in breast cancer (Lims et al. Carcinogenesis. 2009 Dec. 30. [Epub ahead of print] PMID: 20042638).

Thus, a body of evidence has implicated LSD1 in a number of cancers, which suggests that LSD1 is a therapeutic target for cancer. The instant inventors have discovered a class of LSD1 inhibitors that can be used to treat diseases where LSD1 is implicated as a therapeutic target like cancer. Accordingly, the phenylcyclopropylamine compounds of the invention can be used to treat and/or prevent such diseases.

As the skilled artisan readily recognizes the compounds disclosed herein are surprisingly and significantly more potent than tranylcypromine for LSD1 inhibition. Han et al. (Euro. J. Pharma. (2008) doi:10.1016/j.ejphar.2008.12.025) reported that phenylcyclopropylamine displays neuroprotective activity in PC12 cells thus the compounds of Formula I may be used as a neuroprotectant (e.g., used to treat and/or prevent conditions characterized by neurodegeneration). Furthermore, since the compounds of Formula I are potent LSD1 inhibitor they can be used to treat and/or prevent diseases where LSD1 inhibition is desirable, e.g., cancer.

Without being bound by theory, it is believed that compounds provided herein are particularly useful in the treatment and/or prevention of cancer because they interfere with LSD1 activity (i.e. inhibit LSD1 activity), wherein LSD1 activity is part of a metabolic mechanism specifically involved in cancer as described elsewhere herein. Potent LSD1 inhibitors to be used in the treatment of cancer are shown in Table 1, wherein compounds with a low IC50 value (in particular compounds having a lower IC50 value than the prior art compound parnate) are preferred.

Furthermore, and without being bound by theory, dual MAO-B/LSD1 inhibitors provided herein are thought of interfering with a mechanism involved in neurodegenerative diseases. Accordingly, compounds that potently inhibit both MAO-B and LSD1 activity are preferred in the treatment of neurodegenerative diseases. Exemplary compounds in this context are shown in Table 1, wherein compounds with a low IC50 value (in particular compounds having a lower IC50 value than the prior art compound parnate) are preferred.

Also compounds that inhibit both MAO A/B activity and LSD1 activity are envisaged herein in the treatment of diseases, in particular neurodegenerative diseases, wherein compounds that inhibit LSD1 activity more potently than parnate are preferred.

In one embodiment, the invention provides a method of inhibiting LSD1 activity comprising administering, to a patient in need of treatment, an amount of a composition comprising a compound of Formula I and a pharmaceutically acceptable carrier sufficient to inhibit LSD1 activity. In a related embodiment, the invention provides a compound of Formula I for inhibiting LSD1. In another related embodiment, the invention provides for the use of a compound of Formula I for the manufacture of a medicament for inhibiting LSD1.

In one embodiment, the invention provides a method of treating a neurodegenerative disease or disorder comprising administering, to a patient in need of treatment, a therapeutically effective amount of a composition comprising a compound of Formula I and a pharmaceutically acceptable carrier. In a related embodiment, the invention provides a compound of Formula I for treating and/or preventing a neurodegenerative disease. In another related embodiment, the invention provides for the use of a compound of Formula I for the manufacture of a medicament for treating and/or preventing a neurodegenerative disease.

In one embodiment, the invention provides a method of inhibiting monoamine oxidase activity comprising administering, to a patient in need of treatment, an amount of a composition comprising a compound of Formula I and a pharmaceutically acceptable carrier sufficient to inhibit monoamine oxidase activity. In a related embodiment, the invention provides a compound of Formula I for treating and/or preventing Parkinson's disease and/or depression. In another related embodiment, the invention provides for the use of a compound of Formula I for the manufacture of a medicament for inhibiting monoamine oxidase. In a related embodiment, the invention provides a compound of Formula I for treating and/or preventing neurogeneration.

In some of the embodiments related to Formula I, the compound does not have the structure of the compounds having CAS registration nos. 22783-31-9, 1041848-33-2, 903487-42-3, 53578-57-7, 53578-56-6, 53578-54-4, 53578-53-3, 53578-52-2, 53578-50-0, 39933-77-2, 32752-01-5, and/or 22783-27-3.

In one embodiment, the invention provides a method of treating a disease or condition comprising administering, to a patient in need of treatment, a therapeutically effective amount of a composition comprising a compound of Formula I and a pharmaceutically acceptable carrier. In one aspect of this embodiment, the disease is cancer or a neurodegenerative disease.

In one embodiment, the invention provides a method of treating a cancer comprising administering, to a patient in need of treatment, a therapeutically effective amount of a composition comprising a compound of Formula I and a pharmaceutically acceptable carrier. In one aspect of this embodiment, the cancer is prostate cancer. In another specific aspect of this embodiment, the cancer is brain cancer. In yet another specific aspect of this embodiment, the cancer is breast cancer. In yet another specific aspect of this embodiment, the cancer is lung cancer. In yet another specific aspect of this embodiment, the cancer is testicular cancer. In yet another specific aspect of this embodiment, the cancer is colorectal cancer. In yet another specific aspect of this embodiment, the cancer is blood cancer (e.g., leukemia). In yet another specific aspect of this embodiment, the cancer is skin cancer.

In one embodiment, the invention provides a method of treating a neurodegenerative disease or disorder comprising administering, to a patient in need of treatment, a therapeutically effective amount of a composition comprising a compound of Formula I and a pharmaceutically acceptable carrier.

In one embodiment, the invention provides a method for identifying LSD1 selective inhibitors comprising determining the ability of a test compound to inhibit LSD1 and monoamine oxidase (MAO-A and/or MAO-B) wherein a test compound that inhibits LSD1 better than monoamine oxidase (MAO-A and/or MAO-B) is LSD1 selective. In one aspect of this embodiment, the selective inhibitor has an IC50 value at least two-fold lower for LSD1 as compared to MAO-A and MAO-B. In one aspect of this embodiment, the LSD1 selective inhibitor has an IC50 value at least five-fold lower for LSD1 as compared to MAO-A and MAO-B. In one aspect of this embodiment, the LSD1 selective inhibitor has an IC50 value at least ten-fold lower for LSD1 as compared to MAO-A and MAO-B. In one aspect of this embodiment, the test compound is chosen from a phenylcyclopropylamine derivative, homolog or analog. In one specific aspect of this embodiment the phenylcyclopropylamine analog has the phenyl group replaced with another ring system (e.g., aryl, heterocyclyl and/or heteroaryl which is optionally substituted) and the amine group is substituted with a functional group (see e.g., examples). In another aspect, the test compound is a phenylcyclopropylamine analog or derivative where the amine group is substituted with a functional group.

In another aspect, the test compound is a phenylcyclopropylamine analog or derivative where the amine group is substituted with a functional group and the phenyl group has at least one substituent that is not a hydrogen atom. In a related embodiment, the invention provides a method of inhibiting LSD1 selectively as compared to MAO-B and MAO-A comprising administering to an individual a phenylcyclopropylamine derivative, homolog, or analog that selectively inhibits LSD1. In a related embodiment, the invention provides a method of inhibiting LSD1 selectively as compared to MAO-B and MAO-A comprising administering to an individual a compound of Formula I as defined in the embodiments described in this invention, that selectively inhibits LSD1.

In one embodiment, the invention provides a method for identifying a dual inhibitor selective for LSD1/MAO-B as compared to MAO-A comprising determining the ability of a test compound to inhibit LSD1 and monoamine oxidase (MAO-A and MAO-B) wherein a test compound that inhibits LSD1 and MAO-B better than LSD1 and monoamine oxidase (MAO-A and/or MAO-B) is a dual LSD1/MAO-B selective inhibitor. In one aspect of this embodiment, the dual LSD1/MAO-B selective inhibitor has an IC50 value at-least two-fold lower for LSD1 and MAO-B as compared to MAO-A. In one aspect of this embodiment, the dual LSD1/MAO-B selective inhibitor has an IC50 value at-least five-fold lower for LSD1 and MAO-B. In one aspect of this embodiment, the dual LSD1/MAO-B selective inhibitor has an IC50 value at-least ten-fold lower for LSD1 and MAO-B as compared to MAO-A.

In one aspect of this embodiment, the test compound is chosen from a phenylcyclopropylamine derivative, homolog or analog. In one specific aspect of this embodiment the phenylcyclopropylamine analog has the phenyl group replaced with another ring system (e.g., aryl, heterocyclyl and/or heteroaryl which is optionally substituted) and the amine group is substituted with a functional group (see e.g., examples). In another aspect, the test compound is a phenylcyclopropylamine analog or derivative where the amine group is substituted with a functional group. In another aspect, the test compound is a phenylcyclopropylamine analog or derivative where the amine group is substituted with a functional group and the phenyl group has at-least one substituent that is not a hydrogen. In a related embodiment, the invention provides a method of inhibiting LSD1 and MAO-B selectively as compared to MAO-A comprising administering to an individual a phenylcyclopropylamine derivative, homolog, or analog that selectively inhibits LSD1 and MAO-B. In a related embodiment, the invention provides a method of inhibiting LSD1 and MAO-B selectively as compared to MAO-A comprising administering to an individual a compound of Formula I as defined in the embodiments described in this invention, and that selectively inhibits LSD1 and MAO-B.

Phenylcyclopropylamine derivatives, homologs, and analogs can be made by methods known in the art e.g., including, but not limited to the methods disclosed herein and in the references cited herein. See for example, Kaiser et al. (1962) J. Med. Chem. 5:1243-1265 and Zirkle et al. (1962) J. Med. Chem. 1265-1284 Yoshida et al. (2004) Bioorg. Med Chem. 12(10):2645-2652; Hruschka et al. (2008) Biorg Med Chem. (16):7148-7166; and Gooden et al. (2008) Bioorg. Med. Chem. Let. 18:3047-3051 which describe various phenylcyclopropropylamine analogs, derivatives and homologs. The amine groups of these compounds can be alkylated as described in the examples to give substituted phenylcyclopropylamine derivative, analogs, and homologs.

Thus, in a specific embodiment, the invention provides a method of identifying LSD1 selective and LSD1/MAO-B inhibitors comprising determining the ability of a test compound to inhibit LSD1, MAO-A, and MAO-B wherein a LSD1 selective inhibitor is identified when the test compound inhibits LSD1 to a greater extent than MAO-A and MAO-B and wherein a LSD1/MAO-B dual inhibitor is identified when the test compound inhibits LSD1 and MAO-B to a greater extent than it inhibits MAO-A wherein said test compound is compound of Formula I:

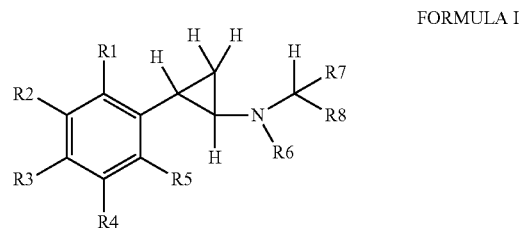

FORMULA I wherein:
each of R1-R5 is independently chosen from —H, halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
R6 is chosen from —H and alkyl;
R7 is chosen from —H, alkyl, and cycloalkyl;
R8 is -L-heterocyclyl or -L-aryl, wherein the ring or ring system of said -L-heterocyclyl or -L-aryl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
each L is independently chosen from —$(CH_2)_n$—$(CH_2)_n$—, —$(CH_2)_nNH(CH_2)_n$—, —$(CH_2)_nO(CH_2)_n$—, and —$(CH_2)_nS(CH_2)_n$—, where each n is independently chosen from 0, 1, 2, and 3; or a compound of Formula I where the phenyl ring attached to the cyclopropylamine moiety is replaced by an optionally substituted heteroaryl group and the other variables R6-R8 as defined above.

Compounds that are identified as LSD1 selective and LSD1/MAO-B dual inhibitors can be used to prepare pharmaceutical compositions for treating diseases according to the methods of the invention as described herein. Preferably the diseases can be treated by inhibiting LSD1, LSD1 and MAO-B, and/or by modulating histone methylation levels.

In a specific aspect of this embodiment, the invention provides a method of identifying LSD1 selective and LSD1/MAO-B dual inhibitors comprising determining the ability of a test compound to inhibit LSD1, MAO-A, and MAO-B wherein a LSD1 selective inhibitor is identified when the test compound inhibits LSD1 to a greater extent than MAO-A and MAO-B and wherein a LSD1/MAO-B dual inhibitor is identified when the test compound inhibits LSD1 and MAO-B to a greater extent than it inhibits MAO-A wherein said test compound is compound of Formula I:

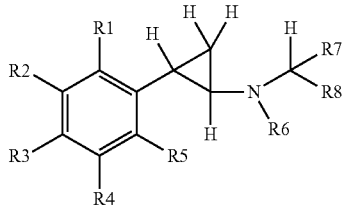

FORMULA I wherein:
each of R1-R5 is independently chosen from —H, halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
R6 is chosen from —H and alkyl;
R7 is chosen from —H, alkyl, and cycloalkyl;
R8 is a -L-heterocyclyl wherein the ring or ring system of said -L-heterocyclyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido; or
R8 is -L-aryl wherein the ring or ring system of said -L-aryl has from 1-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;
each L is independently chosen from —$(CH_2)_n$—$(CH_2)_n$—, —$(CH_2)_n NH(CH_2)_n$—, —$(CH_2)_n O(CH_2)_n$—, and —$(CH_2)_n S(CH_2)_a$—, where each n is independently chosen from 0, 1, 2, and 3;
or a compound of Formula I where the phenyl ring attached to the cyclopropylamine moiety is replaced by an optionally substituted heteroaryl group and the other variables R6-R8 are as defined above.

As used herein, the term "alkyl" refers to a saturated aliphatic hydrocarbon including straight chain and/or branched chain groups. In a more specific definition, the alkyl group is further defined as having 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc. up to and including 20 carbon atoms). In another more specific definition, it is an alkyl having 1 to 10 carbon atoms. In yet another more specific definition, it is an alkyl having 1 to 6 carbon atoms, and in yet another more specific definition, it is an alkyl having 1 to 4 carbon atoms.

As used herein, the term "alkenyl" refers to an unsaturated hydrocarbon including straight chain and/or branched chain groups, comprising at least one carbon-to-carbon double bond. In a more specific definition, the alkenyl group is further defined as having 2 to 20 carbon atoms. In another more specific definition, it is an alkenyl having 2 to 10 carbon atoms. In yet another more specific definition, it is an alkenyl having 2 to 6 carbon atoms, and in yet another more specific definition, it is an alkenyl having 2 to 4 carbon atoms.

As used herein, the term "alkynyl" refers to an unsaturated hydrocarbon including straight chain and/or branched chain groups, comprising at least one carbon-to-carbon triple bond. In a more specific definition, the alkynyl group is further defined as having 2 to 20 carbon atoms. In another more specific definition, it is an alkynyl having 2 to 10 carbon atoms. In yet another more specific definition, it is an alkynyl having 2 to 6 carbon atoms, and in yet another more specific definition, it is an alkynyl having 2 to 4 carbon atoms.

As used herein, the term "halo" refers to a group chosen from chloro, fluoro, bromo, and iodo.

As used herein, the term "hydro" refers to a hydrogen atom (—H group) which is also denoted as —H.

As used herein, the term "hydroxyl" refers to an —OH group.

As used herein, the term "alkoxy" refers to an —O-alkyl group, wherein the alkyl group is as defined herein above.

As used herein, the term "cycloalkoxy" refers to an —O-cycloalkyl group, wherein the cycloalkyl group is as defined herein below.

As used herein, the term "aryloxy" refers to an —O-aryl group, wherein the aryl group is as defined herein below.

As used herein, the term "heteroaryloxy" refers to an —O-heteroaryl group, wherein the heteroaryl group is as defined herein below.

As used herein, the term "mercapto" refers to an —SH group.

As used herein, the term "alkylthio" refers to an —S-alkyl group, wherein the alkyl group is as defined herein above.

As used herein, the term "cycloalkylthio" refers to an —S-cycloalkyl group, wherein the cycloalkyl group is as defined herein below.

As used herein, the term "arylthio" refers to an —S-aryl group, wherein the aryl group is as defined herein below.

As used herein, the term "heteroarylthio" refers to an —S-heteroaryl group, wherein the heteroaryl group is as defined herein below.

As used herein, the term "carbonyl" refers to a —C(=O)R" group, wherein R" is as defined herein below.

Unless specified otherwise, R" is selected from the group consisting of hydro, alkyl, cycloalkyl, aryl, heteroaryl (bonded through a ring carbon atom) and heterocyclyl (bonded through a ring carbon atom), wherein said hydro, alkyl, cycloalkyl, aryl, heteroaryl and heterocyclyl are as defined herein.

As used herein, the term "aldehyde" group refers to a carbonyl group as defined herein above, wherein R" is hydro.

As used herein, the term "cycloketone" group refers to a cycloalkyl group as defined herein below, wherein one of the carbon atoms which form the ring has an "=O" bonded to it, i.e., one of the ring carbon atoms of the cycloalkyl group is a —C(=O)— group.

As used herein, the term "thiocarbonyl" refers to a —C(=S)R" group, wherein R" is as defined herein above.

As used herein, the term "O-carboxy" refers to an —OC(=O)R" group, wherein R" is as defined herein above.

As used herein, the term "C-carboxy" refers to a —C(=O)OR" group, wherein R" is as defined herein above.

As used herein, the term "ester" refers to a C-carboxy group as defined herein above or a molecule comprising such group, wherein R" is as defined herein above and R" is not hydro.

As used herein, the term "C-carboxy salt" refers to a —C(=O)O$^-$M$^+$ group or a molecule comprising such group, wherein M$^+$ is selected from the group consisting of lithium, sodium, magnesium, calcium, potassium, barium, iron, zinc and quaternary ammonium, and further wherein the "+" in M$^+$ does not reflect the actual number of positive charges which depends on the respective ion.

As used herein, the term "acetyl" refers to a —C(=O)CH$_3$ group.

As used herein, the term "carboxyalkyl" refers to a —(CH$_2$)$_r$C(=O)OR" group, wherein r is 1 to 6 and R" is as defined herein above.

As used herein, the term "carboxyalkyl salt" refers to a —(CH$_2$)$_r$C(=O)O$^-$M$^+$ group or a molecule comprising such group, wherein r is 1 to 6 and M$^+$ is selected from the group consisting of lithium, sodium, potassium, calcium, magnesium, barium, iron, zinc and quaternary ammonium, and further wherein the "+" in M$^+$ does not reflect the actual number of positive charges which depends on the respective ion.

As used herein, the term "carboxylic acid" refers to a C-carboxy group as defined herein above, wherein R" is hydro.

As used herein, the term "haloalkyl" refers to an alkyl group substituted with 1 to 6 halo groups, wherein the alkyl group and the halo groups are as defined herein above, and further wherein the halo groups are independently selected. In a more specific definition, haloalkyl is a —CX$_3$ group, wherein each X independently is a halo group.

As used herein, the term "trihalomethanesulfonyl" refers to an —S(=O)$_2$CX$_3$ group, wherein each X is a halo group as defined herein above.

As used herein, the term "cyano" refers to a —C≡N group.

As used herein, the term "cyanato" refers to an —OCN group.

As used herein, the term "isocyanato" refers to an —NCO group.

As used herein, the term "thiocyanato" refers to an —SCN group.

As used herein, the term "isothiocyanato" refers to an —NCS group.

As used herein, the term "sulfinyl" refers to an —S(=O)R" group, wherein R" is as defined herein above.

As used herein, the term "sulfonyl" refers to an —S(=O)$_2$R" group, wherein R" is as defined herein above.

As used herein, the term "sulfonamido" refers to an —S(=O)$_2$NR$_{17}$R$_{18}$ group, wherein R$_{17}$ and R$_{18}$ are as defined herein below.

Unless specified otherwise, R$_{17}$ and R$_{18}$ are independently chosen from hydro, alkyl, aryl, carbocyclyl, heterocyclyl, —(CH$_2$)aryl, —(CH$_2$)carbocyclyl, and —(CH$_2$)heterocyclyl, wherein hydro, alkyl, aryl, carbocyclyl and heterocyclyl are as defined herein.

As used herein, the term "trihalomethanesulfonamido" refers to an —N(R$_{17}$)S(=O)$_2$CX$_3$ group, wherein X is a halo group as defined herein above and R$_{17}$ is as defined as herein above.

As used herein, the term "O-carbamyl" refers to an —OC(=O)NR$_{17}$R$_{18}$ group, wherein R$_{17}$ and R$_{18}$ are as defined herein above.

As used herein, the term "N-carbamyl" refers to an —N(R$_{17}$)C(=O)OR$_{18}$ group, wherein R$_{17}$ and R$_{18}$ are as defined herein above.

As used herein, the term "O-thiocarbamyl" refers to an —OC(=S)NR$_{17}$R$_{18}$ group, wherein R$_{17}$ and R$_{18}$ are as defined herein above.

As used herein, the term "N-thiocarbamyl" refers to an —N(R$_{17}$)C(=S)OR$_{18}$ group, wherein R$_{17}$ and R$_{18}$ are as defined herein above.

As used herein, the term "amino" refers to an —NH$_2$ group.

As used herein, the term "alkylamino" refers to an —NR$_{23}$R$_{24}$ group, wherein R$_{23}$ and R$_{24}$ are independently chosen from —H, C$_{1-8}$ alkyl (i.e., an alkyl having 1 to 8 carbon atoms), and phenyl.

As used herein, the term "C-amido" refers to a —C(=O)NR$_{17}$R$_{18}$ group, wherein R$_{17}$ and R$_{18}$ are as defined herein above.

As used herein, the term "N-amido" refers to an —N(R$_{17}$)C(=O)R$_{18}$ group, wherein R$_{17}$ and R$_{18}$ are as defined herein above.

As used herein, the term "nitro" refers to an —NO$_2$ group.

As used herein, the term "quaternary ammonium" refers to an —NR$_{20}$R$_{21}$R$_{22}$ group, wherein R$_{20}$, R$_{21}$, and R$_{22}$ are independently selected from the group consisting of hydro and C$_{1-6}$ alkyl.

As used herein, the term "methylenedioxy" refers to an —OCH$_2$O— group, wherein the two oxygen atoms are bonded to adjacent ring carbon atoms.

As used herein, the term "ethylenedioxy" refers to an —OCH$_2$CH$_2$O— group, wherein the two oxygen atoms are bonded to adjacent ring carbon atoms.

As used herein, the term "carbocyclyl" refers to an all-carbon monocyclic or fused ring (i.e., rings which share an adjacent pair of ring carbon atoms) group, wherein one or more of the rings does not have a completely conjugated pi-electron system. In a more specific definition, it refers to a cycloalkyl group having 3 to 12 carbon atoms or a cycloalkenyl group having 3 to 12 carbon atoms. In another more specific definition, it refers to a cycloalkyl group having 3 to 6 carbon atoms or a cycloalkenyl group having 3 to 6 carbon atoms. Examples, without limitation, of carbocyclyl groups are cycloalkyls such as cyclopropane, cyclobutane, cyclopentane, cyclohexane, adamantane, cycloheptane and cycloalkenes such as cycloheptatriene, cyclopentene, and cyclohexadiene.

As used herein, the term "cycloalkyl" refers to an all-carbon monocyclic or fused ring (i.e., rings which share an adjacent pair of ring carbon atoms) group, wherein said monocyclic or fused ring group does not have a double or triple bond. In a more specific definition, it refers to a C$_{3-12}$ cycloalkyl group, i.e., an all-carbon monocyclic or fused ring group having 3 to 12 carbon atoms, wherein said monocyclic or fused ring group does not have a double or triple bond. In another more specific definition, it refers to a C$_{3-6}$ cycloalkyl group, i.e., an all-carbon monocyclic or fused ring group having 3 to 6 carbon atoms, wherein said monocyclic or fused ring group does not have a double or triple bond. Examples, without limitation, of cycloalkyl groups are cyclopropane, cyclobutane, cyclopentane, cyclohexane, adamantane, and cycloheptane.

As used herein, the term "heterocyclyl" (or "heterocycle" or "heterocyclic") refers to a saturated or partially saturated monocyclic or fused-ring polycyclic group having 3 to 14 ring atoms, said ring atoms comprising carbon atoms and from one to four heteroatoms independently selected from the group consisting of O, N, and S, wherein the nitrogen and sulfur heteroatoms can be optionally oxidized, the nitrogen heteroatoms can be optionally quaternized, and including any bicyclic group in which any of the above-defined heterocyclic rings is fused to a benzene ring. "Heterocyclyl" thus also include heteroaryl groups as defined herein below. In a more specific definition, "heterocyclyl" refers to a saturated or partially saturated 3-7 membered monocyclic, or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen heteroatoms can be optionally quaternized, and including any bicyclic group in which any of the above-defined heterocyclic rings is fused to a benzene ring. Non-limiting examples of saturated or partially saturated heterocyclyl groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups. Examples of "heterocycles" or "heterocyclic" rings also include, but are not limited to, morpholino, piperidyl, piperazinyl, pyrrolidinyl, thiomorpholino, homopiperazinyl, imidazolyl, imidazolidinyl, pyrazolidinyl, dioxanyl and dioxolanyl.

As used herein, the term "aryl" refers to an all-carbon monocyclic or fused-ring polycyclic (i.e., rings which share an adjacent pair of ring carbon atoms) aromatic group having a completely conjugated pi-electron system. Examples, without limitation, of aryl groups are phenyl, naphthalenyl and anthracenyl.

As used herein, the term "heteroaryl" refers to a monocyclic or fused-ring polycyclic group having 5 to 14 ring atoms; having 6, 10 or 14 pi electrons shared in a cyclic array; and containing carbon atoms and 1, 2 or 3 heteroatoms independently selected from the group consisting of O, N, and S. In a more specific definition, it refers to a monocyclic or fused-ring polycyclic aromatic group having 5 to 9 ring atoms and comprising 1, 2 or 3 heteroatoms independently selected from the group consisting of O, N, and S, Non-limiting examples of heteroaryl groups include thienyl (thiophenyl), benzo[b]thienyl, naphtho[2,3-b]thienyl, thianthrenyl, furyl(furanyl), isobenzofuranyl, chromenyl, xanthenyl, phenoxathiinyl, pyrrolyl (including, without limitation, 2H-pyrrolyl), imidazolyl, pyrazolyl, pyridyl(pyridinyl; including, without limitation, 2-pyridyl, 3-pyridyl, and 4-pyridyl), pyrazinyl, pyrimidinyl, pyridazinyl, indolizinyl, isoindolyl, indolyl (including, without limitation, 3H-indolyl), indazolyl, purinyl, 4H-quinolizinyl, isoquinolyl, quinolyl, phthalzinyl, naphthyridinyl, quinozalinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, pyrazolo[1,5-a]pyrimidinyl (including, without limitation, pyrazolo[1,5-a]pyrimidin-3-yl), 1,2-benzoisoxazol-3-yl, benzimidazolyl, 2-oxindolyl and 2-oxobenzimidazolyl. When the heteroaryl group contains a nitrogen ring atom, such nitrogen atom may optionally be in the form of an N-oxide, e.g., a pyridyl N-oxide, pyrazinyl N-oxide and pyrimidinyl N-oxide.

As used herein and unless specified otherwise, the term "optional substituent" or "optionally substituted" refers to one or more substituents covalently linked to the parent group, wherein said substituents are independently chosen from halo, alkyl, alkynyl, alkenyl, alkoxy, cycloalkoxy, haloalkyl, haloalkoxy, -L-carbocyclyl, -L-aryl, -L-heteroaryl, -L-heterocyclyl, acylamino, acyloxy, alkylthio, cycloalkylthio, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido, wherein each L is independently chosen from $-(CH_2)_n-(CH_2)_n-$, $-(CH_2)_nNH(CH_2)_n-$, $-(CH_2)_nO(CH_2)_n-$, and $-(CH_2)_nS(CH_2)_n-$, and wherein each n is independently chosen from 0, 1, 2, and 3. In an alternative definition, the one or more optional substituents are chosen from hydroxyl, halo, alkyl, alkoxy, cycloalkoxy, haloalkyl, haloalkoxy, $-N(C_{1-3}$ alkyl$)_2$, $-NH(C_{1-3}$ alkyl), $-NHC(=O)(C_{1-3}$ alkyl), $-C(=O)OH$, $-C(=O)O(C_{1-6}$ alkyl), $-C(=O)(C_{1-3}$ alkyl), $-C(=O)NH_2$, $-C(=O)NH(C_{1-3}$ alkyl), $-C(=O)NH$(cycloalkyl), $-C(=O)N(C_{1-3}$ alkyl$)_2$, $-S(=O)_2(C_{1-3}$ alkyl), $-S(=O)_2NH_2$, $-S(=O)_2N(C_{1-3}$ alkyl$)_2$, $-S(=O)_2NH(C_{1-3}$ alkyl), $-CHF_2$, $-OCF_3$, $-OCHF_2$, $-CF_3$, $-CN$, $-NH_2$, $-NO_2$, and tetrazolyl.

As used herein, the term "arylalkyl" refers to a $C_{1-10}$ alkyl group (an alkyl group having 1-10 carbon atoms), as defined herein above, substituted by a $C_{6-14}$ aryl group (an aryl group having 6 to 14 carbon atoms), as defined herein above. Non-limiting examples of arylalkyl groups include benzyl, phenethyl, and naphthylmethyl.

As used herein, the term "arylalkenyl" refers to a $C_{2-10}$ alkenyl group substituted by a $C_{6-14}$ aryl group (an aryl group having 6 to 14 carbon atoms), as defined herein above.

As used herein, the term "arylalkynyl" refers to a $C_{2-10}$ alkynyl group substituted by a $C_{6-14}$ aryl group (an aryl group having 6 to 14 carbon atoms), as defined herein above.

As used herein, the term "arylalkoxy" refers to a $C_{1-10}$ alkoxy group, as defined herein above, substituted by an aryl group, as defined herein above. Examples of arylalkoxy groups include benzyloxy and phenethyloxy.

As used herein, the term "aryloxy" refers to an oxygen substituted by a $C_{6-14}$ aryl group, as defined herein above. Examples of aryloxy groups include phenoxy and 4-methylphenoxy.

As used herein, the term "arylthio" refers to an —S-aryl group, wherein the aryl group is as defined herein above.

As used herein, the term "heteroarylthio" refers to an —S-heteroaryl group, wherein the heteroaryl group is as defined herein above.

As used herein, the term "haloalkoxy" refers to an alkoxy group which is substituted with 1 to 6 halo groups, wherein the alkoxy group and the halo groups are as defined herein above, and further wherein the halo groups are independently selected.

As used herein, the term "haloaryl" refers to an aryl group which is substituted with 1 to 6 halo groups, wherein the aryl group and the halo groups are as defined herein above, and further wherein the halo groups are independently selected.

As used herein, the term "acylamino" refers to an $-N(R_{17})C(=O)R_{18}$ group, wherein $R_{17}$ and $R_{18}$ are as defined herein above.

As used herein, the term "acyloxy" refers to an $-O-C(=O)R_{17}$ group, wherein $R_{17}$ is as defined herein above.

As used herein, the term "heteroaryloxy" refers to an —O-heteroaryl group, wherein the heteroaryl group is as defined herein above.

As used herein, the term "heteroarylalkoxy" refers to a $C_{1-10}$ alkoxy group, as defined herein above, substituted by a heteroaryl group, as defined herein above.

As used herein, the term "preventing an increase in a symptom" refers to both not allowing a symptom to increase or worsen, as well as reducing the rate of increase in the symptom. For example, a symptom can be measured as the amount of particular disease marker, i.e., a protein. In another example the symptom can be cognitive decline. Preventing an increase, according to the definition provided herein, means that the amount of symptom {e.g., protein or cognitive decline) does not increase or that the rate at which it increases is reduced.

As used herein, the term "treating a disease or disorder" refers to a slowing of or a reversal of the progress of the disease. Treating a disease or disorder includes treating a symptom and/or reducing the symptoms of the disease.

As used herein, the term "preventing a disease or disorder" refers to a slowing of the disease or of the onset of the disease or the symptoms thereof. Preventing a disease or disorder can include stopping the onset of the disease or symptoms thereof. As used herein, the term "unit dosage form" refers to a physically discrete unit, such as a capsule or tablet suitable as a unitary dosage for a human patient. Each unit contains a predetermined quantity of a compound of Formula I, which was discovered or believed to produce the desired pharmacokinetic profile which yields the desired therapeutic effect. The dosage unit is composed of a compound of Formula I in association with at least one pharmaceutically acceptable carrier, salt, excipient, or combination thereof.

The patient or subject, such as the subject in need of treatment or prevention, may be e.g. a eukaryote, an animal, a vertebrate animal, a mammal, a rodent (e.g. a guinea pig, a hamster, a rat, a mouse), a murine (e.g. a mouse), a canine (e.g. a dog), a feline (e.g. a cat), an equine (e.g. a horse), a primate, a simian (e.g. a monkey or ape), a monkey (e.g. a marmoset, a baboon), an ape (e.g. gorilla, chimpanzee, orangutang, gibbon), or a human. The meaning of the terms "eukaryote", "animal", "mammal", etc. is well known in the art and can, for example, be deduced from Wehner and Gehring (1995; Thieme Verlag). In the context of this invention, it is particularly envisaged that animals are to be treated which are economically, agronomically or scientifically important. Scientifically important organisms include, but are not limited to, mice, rats, rabbits, fruit flies like *Drosophila melagonaster* and nematodes like *Caenorhabditis elegans*. Non-limiting examples of agronomically important animals are sheep, cattle and pig, while, for example, cats and dogs may be considered as economically important animals. Preferably, the subject/patient is a mammal; more preferably, the subject/patient is a human.

As used herein, the term "dose" or "dosage" refers the amount of active ingredient that an individual takes or is administered at one time. For example, a 40 mg dose of a compound of Formula I refers to, in the case of a twice-daily dosage regimen, a situation where the individual takes 40 mg of a compound of Formula I twice a day, e.g., 40 mg in the morning and 40 mg in the evening. The 40 mg of a compound of Formula I dose can be divided into two or more dosage units, e.g., two 20 mg dosage units of a compound of Formula I in tablet form or two 20 mg dosage units of a compound of Formula I in capsule form.

As used herein, a "pharmaceutically acceptable prodrug" is a compound that may be converted under physiological conditions or by solvolysis to the specified compound or to a pharmaceutically acceptable salt of such compound.

As used herein, a "pharmaceutically active metabolite" is intended to mean a pharmacologically active product produced through metabolism in the body of a specified compound or salt thereof. Metabolites of a compound may be identified using routine techniques known in the art and their activities determined using tests such as those described herein.

As used herein, a "pharmaceutically acceptable salt" is intended to mean a salt that retains the biological effectiveness of the free acids and bases of the specified compound and that is not biologically or otherwise undesirable. A compound for use in the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrophosphates, dihydrophosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methane-sulfonates, propanesulfonates, naphthalene-1-sulfonates, naphthalene-2-sulfonates, and mandelates.

As used herein, a "pharmaceutically acceptable carrier" refers to a non-API (API refers to Active Pharmaceutical Ingredient) substances such as disintegrators, binders, fillers, and lubricants used in formulating pharmaceutical products. They are generally safe for administering to humans according to established governmental standards, including those promulgated by the United States Food and Drug Administration and the European Medical Agency.

As is understood by the skilled artisan, certain variables in the list of substituents are repetitive (different name for the same substituent), generic to other terms in the list, and/or partially overlap in content with other terms. In the compounds of the invention, the skilled artisan recognizes that substituents may be attached to the remainder of the molecule via a number of positions and the preferred positions are as illustrated in the Examples.

Additionally, the compounds of Formula I can contain asymmetric carbon atoms and can therefore exist in racemic and optically active forms. Thus, optical isomers or enantiomers, racemates, tautomers, and diastereomers are also encompassed in the compounds of Formula I in all embodiments described herein. The methods of the present invention include the use of all such isomers and mixtures thereof. Methods of separation of enantiomeric and diastereomeric mixtures are well known to one skilled in the art. The present invention encompasses any isolated racemic or optically active form of compounds described in Formula I, or any mixture thereof. In one aspect, the compounds of the invention have a trans configuration around the cyclopropyl ring as in trans-phenylcyclopropylamine. In one aspect, the compounds of the invention have a cis configuration around the cyclopropyl ring as in cis-phenylcyclopropylamine.

Typically, compounds according to Formula I can be effective at an amount of from about 0.01 µg/kg to about 100 mg/kg per day based on total body weight. The active ingredient may be administered at once, or may be divided into a number of smaller doses to be administered at predetermined intervals of time. The suitable dosage unit for each administration can be, e.g., from about 1 µg to about 2000 mg, preferably from about 5 µg to about 1000 mg.

It should be understood that the dosage ranges set forth above are exemplary only and are not intended to limit the scope of this invention. The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can be adjusted as the various factors change over time.

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and antioxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al. (1988) Ann. Rev. Med. 39:221-229 which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al. (1984) J. Clin. Psych. 45:242-247. Hydrogels can be used as a carrier for the sustained release of the active compounds. Hydrogels are generally known in the art. They are typically made by crosslinking high molecular weight biocompatible polymers into a network, which swells in water to form a gel like material. Preferably, hydrogels are biodegradable or biosorbable. For purposes of this invention, hydrogels made of polyethylene glycols, collagen, or poly (glycolic-co-L-lactic acid) may be useful. See, e.g., Phillips et al. (1984) J. Pharmaceut. Sci., 73: 1718-1720.

The active compounds can also be conjugated, to a water soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally, Burnham (1994) Am. J. Hosp. Pharm. 15:210-218. PEGylated proteins are currently being used in protein replacement therapies and for other therapeutic uses. For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art. Other pharmaceutically acceptable prodrugs of the compounds of this invention include, but are not limited to, esters, carbonates, thiocarbonates, N-acyl derivatives, N-acyloxyalkyl derivatives, quaternary derivatives of tertiary amines, N-Mannich bases, Schiff bases, aminoacid conjugates, phosphate esters, metal salts and sulfonate esters.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., Methods in Cell Biology, Volume XIV, Academic Press, New York, N.Y. (1976).

The active compounds can also be administered in combination with another active agent that synergistically treats or prevents the same symptoms or is effective for another disease or symptom in the patient treated so long as the other active agent does not interfere with or adversely affect the effects of the active compounds of this invention. Such other active agents include but are not limited to anti-inflammation agents, antiviral agents, antibiotics, antifungal agents, antithrombotic agents, cardiovascular drugs, cholesterol lowering agents, anti-cancer drugs, hypertension drugs, and the like.

Examples of antineoplastic agents that can be used in combination with the compounds and methods of the present invention include, in general, and as appropriate, alkylating agents, anti-metabolites, epidophyllotoxins, antineoplastic enzymes, topoisomerase inhibitors, procarbazines, mitoxantrones, platinum coordination complexes, biological response modifiers and growth inhibitors, hormonal/anti-hormonal therapeutic agents and haematopoietic growth factors. Exemplary classes of antineoplastic include the anthracyclines, vinca drugs, mitomycins, bleomycins, cytotoxic nucleosides, epothilones, discodermolides, pteridines, diynenes and podophyllotoxins. Particularly useful members of those classes include, for example, caminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, carboplatin, cyclophosphamide, bleomycin, gemcitabine, ifosfamide, melphalan, hexamethyl melamine, thiotepa, cytarabin, edatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

General Synthetic Route Description

The compounds of Formula (I), in which R1, R2, R3, R4, R5, R6 and R7 represent a hydrogen atom and R8 represents an optionally substituted aryl, heteroaryl, or heterocyclic group can be synthesized by the general route described in the scheme 1.

-continued

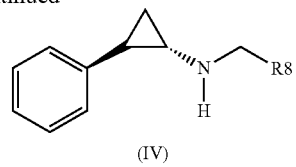

(IV)

Commercially available trans-Phenylcyclopropylamine (ALDRICH) of Formula (II) is reductively alkylated using commercially available aldehydes of Formula (III) R8CHO, in which R8 is as defined earlier (e.g., in the markush groups described above), to give the compounds of Formula (IV), which are a particular case of the compounds claimed in the present invention.

The procedures for preparing the compounds of Formula (I), e.g., where the phenyl ring of the phenylcyclopropylamine core is substituted (in this scheme with a benzyloxy moiety; other moieties substituting the phenyl ring of the phenylcyclopropylamine core can be used as is recognized by the skilled artisan) are exemplified in Scheme 2.

Scheme 2

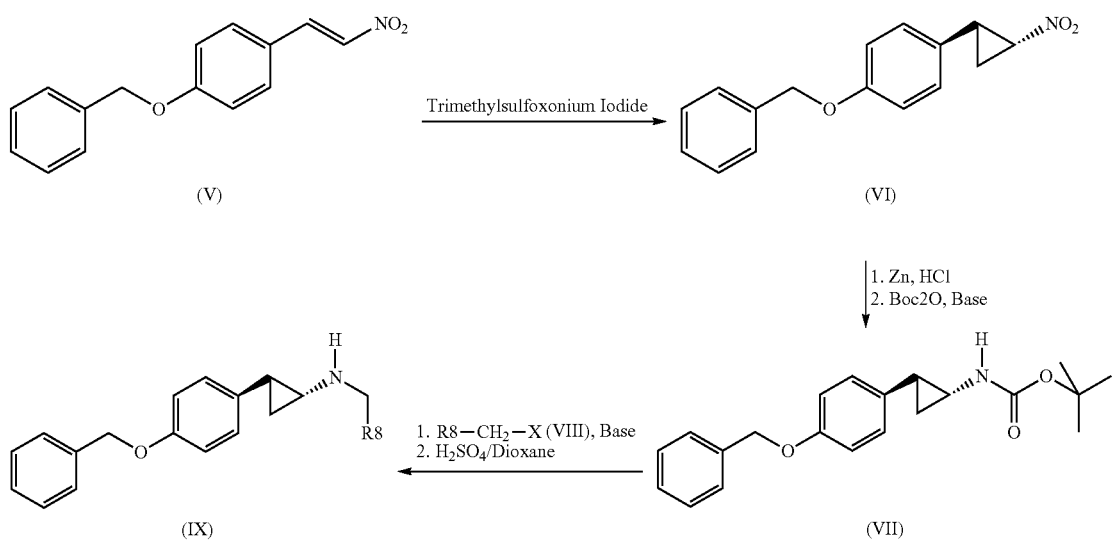

Cyclopropanation reaction of commercially available nitroolefin derivatives of Formula (V) using trimethylsulfoxonium iodide gives derivatives of Formula (VI). Reduction of the nitro group by zinc, followed by protection, with Boc, of the resulting amino group by tertbutyloxycarbonyl leads to the derivatives of Formula (VII). These derivatives were alkylated using a base and an alkylating reagent of Formula (VIII), where R8 is as defined before and X represents a halogen atom (e.g., —Cl or —Br). Deprotection of the Boc group using sulfuric acid affords the derivatives of Formula (IX), which are specific examples of the compounds of Formula (I).

Compounds of Formula (I), in which R1, R2, R3, R4, R5 and R6 represent a hydrogen atom, R7 represents alkyl or cycloalkyl and R8 represents an optionally substituted aryl, heteroaryl, or heterocyclic group can be synthesized by the general route described in the scheme 3.

Scheme 1

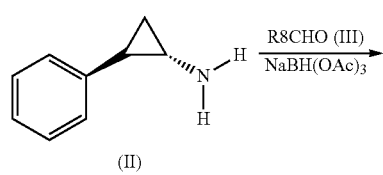

(II)

Scheme 3

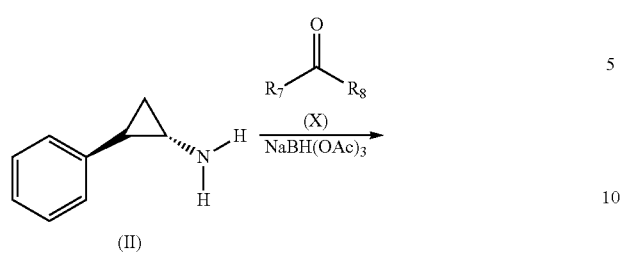

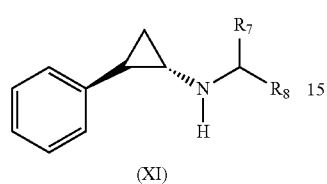

(XI)

Commercially available trans-phenylcyclopropylamine (ALDRICH) of Formula (II) is reductively alkylated using commercially available ketones of Formula (X), in which R7 and R8 are as defined earlier, to give the compounds of Formula (XI), which are also subjects of the present invention.

Compounds of Formula (I), where R1 to R5 may be different than a hydrogen and R8 represents an optionally substituted oxadiazole can be synthesized by the general route described in the scheme 4.

Scheme 4: ACN (acetonitrile), DIGLYME (bis(2-methoxyethyl) ether), DIPEA (N,N-Diisopropylethylamine), EDC (1-ethyl-3-(3-dimethylaminopropyl) carbodiimide), THF (Tetrahydrofurane)

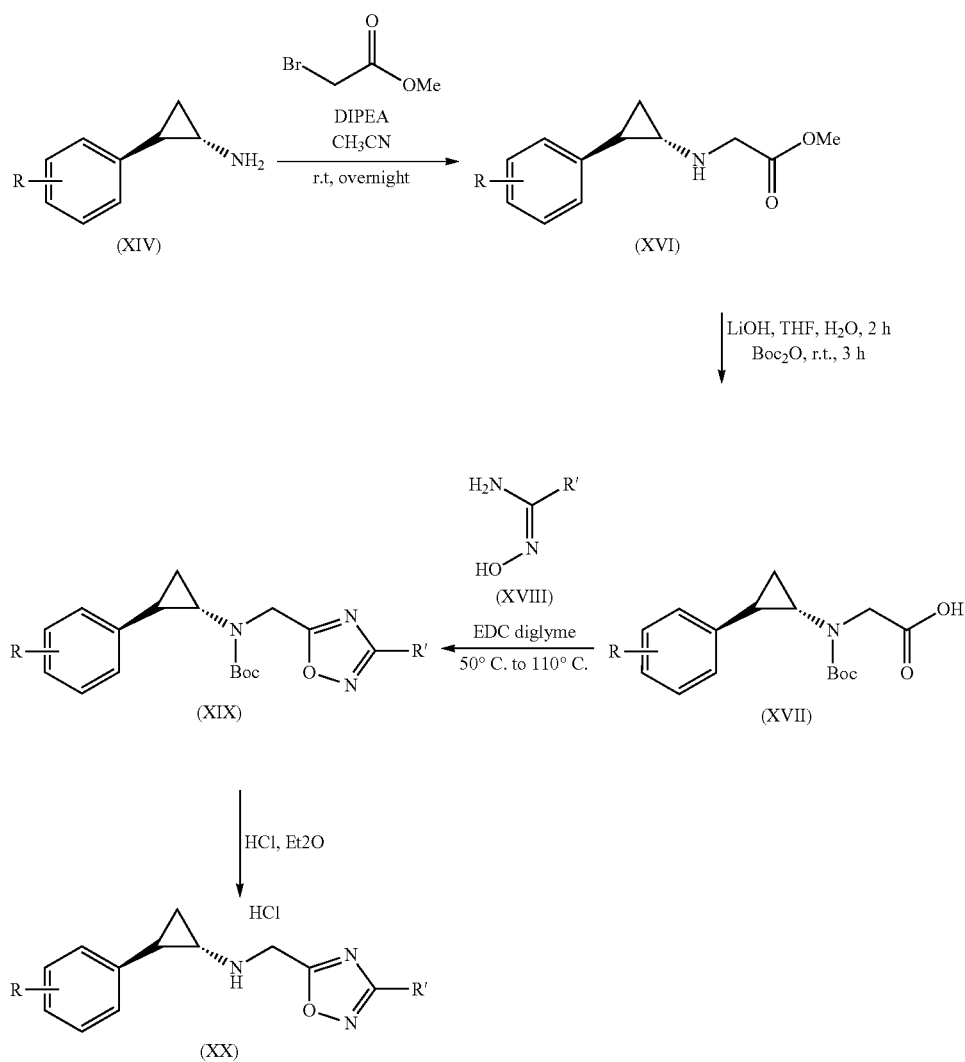

The trans phenylcyclopropylamino derivatives of formula (XIV) (including trans ((1S,2R), (1R,2S)) version as well the individual diastereoisomers corresponding to (1S,2R) and (1R,2S) can be used) are reacted with methyl 2-bromoacetate in acetonitrile using N,N-diisopropylethylamine as a base to give methyl 2-((trans)-2-phenylcyclopropylamino)acetate derivatives of formula (XVI). Hydrolysis with lithium hydroxide using tetrahydrofurane-water solution as a solvent and later reaction with t-butyl dicarbonate in tetrahydrofurane leads to 2-(tert-butoxycarbonyl((trans)-2-phenylcyclopropyl)amino)acetic acid derivatives of formula (XVII), which are reacted with commercially available formamidoxime derivatives of formula (XVIII) and 1-ethyl-3-(3-dimethylaminopropyl)carbodiimide in diglyme to obtain tert-butyl (1,2,4-oxadiazol-5-yl)methyl((trans)-2-phenylcyclopropyl)carbamate derivatives of formula (XIX). Final Boc-deprotection using HCl 2M in diethyl ether using diethyl ether as a solvent leads to the formation of the corresponding hydrochloride salt of the (trans)-N-((1,2,4-oxadiazol-5-yl)methyl)-2-phenylcyclopropanamine derivatives of formula (XX), which are also subjects of the present invention.

The compounds in the examples below can be synthesized using these procedures described above or modifications thereof by an ordinary artisan skilled in the art of synthetic organic chemistry.

It is to be understood that wherever a substituent in a structure depicted herein is not specified (e.g. is "missing" in the structure) said substituent is a hydrogen atom.

The title Example compounds below were named using the ChemBioDraw Ultra version 11.0.1 by CambridgeSoft program. In the case of a conflict between a name and a drawn structure, the drawn structure is the controlling definition.

EXAMPLES

Example 1

(trans)-N-(4-fluorobenzyl)-2-phenylcyclopropanamine

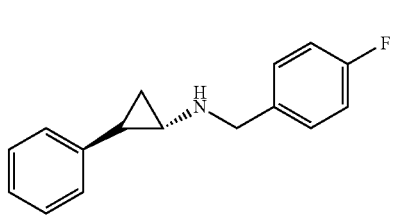

A mixture of (trans)-2-phenylcyclopropanamine hydrochloride (0.25 g, 1.50 mmol) and 4-fluorobenzaldehyde (0.18 mL, 1.65 mmol) in $CH_2Cl_2$ (8 mL) and water (0.5 mL) was vigorously stirred at room temperature for 10 min. Then, $NaBH(OAc)_3$ (0.41 g, 1.95 mmol) was slowly added and stirring continued for 1.5 h. The reaction mixture was washed with an aqueous saturated solution of $NaHCO_3$ (10 mL), the organic layer was dried over anhydrous $Na_2SO_4$, filtered and, after removal of the solvent, the residual oil was purified by column chromatography on silica gel (3% MeOH/$CH_2Cl_2$) affording 0.18 g of N-(4-fluorobenzyl)-N-[(trans)-2-phenylcyclopropyl]amine [Rf=0.5 (5% MeOH/$CH_2Cl_2$), colorless oil, 49% yield].

Example 2

(trans)-N-(4-fluorobenzyl)-2-phenylcyclopropanaminium chloride

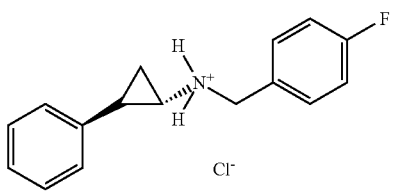

2 M ethereal solution of HCl (0.24 mL, 0.47 mmol) was slowly added to a solution of N-(4-fluorobenzyl)-N-[(trans)-2-phenylcyclopropyl]amine (95 mg, 0.39 mmol) in dry $Et_2O$ (10 mL) cooled at −78° C., and allowed to reach room temperature. After 10 min the white precipitate was allowed to settle and $Et_2O$ was decanted, the solid was washed with $Et_2O$ (10 mL) and vacuum dried, rendering 90 mg of N-(4-fluorobenzyl)-N-[(trans)-2-phenylcyclopropyl]amine hydrochloride (white solid, 83% yield).

$^1$H-NMR (MeOD, 250 MHz, δ): 7.59-7.49 (m, 2H, ArH); 7.34-7.05 (m, 7H, ArH); 4.38 (s, 2H, CH2); 3.02-2.93 (m, 1H, CH); 2.52-2.40 (m, 1H, CH); 1.58-1.31 (m, 2H, CH2).

Example 3

4-(((trans)-2-phenylcyclopropylamino)methyl)benzonitrile

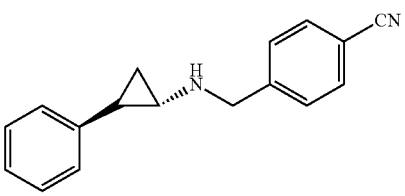

A mixture of (trans)-2-phenylcyclopropanamine hydrochloride (0.25 g, 1.50 mmol) and 4-cyanobenzaldehyde (0.22 g, 1.65 mmol) in $CH_2Cl_2$ (8 mL) and water (0.5 mL) was vigorously stirred at room temperature for 10 min. Then, $NaBH(OAc)_3$ (0.41 g, 1.95 mmol) was slowly added and stirring continued for 1.5 h. The reaction mixture was washed with an aqueous saturated solution of $NaHCO_3$ (10 mL), the organic layer was dried over anhydrous $Na_2SO_4$, filtered and, after removal of the solvent, the residual oil was purified by column chromatography on silica gel (1% MeOH/$CH_2Cl_2$)

affording 0.07 g of 4-({[(trans)-2-phenylcyclopropyl]amino}methyl)benzonitrile [Rf=0.6 (5% MeOH/CH$_2$Cl$_2$), colorless oil, 19% yield].

Example 4

(trans)-N-(4-cyanobenzyl)-2-phenylcyclopropan-aminium chloride

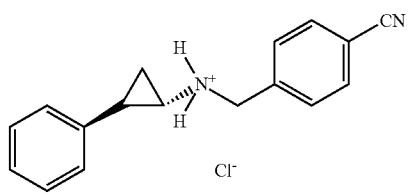

2 M ethereal solution of HCl (0.14 mL, 0.27 mmol) was slowly added to a solution of 4-({[(trans)-2-phenylcyclopropyl]amino}methyl)benzonitrile (67 mg, 0.27 mmol) in dry Et$_2$O (5 mL) cooled at −78° C., and allowed to reach room temperature. After 10 min the white precipitate was allowed to settle and Et$_2$O was decanted, the solid was washed with Et$_2$O (20 mL) and vacuum dried, rendering 65 mg of 4-({[(trans)-2-phenylcyclopropyl]amino}methyl)benzonitrile hydrochloride (white solid, 84% yield).

$^1$H-NMR (MeOD, 250 MHz, γ): 7.81 (d, J=8.5 Hz, 2H, ArH); 7.71 (d, J=8.5 Hz, 2H, ArH); 7.35-7.19 (m, 3H, ArH); 7.14-7.07 (m, 2H, ArH); 4.49 (s, 2H, CH2); 3.06-2.98 (m, 1H, CH); 2.52-2.43 (m, 1H, CH); 1.61-1.50 (m, 1H, CH2); 1.44-1.33 (m, 1H, CH2).

Example 5

(trans)-2-phenyl-N-(4-(trifluoromethyl)benzyl)cyclo-propanamine

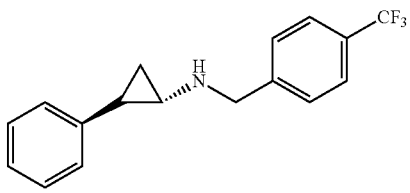

A mixture of (trans)-2-phenylcyclopropanamine hydrochloride (0.23 g, 1.36 mmol) and 4-(trifluoromethyl)benzaldehyde (0.20 mL, 1.49 mmol) in CH$_2$Cl$_2$ (8 mL) and water (0.5 mL) was vigorously stirred at room temperature for 10 min. Then, NaBH(OAc)$_3$ (0.37 g, 1.76 mmol) was slowly added and stirring continued for 30 min. The reaction mixture was washed with an aqueous saturated solution of NaHCO$_3$ (8 mL), the organic layer was dried over anhydrous Na$_2$SO$_4$, filtered and, after removal of the solvent, the residual oil was purified by column chromatography on silica gel (1% MeOH/CH$_2$Cl$_2$) affording 0.15 g of N-[(trans)-2-phenylcyclopropyl]-N-[4-(trifluoromethyl)benzyl]amine [Rf=0.6 (5% MeOH/CH$_2$Cl$_2$), colorless oil, 38% yield].

Example 6

(trans)-2-phenyl-N-(4-(trifluoromethyl)benzyl)cyclo-propanaminium chloride

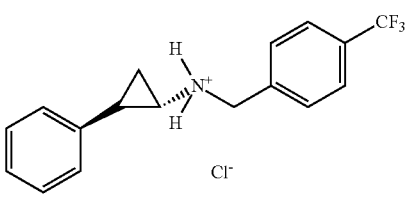

2 M ethereal solution of HCl (0.28 mL, 0.57 mmol) was slowly added to a solution of N-[(trans)-2-phenylcyclopropyl]-N-[4-(trifluoromethyl)benzyl]amine (150 mg, 0.51 mmol) in dry Et$_2$O (8 mL) cooled at −78° C., and allowed to reach room temperature. After 10 min the white precipitate was allowed to settle and Et$_2$O was decanted, the solid was washed with Et$_2$O (10 mL) and vacuum dried, rendering 105 mg of N-[(trans)-2-phenylcyclopropyl]-N-[4-(trifluoromethyl)benzyl]amine hydrochloride (white solid, 62% yield).

$^1$H-NMR (MeOD, 250 MHz, δ): 7.78-7.65 (m, 4H, ArH); 7.34-7.20 (m, 3H, ArH); 7.13-7.06 (m, 2H, ArH); 4.49 (s, 2H, CH2); 3.07-2.97 (m, 1H, CH); 2.51-2.40 (m, 1H, CH); 1.61-1.49 (m, 1H, CH2); 1.46-1.34 (m, 1H, CH2).

Example 7

(trans)-2-phenyl-N-(pyridin-2-ylmethyl)cyclopro-panamine

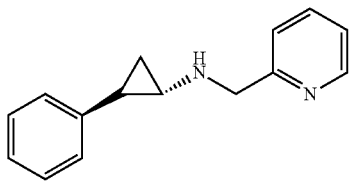

A mixture of (trans)-2-phenylcyclopropanamine hydrochloride (0.25 g, 1.50 mmol) and pyridine-2-carbaldehyde (0.17 mL, 1.80 mmol) in CH$_2$Cl$_2$ (12 mL) and water (0.5 mL) was vigorously stirred at room temperature for 10 min. Then, NaBH(OAc)$_3$ (0.48 g, 2.25 mmol) was slowly added and stirring continued for 2 h. The reaction mixture was washed with an aqueous saturated solution of NaHCO$_3$ (10 mL), the organic layer was dried over anhydrous Na$_2$SO$_4$, filtered and, after removal of the solvent, the residual oil was purified by column chromatography on silica gel [4% MeOH+1% NH$_3$ (aq)/CH$_2$Cl$_2$] followed by preparative layer chromatography (5% MeOH/CH$_2$Cl$_2$) affording 0.08 g of N-[(trans)-2-phenylcyclopropyl]-N-(pyridin-2-ylmethyl)amine [Rf=0.3 (5% MeOH/CH$_2$Cl$_2$), colorless oil, 24% yield]. $^1$H-NMR (CDCl$_3$, 250 MHz, δ): 8.60-8.54 (m, 1H, ArH); 7.62 (td, J=7.8, 1.6 Hz, 1H, ArH); 7.28-7.09 (m, 5H, ArH); 7.03-6.97 (m, 2H, ArH); 4.01 (s, 2H, CH2); 2.44-2.37 (m, 1H, CH); 2.09 (br s, 1H, NH); 2.01-1.92 (m, 1H, CH); 1.19-1.10 (m, 1H, CH2); 1.02-0.94 (m, 1H, CH2).

The following examples 8 to 25 have been synthesized using the procedure described for examples 1-6 starting with the corresponding aldehydes.

Example 8

(trans)-2-phenyl-N-(pyridin-3-ylmethyl)cyclopropanamine

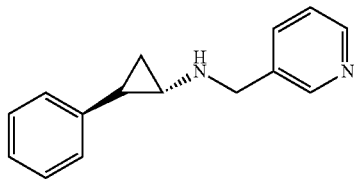

$^1$H-NMR (CDCl$_3$, 250 MHz, δ): 8.60-8.54 (m, 1H, ArH); 7.62 (td, J=7.8, 1.6 Hz, 1H, ArH); 7.28-7.09 (m, 5H, ArH); 7.03-6.97 (m, 2H, ArH); 4.01 (s, 2H, CH2); 2.44-2.37 (m, 1H, CH); 2.09 (br s, 1H, NH); 2.01-1.92 (m, 1H, CH); 1.19-1.10 (m, 1H, CH2); 1.02-0.94 (m, 1H, CH2).

Example 9

(trans)-2-phenyl-N-(pyridin-4-ylmethyl)cyclopropanamine

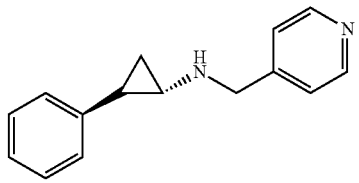

$^1$H-NMR (CDCl$_3$, 250 MHz, δ): 8.60-8.54 (m, 1H, ArH); 7.62 (td, J=7.8, 1.6 Hz, 1H, ArH); 7.28-7.09 (m, 5H, ArH); 7.03-6.97 (m, 2H, ArH); 4.01 (s, 2H, CH2); 2.44-2.37 (m, 1H, CH); 2.09 (br s, 1H, NH); 2.01-1.92 (m, 1H, CH); 1.19-1.10 (m, 1H, CH2); 1.02-0.94 (m, 1H, CH2).

Example 10

(trans)-N-((6-methylpyridin-2-yl)methyl)-2-phenyl-cyclopropanamine

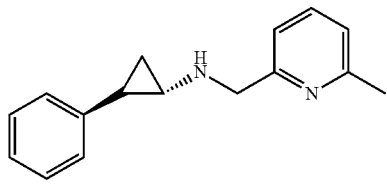

$^1$H-NMR (CDCl$_3$, 250 MHz, δ): 8.60-8.54 (m, 1H, ArH); 7.62 (td, J=7.8, 1.6 Hz, 1H, ArH); 7.28-7.09 (m, 5H, ArH); 7.03-6.97 (m, 2H, ArH); 4.01 (s, 2H, CH2); 2.44-2.37 (m, 1H, CH); 2.09 (br s, 1H, NH); 2.01-1.92 (m, 4H); 1.19-1.10 (m, 1H, CH2); 1.02-0.94 (m, 1H, CH2).

Example 11

(trans)-2-phenyl-N-(thiazol-2-ylmethyl)cyclopropanamine

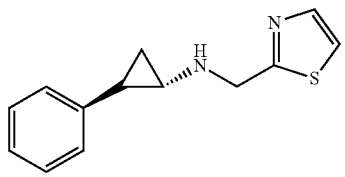

$^1$H-NMR (CDCl$_3$, 250 MHz, δ): 7.72 (d, J=3.3 Hz, 1H, ArH); 7.28-7.09 (m, 4H, ArH); 7.04-6.96 (m, 2H, ArH); 4.24 (s, 2H, CH2); 2.54-2.46 (m, 1H, CH); 2.37 (br s, 1H, NH); 2.05-1.94 (m, 1H, CH); 1.19-1.09 (m, 1H, CH2); 1.05-0.95 (m, 1H, CH2).

Example 12

(trans)-2-phenyl-N-(thiophen-2-ylmethyl)cyclopropanamine

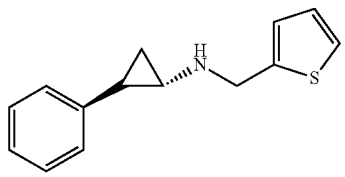

$^1$H-NMR (CDCl$_3$, 250 MHz, δ): 7.72 (d, 2H, ArH); 7.28-7.09 (m, 4H, ArH); 7.04-6.96 (m, 2H, ArH); 4.24 (s, 2H, CH2); 2.54-2.46 (m, 1H, CH); 2.37 (br s, 1H, NH); 2.05-1.94 (m, 1H, CH); 1.19-1.09 (m, 1H, CH2); 1.05-0.95 (m, 1H, CH2).

Example 13

(trans)-N-((3-bromothiophen-2-yl)methyl)-2-phenyl-cyclopropanamine

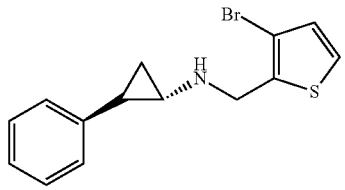

$^1$H-NMR (CDCl$_3$, 250 MHz, δ): 7.72 (d, 1H, ArH); 7.28-7.09 (m, 4H, ArH); 7.04-6.96 (m, 2H, ArH); 4.24 (s, 2H,

CH2); 2.54-2.46 (m, 1H, CH); 2.37 (br s, 1H, NH); 2.05-1.94 (m, 1H, CH); 1.19-1.09 (m, 1H, CH2); 1.05-0.95 (m, 1H, CH2).

Example 14

(trans)-N-((4-bromothiophen-2-yl)methyl)-2-phenyl-cyclopropanamine

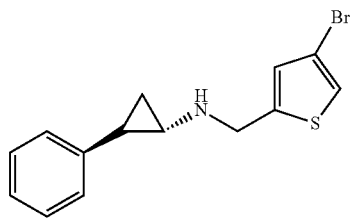

$^1$H-NMR (CDCl$_3$, 250 MHz, δ): 7.72 (d, 1H, ArH); 7.28-7.09 (m, 4H, ArH); 7.04-6.96 (m, 2H, ArH); 4.24 (s, 2H, CH2); 2.54-2.46 (m, 1H, CH); 2.37 (br s, 1H, NH); 2.05-1.94 (m, 1H, CH); 1.19-1.09 (m, 1H, CH2); 1.05-0.95 (m, 1H, CH2).

Example 15

(trans)-N-(3,4-dichlorobenzyl)-2-phenylcyclopropanamine

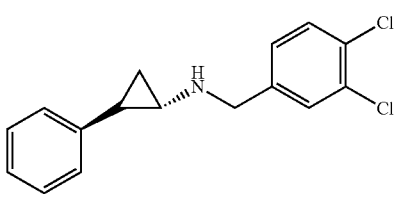

$^1$H-NMR (CDCl$_3$, 250 MHz, δ): 8.60-8.54 (m, 1H, ArH); 7.62 (td, J=7.8, 1.6 Hz, 1H, ArH); 7.28-7.09 (m, 5H, ArH); 7.03-6.97 (m, 2H, ArH); 4.01 (s, 2H, CH2); 2.44-2.37 (m, 1H, CH); 2.09 (br s, 1H, NH); 2.01-1.92 (m, 1H, CH); 1.19-1.10 (m, 1H, CH2); 1.02-0.94 (m, 1H, CH2).

Example 16

(trans)-N-(3-fluorobenzyl)-2-phenylcyclopropan-aminium chloride

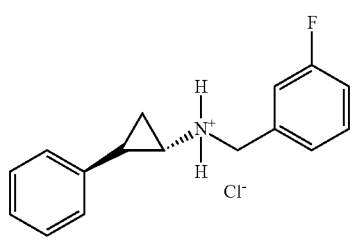

$^1$H-NMR (MeOD, 250 MHz, δ): 7.59-7.49 (m, 2H, ArH); 7.34-7.05 (m, 7H, ArH); 4.38 (s, 2H, CH2); 3.02-2.93 (m, 1H, CH); 2.52-2.40 (m, 1H, CH); 1.58-1.31 (m, 2H, CH2).

Example 17

(trans)-N-(2-fluorobenzyl)-2-phenylcyclopropan-amine

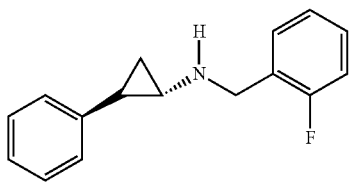

$^1$H-NMR (MeOD, 250 MHz, δ): 7.59-7.49 (m, 2H, ArH); 7.34-7.05 (m, 7H, ArH); 4.38 (s, 2H, CH2); 3.02-2.93 (m, 1H, CH); 2.52-2.40 (m, 1H, CH); 1.58-1.31 (m, 2H, CH2).

Example 18

(trans)-2-phenyl-N-(quinolin-4-ylmethyl)cyclopropanamine

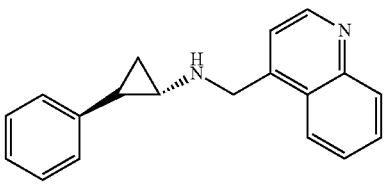

$^1$H-NMR (CDCl$_3$, 250 MHz, δ): 8.60-8.54 (m, 1H, ArH); 7.62 (td, J=7.8, 1.6 Hz, 1H, ArH); 7.28-7.09 (m, 7H, ArH); 7.03-6.97 (m, 2H, ArH); 4.01 (s, 2H, CH2); 2.44-2.37 (m, 1H, CH); 2.09 (br s, 1H, NH); 2.01-1.92 (m, 1H, CH); 1.19-1.10 (m, 1H, CH2); 1.02-0.94 (m, 1H, CH2).

Example 19

(trans)-N-(3-methoxybenzyl)-2-phenylcyclopropan-amine

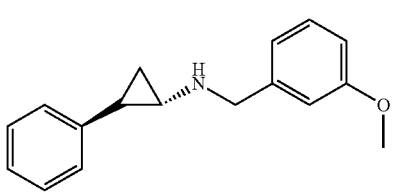

Example 20

(trans)-2-phenyl-N-((6-(trifluoromethyl)pyridin-3-yl)methyl)cyclopropanamine

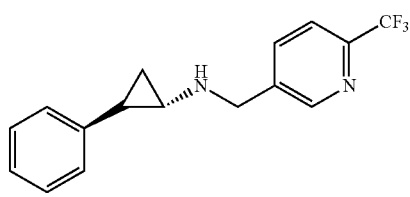

¹H-NMR (CDCl₃, 250 MHz, δ): 8.60-8.54 (m, 1H, ArH); 7.62 (td, J=7.8, 1.6 Hz, 1H, ArH); 7.28-7.09 (m, H, ArH); 7.03-6.97 (m, 2H, ArH); 4.01 (s, 2H, CH2); 2.44-2.37 (m, 1H, CH); 2.09 (br s, 1H, NH); 2.01-1.92 (m, 1H, CH); 1.19-1.10 (m, 1H, CH2); 1.02-0.94 (m, 1H, CH2).

Example 21

(trans)-N-((6-chloropyridin-3-yl)methyl)-2-phenyl-cyclopropanamine

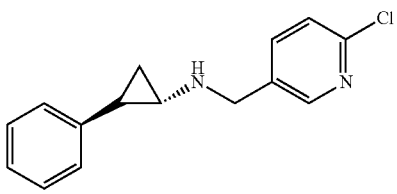

¹H-NMR (CDCl₃, 250 MHz, δ): 8.60-8.54 (m, 1H, ArH); 7.62 (td, J=7.8, 1.6 Hz, 1H, ArH); 7.28-7.09 (m, 4H, ArH); 7.03-6.97 (m, 2H, ArH); 4.01 (s, 2H, CH2); 2.44-2.37 (m, 1H, CH); 2.09 (br s, 1H, NH); 2.01-1.92 (m, 1H, CH); 1.19-1.10 (m, 1H, CH2); 1.02-0.94 (m, 1H, CH2).

Example 22

(trans)-N-((4-methylpyridin-2-yl)methyl)-2-phenyl-cyclopropanamine

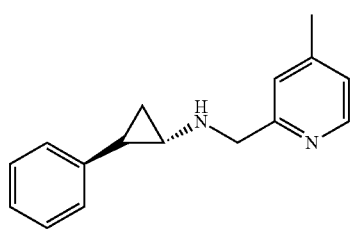

¹H-NMR (CDCl₃, 250 MHz, δ): 8.60-8.54 (m, 1H, ArH); 7.62 (td, J=7.8, 1.6 Hz, 1H, ArH); 7.28-7.09 (m, 4H, ArH); 7.03-6.97 (m, 2H, ArH); 4.01 (s, 2H, CH2); 2.44-2.37 (m, 1H, CH); 2.29 (s, 3H, CH3); 2.09 (br s, 1H, NH); 2.01-1.92 (m, 1H, CH); 1.19-1.10 (m, 1H, CH2); 1.02-0.94 (m, 1H, CH2).

Example 23

(trans)-N-((6-methoxypyridin-2-yl)methyl)-2-phenylcyclopropanamine

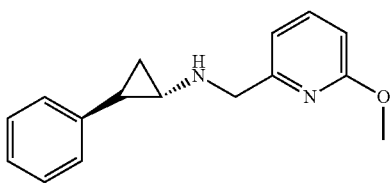

¹H-NMR (CDCl₃, 250 MHz, δ): 8.60-8.54 (m, 1H, ArH); 7.62 (td, J=7.8, 1.6 Hz, 1H, ArH); 7.28-7.09 (m, 4H, ArH); 7.03-6.97 (m, 2H, ArH); 4.01 (s, 5H, CH2+CH3); 2.44-2.37 (m, 1H, CH); 2.09 (br s, 1H, NH); 2.01-1.92 (m, 1H, CH); 1.19-1.10 (m, 1H, CH2); 1.02-0.94 (m, 1H, CH2).

Example 24

2-(((trans)-2-phenylcyclopropylamino)methyl)pyridin-3-ol

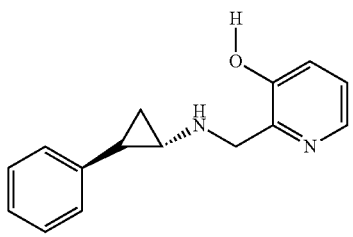

¹H-NMR (CDCl₃, 250 MHz, δ): 8.60-8.54 (m, 1H, ArH); 7.62 (td, J=7.8, 1.6 Hz, 1H, ArH); 7.28-7.09 (m, 3H, ArH); 7.03-6.97 (m, 2H, ArH); 4.01 (s, 5H, CH2+CH3); 2.44-2.37 (m, 1H, CH); 2.09 (br s, 1H, NH); 2.01-1.92 (m, 1H, CH); 1.19-1.10 (m, 1H, CH2); 1.02-0.94 (m, 1H, CH2).

Example 25

(trans)-N-((6-bromopyridin-2-yl)methyl)-2-phenyl-cyclopropanamine

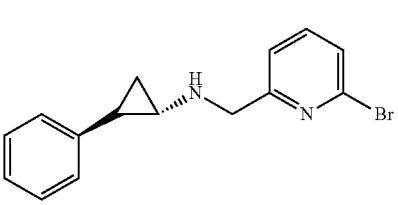

¹H-NMR (CDCl₃, 250 MHz, δ): 7.60-7.00 (m, 8H, ArH); 3.90 (s, 2H, CH2); 2.44-2.37 (m, 1H, CH); 2.09 (br s, 1H, NH); 2.01-1.92 (m, 4H); 1.19-1.10 (m, 1H, CH2); 1.02-0.94 (m, 1H, CH2).

Example 26

4-(((trans)-2-(4-(benzyloxy)phenyl)cyclopropylamino)methyl)benzonitrile

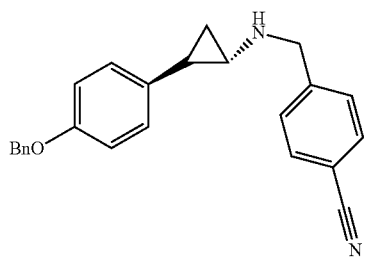

¹H-NMR (MeOD, 250 MHz, δ): 7.88-7.22 (m, 9H, ArH); 6.82 (m, 4H, ArH); 5.01 (s, 2H, CH2); 3.85 (s, 2H, CH2); 2.25-2.18 (m, 1H, CH); 1.90-1.81 (m, 1H, CH); 1.07-0.97 (m, 1H, CH2); 0.95-0.85 (m, 1H, CH2).

Example 27

(trans)-N-(4-(benzyloxy)benzyl)-2-phenylcyclopropanamine

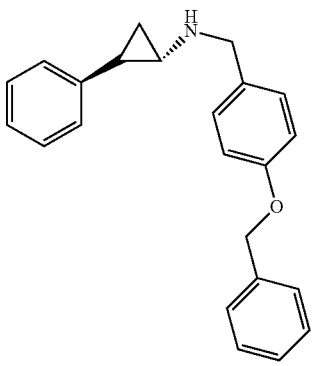

¹H-NMR (MeOD, 250 MHz, δ): 7.44-7.21 (m, 9H, ArH); 6.94-6.81 (m, 4H, ArH); 5.01 (s, 2H, CH2); 3.82 (s, 2H, CH2); 2.25-2.18 (m, 1H, CH); 1.90-1.81 (m, 1H, CH); 1.07-0.97 (m, 1H, CH2); 0.95-0.85 (m, 1H, CH2).

Intermediate 1: 1-(benzyloxy)-4-[(trans)-2-nitrocyclopropyl]benzene

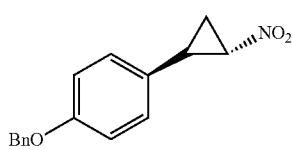

Trimethylsulfoxonium iodide (0.62 g, 2.82 mmol) was added in portions to a solution of t-BuOK (0.32 g, 2.82 mmol) in dry DMSO (5 mL). After 10 min a solution of 1-(benzyloxy)-4-[(E)-2-nitrovinyl]benzene (0.60 g, 2.35 mmol) in DMSO (5 mL) was transferred via canula and the mixture was stirred at room temperature for 6 h. The reaction was poured over water (10 mL) and extracted with Et₂O (3×10 mL); the organic layers were washed with brine (2×15 mL), dried over anhydrous Na₂SO₄ and filtered. After removal of the solvent, the residual orange oil was purified by column chromatography on silica gel (5% EtOAc/hexanes) affording 0.16 g of 1-(benzyloxy)-4-[(1R,2S)-2-nitrocyclopropyl]benzene [Rf=0.5 (20% EtOAc/hexanes), white solid, 26% yield].

Intermediate 2: Trans-2-[4-(benzyloxy)phenyl]cyclopropanamine

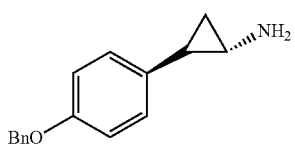

Zn dust (1.97 g, 30 mol) was added in small portions, over a period of 30 min, to a vigorously stirred solution of 1-(benzyloxy)-4-[(1R,2S)-2-nitrocyclopropyl]benzene (0.81 g, 3.0 mmol) in i-PrOH (25 mL) and HCl (11 mL of aqueous solution 2.7 N, 30 mmol). After 17 h the mixture was filtered through a pad of celite, that was washed with 10 mL of methanol. The filtrate was concentrated and 10 mL of water were added, washing with CH₂Cl₂ (3×15 mL). The organic layers were dried over anhydrous Na₂SO₄ and filtered. After removal of the solvent, the crude product was purified by column chromatography on silica gel (10% MeOH/CH₂Cl₂) affording 0.50 g of (trans)-2-[4-(benzyloxy)phenyl]cyclopropanamine [Rf=0.2 (10% MeOH/CH₂Cl₂), white solid, 70% yield]. ¹H-NMR (MeOH, 250 MHz, δ): 7.45-7.27 (m, 5H, ArH); 6.96 (d, J=8.5 Hz, 2H, ArH); 6.86 (d, J=8.5 Hz, 2H, ArH); 5.03 (s, 2H, CH2); 2.41-2.34 (m, 1H, CH); 1.86-1.76 (m, 1H, CH); 0.98-0.85 (m, 2H, CH2).

Intermediate 3: Intermediate tert-Butyl(trans)-2-[4-(benzyloxy)phenyl]cyclopropylcarbamate

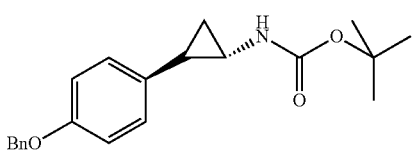

200 mg of intermediate x (trans)-2-[4-(benzyloxy)phenyl] cyclopropanamine were dissolved in pyridine (5 mL) and tertbutyl carbonate (200 mg) was then added. The mixture was stirred at room temperature for 12 h, the poured into ice-water. The desired compound was filtered and dried. ¹H-NMR (MeOH, 250 MHz, δ): 7.45-7.27 (m, 5H, ArH); 6.96 (d, 8.5 Hz, 2H, ArH); 6.86 (d, J=8.5 Hz, 2H, ArH); 5.03

(s, 2H, CH2); 2.41-2.34 (m, 1H, CH); 1.86-1.76 (m, 10H, CH); 0.98-0.85 (m, 2H, CH2).

Example 28

(trans)-N-benzyl-2-(4-(benzyloxy)phenyl)cyclopropanamine

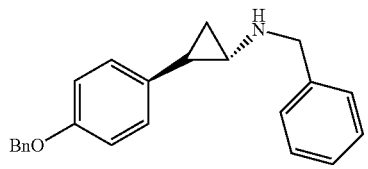

NaH (17 mg, 60% in mineral oil, 0.42 mmol) was added to a solution of tert-Butyl (trans)-2-[4-(benzyloxy)phenyl]cyclopropylcarbamate (110 mg, 0.32 mmol) in DMF (4 mL) at 0° C. After 30 minutes, benzyl bromide (0.05 mL, 0.42 mmol) was added and the reaction was allowed to reach r.t. and stirred for additional 16 h. The reaction mixture was poured into $H_2O$ (15 mL) and extracted with $Et_2O$ (3×5 mL); the organic layers were washed with brine (10 mL), dried over anhydrous $Na_2SO_4$ and filtered.

After removal of the solvent, the residual yellowish oil was solved in a mixture of 1,4-dioxane/$H_2SO_4$ (4 mL, 10:1, v/v) and stirred for 40 min. The solution was basified by addition of 6 mL of aqueous NaOH (10%) and extracted with $Et_2O$ (2×10 mL); the organic layers were washed with brine (15 mL), dried over anhydrous $Na_2SO_4$ and filtered. After removal of the solvent, the crude residue was purified by column chromatography on silica gel (10-40% EtOAc/hexanes) to afford 58 mg of N-benzyl-N-{(trans)-2-[4-(benzyloxy)phenyl]cyclopropyl}amine [Rf=0.2 (5% MeOH/$CH_2Cl_2$), white solid, 55% yield]. $^1$H-NMR (MeOD, 250 MHz, δ): 7.44-7.21 (m, 10H, ArH); 6.94-6.81 (m, 4H, ArH); 5.01 (s, 2H, CH2); 3.82 (s, 2H, CH2); 2.25-2.18 (m, 1H, CH); 1.90-1.81 (m, 1H, CH); 1.07-0.97 (m, 1H, CH2); 0.95-0.85 (m, 1H, CH2).

Following examples have been synthesized using the procedure described for Example 28 and the corresponding starting materials.

Example 29

(trans)-2-(4-(benzyloxy)phenyl)-N-(4-methoxybenzyl)cyclopropanamine

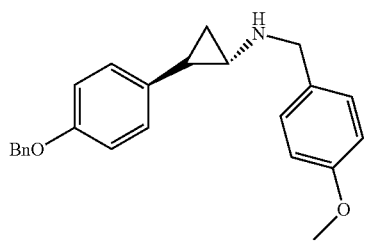

$^1$H-NMR (MeOD, 250 MHz, δ): 7.44-7.21 (m, 9H, ArH); 6.94-6.81 (m, 4H, ArH); 5.01 (s, 2H, CH2); 3.65 (s, 3H, OCH3); 3.82 (s, 2H, CH2); 2.25-2.18 (m, 1H, CH); 1.90-1.81 (m, 1H, CH); 1.07-0.97 (m, 1H, CH2); 0.95-0.85 (m, 1H, CH2).

Example 30

(trans)-2-(4-(benzyloxy)phenyl)-N-(4-fluorobenzyl)cyclopropanamine

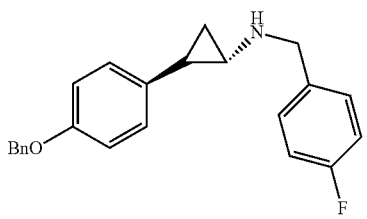

$^1$H-NMR (MeOD, 250 MHz, δ): 7.44-7.21 (m, 8H, ArH); 6.94-6.81 (m, 4H, ArH); 5.01 (s, 2H, CH2); 3.82 (s, 2H, CH2); 2.25-2.18 (m, 1H, CH); 1.90-1.81 (m, 1H, CH); 1.07-0.97 (m, 1H, CH2); 0.95-0.85 (m, 1H, CH2).

Following examples have been synthesized using the procedure described for Examples 1 and 2 and the corresponding starting materials.

Example 31

(trans)-2-phenyl-N-(quinolin-2-ylmethyl)cyclopropanamine

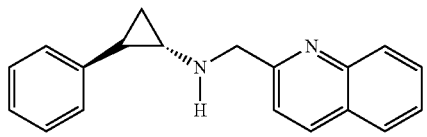

$^1$H-NMR (CDCl3) δ (ppm): 1.00 (q, 1H), 1.18 (quin, 1H), 2.00 (m, 1H), 2.49 (m, 1H), 4.22 (s, 2H), 7.02 (d, 2H), 7.16 (q, 2H), 7.23 (d, 1H), 7.40 (d, 1H), 7.53 (t, 1H), 7.69 (t, 1H), 7.80 (d, 1H), 8.09 (t, 2H). MS (M+H): 275.0

Example 32

(trans)-2-phenyl-N-((5-(trifluoromethyl)pyridin-2-yl)methyl)cyclopropanamine

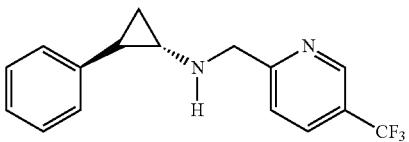

¹H-NMR (CDCl3) δ (ppm): 0.98 (q, 1H), 1.13 (quin, 1H), 1.93 (m, 1H), 2.40 (m, 1H), 4.07 (s, 2H), 6.98 (d, 2H), 7.13 (d, 1H), 7.22 (t, 2H), 7.40 (d, 1H), 7.84 (d, 1H), 8.82 (s, 1H). MS (M+H): 292.8

Example 33

(trans)-N-((3-fluoropyridin-2-yl)methyl)-2-phenylcyclopropanamine

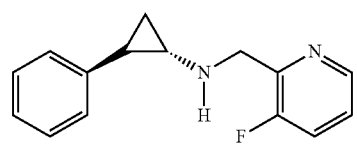

¹H-NMR (CDCl3) δ (ppm): 1.01 (q, 1H), 1.18 (quin, 1H), 1.99 (m, 1H), 2.41 (m, 1H), 4.11 (s, 2H), 7.02 (d, 2H), 7.25 (m, 5H), 8.38 (s, 1H). MS (M+H): 242.8

Example 34

(trans)-2-phenyl-N-(quinolin-3-ylmethyl)cyclopropanamine

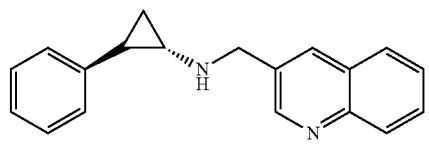

¹H-NMR (CDCl3) δ (ppm): 1.00 (q, 1H), 1.12 (quin, 1H), 1.94 (m, 1H), 2.40 (m, 1H), 4.10 (s, 2H), 6.95 (d, 2H), 7.14 (t, 1H), 7.20 (t, 2H), 7.54 (t, 1H), 7.70 (t, 1H), 7.76 (d, 1H), 8.04 (s, 1H), 8.10 (d, 1H), 8.90 (s, 1H). MS (M+H): 275.0

Example 35

(trans)-N-((6-methoxypyridin-3-yl)methyl)-2-phenylcyclopropanamine

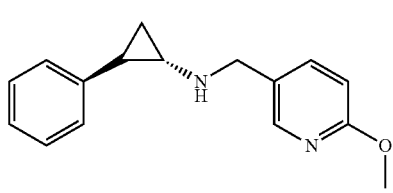

¹H-NMR (CDCl3) δ (ppm): 0.98 (q, 1H), 1.10 (quin, 1H), 1.94 (m, 1H), 2.36 (m, 1H), 3.82 (s, 2H), 3.92 (s, 3H), 6.70 (d, 1H), 7.00 (d, 2H), 7.14 (t, 1H), 7.24 (d, 2H), 7.54 (d, 1H), 8.08 (s, 1H). MS (M+H): 255.0

Example 36

(trans)-N-((5-methoxypyridin-3-yl)methyl)-2-phenylcyclopropanamine

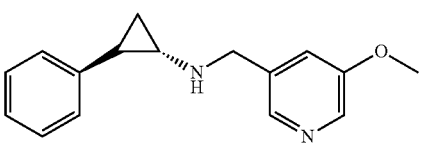

¹H-NMR (CDCl3) δ (ppm): 0.98 (q, 1H), 1.12 (quin, 1H), 1.92 (m, 1H), 2.36 (m, 1H), 3.78 (s, 2H), 3.90 (s, 3H), 6.98 (s, 2H), 7.14 (s, 2H), 7.24 (t, 2H), 8.20 (d, 2H). MS (M+H): 255.0

Example 37

(trans)-N-((2-methoxypyridin-3-yl)methyl)-2-phenylcyclopropanamine

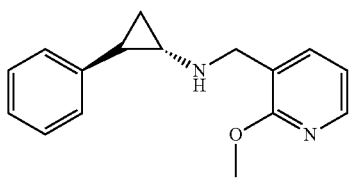

¹H-NMR (CDCl3) δ (ppm): 0.98 (q, 1H), 1.12 (quin, 1H), 1.92 (m, 1H), 2.32 (m, 1H), 3.84 (s, 2H), 3.94 (s, 3H), 6.82 (t, 1H), 7.00 (d, 2H), 7.14 (t, 1H), 7.24 (d, 2H), 7.48 (d, 1H), 8.08 (d, 1H). MS (M+H): 255.0

Example 38

(trans)-N-((3H-indol-3-yl)methyl)-2-phenylcyclopropanamine

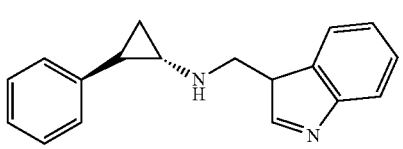

¹H-NMR (CDCl3) δ (ppm): 1.00 (q, 1H), 1.20 (quin, 1H), 2.02 (m, 1H), 2.48 (m, 1H), 4.10 (s, 2H), 7.02 (d, 2H), 7.14 (m, 4H), 7.20 (t, 2H), 7.36 (d, 1H), 7.66 (d, 1H), 8.02 (s, 1H). MS (M+H): 263.0

Example 39

3-(((trans)-2-phenylcyclopropylamino)methyl)benzonitrile

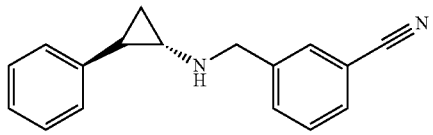

¹H-NMR (CDCl3) δ (ppm): 1.00 (q, 1H), 1.10 (quin, 1H), 1.92 (m, 1H), 2.36 (m, 1H), 3.92 (s, 2H), 6.96 (d, 2H), 7.16 (t, 1H), 7.26 (d, 2H), 7.40 (t, 1H), 7.56 (d, 2H), 7.62 (s, 1H). MS (M+H): 249.0

Example 40

(trans)-N-(2-methoxybenzyl)-2-phenylcyclopropanamine

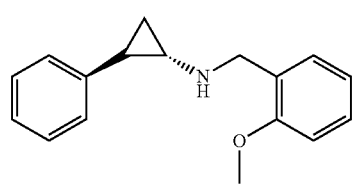

¹H-NMR (CDCl3) δ (ppm): 0.96 (q, 1H), 1.12 (quin, 1H), 1.88 (m, 1H), 2.36 (m, 1H), 3.80 (s, 3H), 3.90 (s, 2H), 6.88 (q, 2H), 6.98 (d, 2H), 7.12 (d, 1H), 7.21 (q, 4H). MS (M+H): 257.1

Example 41

3-(((trans)-2-phenylcyclopropylamino)methyl)pyridin-2-amine

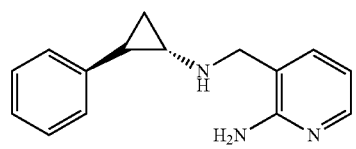

¹H-NMR (CDCl3) δ (ppm): 1.01 (q, 1H), 1.08 (quin, 1H), 1.98 (m, 1H), 2.34 (m, 1H), 3.86 (s, 2H), 5.44 (br, 2H), 6.56 (t, 1H), 6.92 (d, 2H), 7.14 (t, 1H), 7.24 (t, 3H), 7.98 (d, 1H). MS (M+H): 240.0

Example 42

(trans)-N-((2-chloropyridin-3-yl)methyl)-2-phenylcyclopropanamine

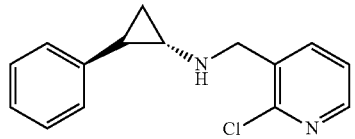

¹H-NMR (CDCl3) δ (ppm): 1.01 (q, 1H), 1.16 (quin, 1H), 1.98 (m, 1H), 2.36 (m, 1H), 3.99 (s, 2H), 6.99 (d, 2H), 7.18 (m, 2H), 7.26 (d, 2H), 7.72 (q, 1H), 8.30 (d, 1H). MS (M+H): 259.0//260.9

Example 43

(trans)-N-(3,4-dimethoxybenzyl)-2-phenylcyclopropanamine

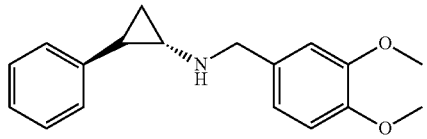

¹H-NMR (CDCl3) δ (ppm): 0.98 (q, 1H), 1.14 (quin, 1H), 1.94 (m, 1H), 2.36 (m, 1H), 3.76 (s, 3H), 3.84 (s, 2H), 3.88 (s, 3H), 6.80 (m, 3H), 7.00 (d, 2H), 7.14 (t, 1H), 7.23 (d, 2H). MS (M+H): 284.1

Example 44

(trans)-N-((2,3-dihydrobenzofuran-5-yl)methyl)-2-phenylcyclopropanamine hydrochloride

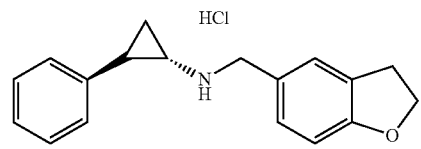

¹H-NMR (DMSO-d6) δ (ppm): 1.24 (q, 1H), 1.48 (quin, 1H), 2.40 (m, 1H), 2.84 (br, 1H), 3.10 (q, 2H), 4.16 (s, 2H), 4.52 (t, 2H), 6.76 (d, 1H), 7.09 (d, 2H), 7.22 (q, 2H), 7.28 (t, 2H), 7.34 (s, 1H), 9.50 (br, 2H). MS (M+H): 266.1

Example 45

(trans)-N-(benzo[d][1,3]dioxol-5-ylmethyl)-2-phenylcyclopropanamine hydrochloride

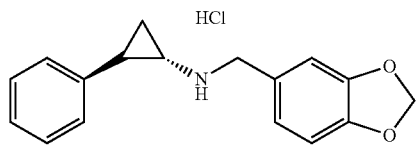

¹H-NMR (DMSO-d6) δ (ppm): 1.24 (q, 1H), 1.48 (quin, 1H), 2.44 (m, 1H), 2.82 (br, 1H), 4.18 (s, 2H), 6.02 (s, 2H), 6.92 (d, 1H), 7.09 (d, 1H), 7.12 (t, 3H), 7.20 (t, 1H), 7.27 (t, 2H), 9.60 (br, 2H). MS (M+H): 268.1

Example 46

(trans)-N-((2,3-dihydrobenzo[b][1,4]dioxin-6-yl)methyl)-2-phenylcyclopropanamine hydrochloride

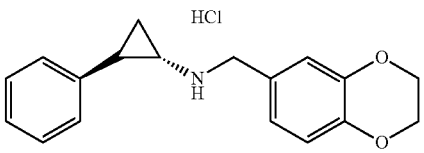

¹H-NMR (DMSO-d6) δ (ppm): 1.24 (q, 1H), 1.48 (quin, 1H), 2.48 (br, 1H), 4.12 (br, 2H), 4.20 (s, 4H), 6.78 (d, 1H), 6.92 (d, 1H), 7.09 (s, 3H), 7.18 (t, 1H), 7.26 (t, 2H), 9.74 (br, 2H). MS (M+H): 283.0

Example 47

(trans)-N-(2,6-difluoro-4-methoxybenzyl)-2-phenyl-cyclopropanamine

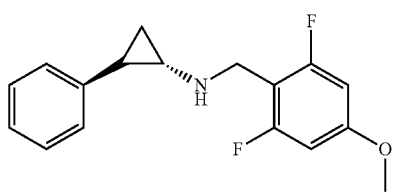

¹H-NMR (CDCl3) δ (ppm): 0.96 (q, 1H), 1.10 (quin, 1H), 1.94 (m, 1H), 2.03 (br, 1H), 2.32 (m, 1H), 3.76 (s, 3H), 3.90 (s, 2H), 6.42 (d, 2H), 7.00 (d, 2H), 7.13 (t, 1H), 7.23 (t, 2H). MS (M+H): 290.1

Example 48

(trans)-2-phenyl-N-(4-(trifluoromethoxy)benzyl)cyclopropanamine

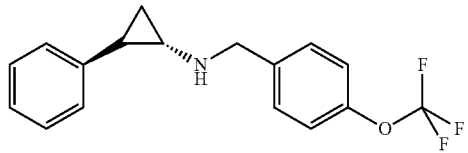

¹H-NMR (CDCl3) δ (ppm): 0.98 (q, 1H), 1.11 (quin, 1H), 1.91 (m, 1H), 1.96 (br, 1H), 2.36 (m, 1H), 3.89 (d, 2H), 6.97 (d, 2H), 7.16 (d, 3H), 7.24 (t, 2H), 7.32 (d, 2H). MS (M+H): 308.1

Example 49

(trans)-N-(5-fluoro-2-methoxybenzyl)-2-phenylcyclopropanamine

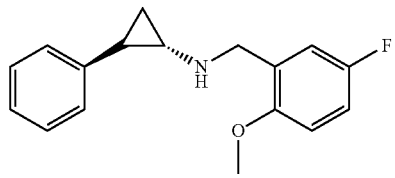

¹H-NMR (CDCl3) δ (ppm): 0.96 (q, 1H), 1.12 (quin, 1H), 1.94 (m, 1H), 2.12 (br, 1H), 2.34 (m, 1H), 3.78 (s, 3H), 3.86 (q, 2H), 6.76 (m, 1H), 6.96 (m, 4H), 7.14 (t, 1H), 7.24 (d, 2H). MS (M+H): 272.1

Example 50

(trans)-N-(2-fluoro-4-methoxybenzyl)-2-phenylcyclopropanamine

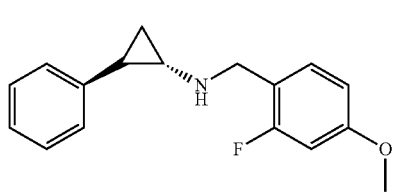

¹H-NMR (CDCl3) δ (ppm): 0.96 (q, 1H), 1.12 (quin, 1H), 1.88 (br, 1H), 1.94 (m, 1H), 2.36 (m, 1H), 3.78 (s, 3H), 3.88 (s, 2H), 6.76 (m, 2H), 6.99 (d, 2H), 7.14 (m, 2H), 7.24 (m, 2H). MS (M+H): 272.1

Example 51

(trans)-N-((4-methoxynaphthalen-1-yl)methyl)-2-phenylcyclopropanamine

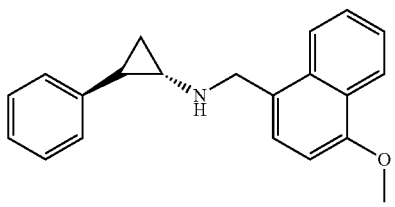

¹H-NMR (CDCl3) δ (ppm): 1.00 (q, 1H), 1.16 (quin, 1H), 1.86 (br, 1H), 1.98 (m, 1H), 2.46 (m, 1H), 3.98 (s, 3H), 4.27 (s, 2H), 6.70 (d, 1H), 6.99 (d, 2H), 7.14 (t, 1H), 7.24 (d, 2H), 7.32 (d, 1H), 7.50 (m, 2H), 8.06 (d, 1H), 8.30 (d, 1H). MS (M+H): 304.1

Example 52

(trans)-N-(2-fluoro-6-methoxybenzyl)-2-phenylcyclopropanamine

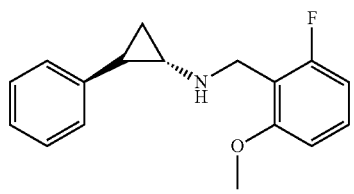

¹H-NMR (CDCl3) δ (ppm): 0.96 (q, 1H), 1.12 (quin, 1H), 1.92 (m, 1H), 2.10 (br, 1H), 2.30 (m, 1H), 3.72 (s, 3H), 3.96 (s, 2H), 6.66 (m, 2H), 6.99 (d, 2H), 7.14 (m, 2H), 7.22 (m, 2H). MS (M+H): 272.1

Example 53

(trans)-N-((2-methoxynaphthalen-1-yl)methyl)-2-phenylcyclopropanamine

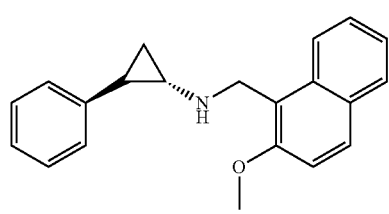

¹H-NMR (CDCl3) δ (ppm): 0.96 (q, 1H), 1.20 (quin, 1H), 1.92 (br, 1H), 1.96 (m, 1H), 2.40 (m, 1H), 3.84 (s, 3H), 4.38 (s, 2H), 6.98 (d, 2H), 7.12 (t, 1H), 7.24 (m, 3H), 7.32 (t, 1H), 7.40 (t, 1H), 7.80 (d, 2H), 8.02 (d, 1H). MS (M+H): 304.1

Example 54

(trans)-N-((4,7-dimethoxynaphthalen-1-yl)methyl)-2-phenylcyclopropanamine

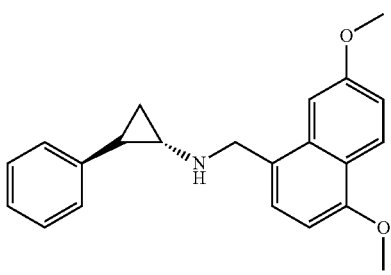

¹H-NMR (CDCl3) δ (ppm): 1.01 (q, 1H), 1.20 (quin, 1H), 1.80 (br, 1H), 2.00 (m, 1H), 2.48 (m, 1H), 3.92 (s, 3H), 3.96 (s, 3H), 4.24 (s, 2H), 6.60 (d, 1H), 7.01 (d, 2H), 7.16 (t, 2H), 7.24 (m, 2H), 7.30 (m, 1H), 7.36 (s, 1H), 8.20 (d, 1H). MS (M+H): 334.0

Example 55

(trans)-N-(4-methoxy-3-methylbenzyl)-2-phenylcyclopropanamine hydrochloride

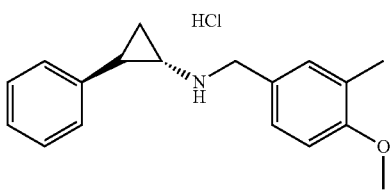

¹H-NMR (DMSO-d6) δ (ppm): 1.26 (q, 1H), 1.50 (quin, 1H), 2.06 (s, 3H), 2.80 (br, 1H), 3.76 (s, 3H), 4.16 (s, 2H), 6.94 (d, 1H), 7.10 (d, 2H), 7.28 (m, 5H), 9.50 (br, 2H). MS (M+H): 268.0

Example 56

(trans)-N-(3-chloro-4-methoxybenzyl)-2-phenylcyclopropanamine

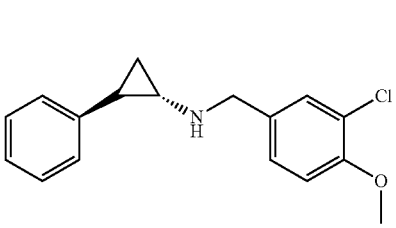

¹H-NMR (CDCl3) δ (ppm): 0.98 (q, 1H), 1.10 (quin, 1H), 1.90 (m, 2H), 2.36 (m, 1H), 3.80 (s, 2H), 3.90 (s, 3H), 6.86 (d, 1H), 7.00 (d, 2H), 7.16 (t, 2H), 7.24 (d, 2H), 7.32 (s, 1H). MS (M+H): 287.9

Example 57

(trans)-N-(3-fluoro-4-methoxybenzyl)-2-phenylcyclopropanamine

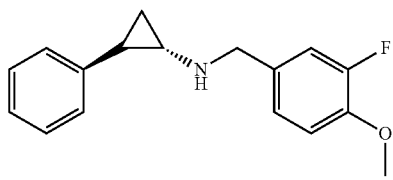

¹H-NMR (CDCl3) δ (ppm): 0.96 (q, 1H), 1.10 (quin, 1H), 1.92 (m, 2H), 2.36 (m, 1H), 3.80 (s, 2H), 3.88 (s, 3H), 6.90 (t, 1H), 6.99 (d, 3H), 7.06 (d, 1H), 7.16 (d, 1H), 7.24 (d, 2H). MS (M+H): 271.96

Example 58

(trans)-N-(4-methoxy-2-methylbenzyl)-2-phenylcyclopropanamine

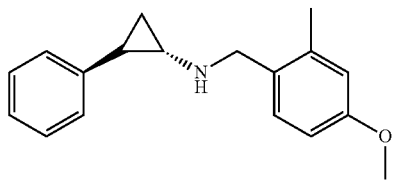

¹H-NMR (CDCl3) δ (ppm): 0.98 (q, 1H), 1.12 (quin, 1H), 1.82 (br, 1H), 1.94 (m, 1H), 2.34 (s, 3H), 2.40 (m, 1H), 3.78 (s, 3H), 3.82 (s, 2H), 6.68 (d, 1H), 6.72 (s, 1H), 7.01 (d, 2H), 7.14 (t, 2H), 7.24 (d, 2H). MS (M+H): 268.0

Example 59

(trans)-N-((3,4-dihydro-2H-benzo[b][1,4]dioxepin-6-yl)methyl)-2-phenylcyclopropanamine

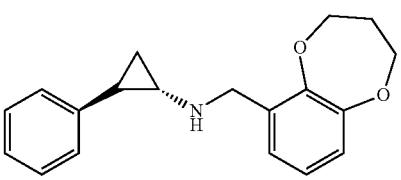

¹H-NMR (CDCl3) δ (ppm): 0.98 (q, 1H), 1.14 (quin, 1H), 1.86 (br, 1H), 1.90 (m, 1H), 2.18 (m, 2H), 2.36 (m, 1H), 3.88 (s, 2H), 4.20 (s, 4H), 6.88 (m, 3H), 7.00 (d, 2H), 7.14 (t, 1H), 7.24 (d, 2H). MS (M+H): 295.9

Example 60

(trans)-N-((3,4-dihydro-2H-benzo[b][1,4]dioxepin-7-yl)methyl)-2-phenylcyclopropanamine hydrochloride

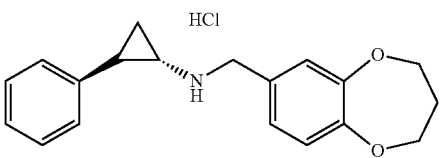

¹H-NMR (DMSO-d6) δ (ppm): 1.25 (q, 1H), 1.46 (m, 1H), 2.08 (m, 2H), 2.38 (m, 1H), 2.88 (m, 1H), 4.10 (m, 4H), 4.17 (s, 2H), 6.96 (d, 1H), 7.10 (m, 3H), 7.13 (s, 1H), 7.19 (t, 1H), 7.26 (t, 2H), 9.38 (br, 2H). MS (M+H): 295.9

Example 61

(trans)-N-((2,2-dimethylchroman-6-yl)methyl)-2-phenylcyclopropanamine

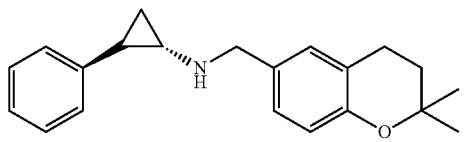

¹H-NMR (CDCl3) δ (ppm): 0.96 (q, 1H), 1.14 (quin, 1H), 1.32 (s, 6H), 1.78 (t, 2H), 1.94 (m, 2H), 2.38 (m, 1H), 2.70 (t, 3H), 3.78 (s, 2H), 6.72 (d, 1H), 7.00 (m, 4H), 7.14 (t, 1H), 7.24 (d, 2H). MS (M+H): 308.1

Example 62

(trans)-N-(4-methoxy-2,3-dimethylbenzyl)-2-phenylcyclopropanamine hydrochloride

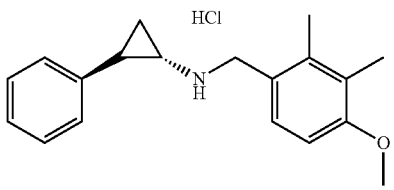

¹H-NMR (DMSO-d6) δ (ppm): 1.28 (q, 1H), 1.52 (quin, 1H), 2.06 (s, 3H), 2.20 (s, 3H), 2.42 (m, 1H), 2.94 (br, 1H), 3.76 (s, 3H), 4.26 (s, 2H), 6.84 (d, 1H), 7.09 (d, 2H), 7.20 (t, 1H), 7.28 (d, 3H), 9.32 (br, 2H). MS (M+H): 282.1

Example 63

(trans)-N-(4-methoxy-2,5-dimethylbenzyl)-2-phenyl-cyclopropanamine

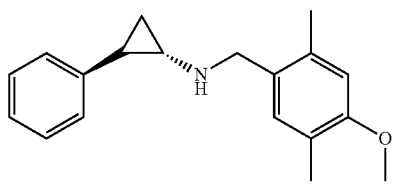

¹H-NMR (CDCl3) δ (ppm): 0.98 (q, 1H), 1.14 (quin, 1H), 1.82 (br, 1H), 1.94 (m, 1H), 2.12 (s, 3H), 2.32 (s, 3H), 2.38 (m, 1H), 3.80 (s, 5H), 6.62 (s, 1H), 6.97 (s, 1H), 7.01 (d, 2H), 7.14 (t, 1H), 7.24 (d, 2H). MS (M+H): 282.1

Example 64

(trans)-N-(2-fluoro-4,5-dimethoxybenzyl)-2-phenyl-cyclopropanamine

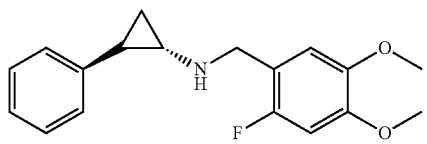

¹H-NMR (CDCl3) δ (ppm): 0.96 (q, 1H), 1.14 (quin, 1H), 1.92 (br, 1H), 2.00 (br, 1H), 2.34 (br, 1H), 3.68 (s, 2H), 3.84 (s, 6H), 6.60 (d, 1H), 6.70 (d, 1H), 6.99 (d, 2H), 7.14 (q, 1H), 7.24 (m, 2H). MS (M+H): 301.99

Example 65

(trans)-N-(3-chloro-4,5-dimethoxybenzyl)-2-phenyl-cyclopropanamine hydrochloride

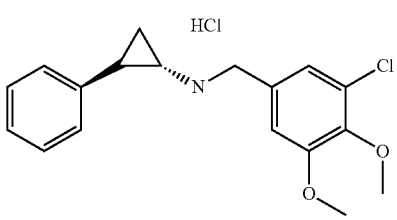

¹H-NMR (DMSO-d6) δ (ppm): 1.28 (q, 1H), 1.48 (m, 1H), 2.36 (m, 1H), 2.88 (m, 1H), 3.72 (s, 6H), 4.24 (s, 2H), 7.08 (d, 2H), 7.20 (s, 2H), 7.28 (d, 3H). MS (M+H): 318.0

Example 66

(trans)-N-(2-chloro-3,4-dimethoxybenzyl)-2-phenyl-cyclopropanamine

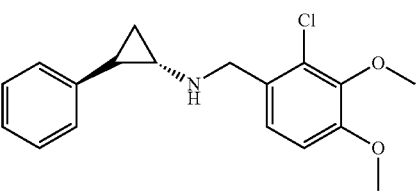

¹H-NMR (CDCl3) δ (ppm): 0.98 (q, 1H), 1.16 (quin, 1H), 2.00 (m, 1H), 2.36 (m, 1H), 3.88 (s, 6H), 3.96 (s, 2H), 6.76 (d, 1H), 7.02 (m, 3H), 7.16 (t, 1H), 7.24 (d, 2H). MS (M+H): 318.0

Example 67

(trans)-N-(2,4-dimethoxy-6-methylbenzyl)-2-phenyl-cyclopropanamine hydrochloride

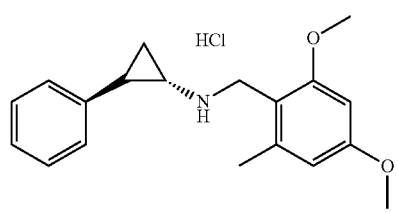

¹H-NMR (DMSO-d6) δ (ppm): 1.28 (q, 1H), 1.48 (quin, 1H), 2.32 (s, 3H), 2.38 (m, 1H), 2.90 (m, 1H), 3.72 (s, 3H), 3.76 (s, 3H), 4.14 (s, 2H), 6.42 (s, 2H), 7.11 (d, 2H), 7.22 (t, 1H), 7.28 (t, 2H), 8.96 (br, 2H). MS (M+H): 298.0

Example 68

(trans)-N-(2,5-dimethoxybenzyl)-2-phenylcyclopropanamine hydrochloride

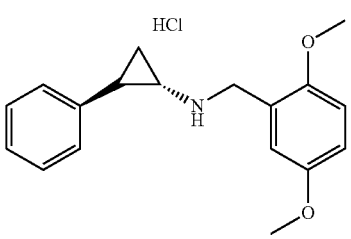

¹H-NMR (DMSO-d6) δ (ppm): 1.22 (q, 1H), 1.48 (quin, 1H), 2.36 (m, 1H), 2.80 (m, 1H), 3.68 (s, 6H), 4.16 (s, 2H), 6.92 (s, 2H), 7.08 (m, 3H), 7.18 (t, 1H), 7.28 (t, 2H), 9.30 (br, 2H). MS (M+H): 284.0

Example 69

(trans)-N-(2,3-dimethoxybenzyl)-2-phenylcyclopropanamine hydrochloride

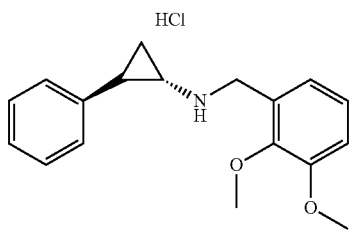

¹H-NMR (DMSO-d6) δ (ppm): 1.26 (q, 1H), 1.46 (quin, 1H), 2.38 (m, 1H), 2.88 (m, 1H), 3.76 (s, 3H), 3.80 (s, 3H), 4.21 (s, 2H), 7.09 (t, 5H), 7.20 (t, 1H), 7.26 (t, 2H). MS (M+H): 284.0

Example 70

(trans)-N-(2-chloro-3-methoxybenzyl)-2-phenylcyclopropanamine hydrochloride

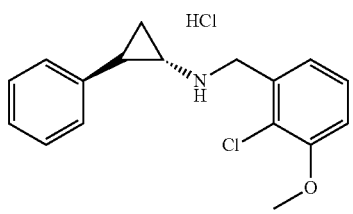

¹H-NMR (DMSO-d6) δ (ppm): 1.28 (q, 1H), 1.56 (quin, 1H), 2.48 (m, 1H), 2.92 (m, 1H), 3.86 (s, 3H), 4.37 (s, 2H), 7.09 (d, 2H), 7.21 (t, 2H), 7.28 (t, 3H), 7.37 (t, 1H). MS (M+H): 287.9

Example 71

(trans)-N-((1H-indol-5-yl)methyl)-2-phenylcyclopropanamine hydrochloride

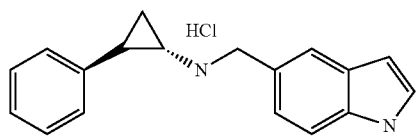

¹H-NMR (DMSO-d6) δ (ppm): 1.26 (q, 1H), 1.50 (quin, 1H), 2.48 (m, 1H), 2.86 (m, 1H), 3.86 (s, 3H), 4.32 (s, 2H), 6.40 (s, 1H), 7.09 (d, 2H), 7.24 (m, 4H), 7.38 (t, 2H), 7.67 (s, 1H), 9.46 (br, 1H). MS (M+H): 287.9

Following examples have been synthesized using the procedure described for Example 28 and the corresponding starting materials.

Example 72

(trans)-2-(4-(benzyloxy)phenyl)-N-(pyridin-2-ylmethyl)cyclopropanamine

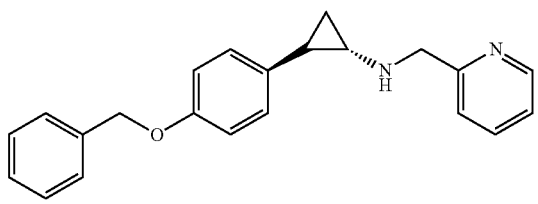

¹H-NMR (CD3OD) δ (ppm): 0.91 (q, 1H), 1.02 (quin, 1H), 1.84 (m, 1H), 2.22 (m, 1H), 3.96 (s, 2H), 5.02 (s, 2H), 6.87 (q, 4H), 7.38 (m, 8H), 7.78 (t, 1H), 8.49 (d, 1H). MS (M+H): 331.1

Example 73

(trans)-2-(4-(benzyloxy)phenyl)-N-(2-methoxybenzyl)cyclopropanamine

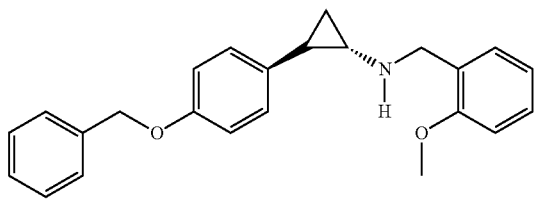

¹H-NMR (CD3OD) δ (ppm): 1.29 (q, 1H), 1.38 (quin, 1H), 2.27 (m, 1H), 2.84 (m, 1H), 3.78 (s, 3H), 4.33 (s, 2H), 5.04 (s, 2H), 6.96 (m, 6H), 7.36 (m, 7H). MS (M+H): 360.3

Example 74

(trans)-N-(1-(4-methoxyphenyl)ethyl)-2-phenylcyclopropanamine

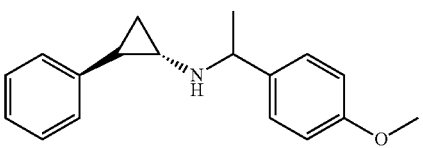

1-(4-methoxyphenyl)ethanone (138 mg, 0.75 mmol) and molecular sieve (3 A—previously activated by microwaves) was added to a solution of (trans)-2-phenylcyclopropanamine hydrochloride in 2 mL of MeOH anh., HCl 2N in dioxane (2 drops) was added and the reaction was stirred at room temperature for 3 hours. The reaction was cooled to 0° C. and NaBH₃CN (99 mg, 1.5 mmol) was added. It was stirred overnight at room temperature.

A solution of NH₄Cl sat. (2 mL) was added. After removal of the solvent the crude was dissolved in CH2Cl2 and washed with a aqueous saturated solution of NH₄Cl. It was finally washed with brine and the extracted organic layer was dried over MgSO4 anh. The crude was purified by chromatography using Hexane-AcOEt (80:20 to 70:30 in 10 min) to get colourless oil, 102 mg (yield=48.1%)

¹H-NMR (CDCl3) δ (ppm): 0.90 (q, 1H), 0.96 (quin, 1H), 1.42 (s, 3H), 2.00 (br, 1H), 2.20 (m, 1H), 3.78 (d, 3H), 3.92 (m, 1H), 6.84 (q, 3H), 7.00 (d, 1H), 7.16 (m, 2H), 7.24 (d, 3H). MS (M+H): 268.0

Following examples have been synthesized using the procedure described for Example 74 and the corresponding starting materials.

Example 75

(trans)-N-(1-(3,4-dimethoxyphenyl)ethyl)-2-phenyl-cyclopropanamine

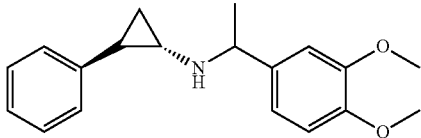

¹H-NMR (CDCl3) δ (ppm): 0.94 (m, 1H), 1.08 (br, 1H), 1.40 (s, 3H), 1.76 (br, 2H), 2.20 (m, 1H), 3.76 (s, 1H), 3.85 (t, 6H), 6.80 (m, 4H), 7.00 (d, 1H), 7.18 (m, 3H). MS (M+H): 298.0

Example 76

(trans)-N-(1-(2,3-dihydrobenzo[b][1,4]dioxin-6-yl)ethyl)-2-phenylcyclopropanamine

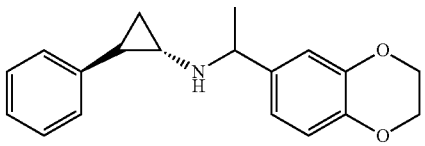

¹H-NMR (CDCl3) δ (ppm): 0.90-0.96 (m, 1H), 1.08 (br, 1H), 1.38 (d, 3H), 1.84-1.96 (br, 1H), 2.19-2.23 (m, 1H), 3.84 (m, 1H), 4.24 (s, 4H), 6.82 (m, 4H), 7.00 (d, 1H), 7.20 (m, 3H). MS (M+H): 296.0

Example 77

(trans)-N-(1-(5-fluoro-2-methoxyphenyl)ethyl)-2-phenylcyclopropanamine

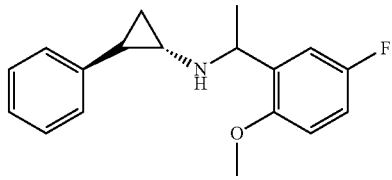

¹H-NMR (CDCl3) δ (ppm): 0.92 (q, 1H), 1.06 (m, 1H), 1.36 (d, 3H), 1.80-1.92 (m, 1H), 2.18 (m, 1H), 3.70 (s, 3H), 4.22-4.28 (m, 1H), 6.74 (m, 1H), 6.86 (m, 2H), 6.99 (m, 2H), 7.12 (m, 1H), 7.20 (m, 2H). MS (M+H): 286.0

Example 78

(trans)-N-(1-(3,4-dimethoxyphenyl)propan-2-yl)-2-phenylcyclopropanamine

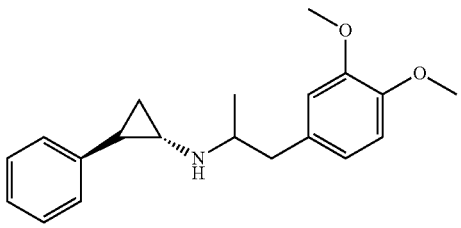

¹H-NMR (CDCl3) δ (ppm): 0.96 (q, 1H), 1.06 (m, 1H), 1.14 (d, 3H), 1.79-1.86 (m, 1H), 2.18-2.32 (m, 1H), 2.63-2.71 (m, 2H), 3.04 (m, 1H), 3.85 (d, 6H), 6.70 (m, 2H), 6.79 (d, 1H), 7.02 (m, 2H), 7.13 (m, 1H), 7.23 (m, 2H). MS (M+H): 312.1

Example 79

(trans)-N-((3-methyl-1,2,4-oxadiazol-5-yl)methyl)-2-phenylcyclopropanamine hydrochloride

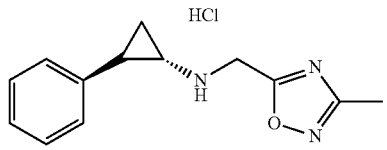

Step 1:

N,N-Diisopropylethylamine (3 mL, 17.16 mmol) was added to a solution of (trans)-2-phenylcyclopropanamine hydrochloride (1.5 g, 8.58 mmol) in 70 mL of CH₃CN. After complete dissolution of the amine the methyl 2-bromoacetate (930 μL, 9.44 mmol) was added and then stirred overnight at room temperature. After solvent removal the crude was purified by flash chromatography eluting with CH₂Cl₂/MeOH (99:1 to 90:10) to get methyl 2-((trans)-2-phenylcyclopropylamino)acetate as colourless oil (1.76 g, Yield=100%).

Step 2:

A solution of LiOH (432 mg, 10.30 mmol) in 17 mL of H₂O was added to the solution of methyl 2-((trans)-2-phenylcyclopropylamino)acetate (1.76 g, 8.58 mmol) in 70 mL de THF and it was stirred vigorously for 2 hours at room temperature. Di-tert-butyl dicarbonate (2.7 g, 12 mmol) was added and stirred for 3 hours. After solvent removal the crude was solved in 60 mL of AcOEt and washed with 40 mL of brine. The organic layer was dried over MgSO4 anh., filtered and the solvent was removed. The crude was purified by flash chromatography eluting with CH2Cl2/MeOH (98:2 to 90:10) to get 2-(tert-butoxycarbonyl((trans)-2-phenylcyclopropyl)amino)acetic acid as colourless oil (2.08 g. Yield=83.3%).

Step 3:

EDC (107 µL, 0.585 mmol) and acetoamidoxime (41 mg, 0.532 mmol) was added to a stirred solution of 2-(tert-butoxycarbonyl((trans)-2-phenylcyclopropyl)amino)acetic acid (163 mg, 0.532 mmol) in diglyme (2 mL) under argon atmosphere. The mixture was stirred at 50° C. overnight and then at 110° C. for 14 hours. After removal of solvent under vacuum, the reaction mixture was purified by flash chromatography eluting with hexane/MTBE (80:20 to 0:100) to afford tert-butyl (3-methyl-1,2,4-oxadiazol-5-yl)methyl((1S,2S)-2-phenylcyclopropyl)carbamate as a colourless oil (35 mg. Yield=20%).

Step 4:

HCl 2N in $Et_2O$ was added to tert-butyl (3-methyl-1,2,4-oxadiazol-5-yl)methyl((1S,2S)-2-phenylcyclopropyl)carbamate (35 mg, 0.106 mmol). The $Et_2O$ was decanted and the solid was washed twice with 5 mL of $Et_2O$. The solid was dried by vacuum to get (trans)-N-((3-methyl-1,2,4-oxadiazol-5-yl)methyl)-2-phenylcyclopropanamine hydrochloride (14 mg. Yield 12.8%)

$^1$H-NMR (DMSO-d6) δ (ppm): 1.28 (q, 1H), 1.52 (quin, 1H), 2.35 (s, 3H), 3.00 (m, 1H), 4.71 (s, 2H), 7.12 (d, 2H), 7.20 (t, 1H), 7.28 (t, 2H). MS (M+H): 229.9

Example 80

Biological Assays—LSD1

The compounds of the invention can be tested for their ability to inhibit LSD1. The ability of the compounds of the invention to inhibit LSD1 can be tested as follows. Human recombinant LSD1 protein was purchased from BPS Bioscience Inc. In order to monitor LSD1 enzymatic activity and/or its inhibition rate by our inhibitor(s) of interest, di-methylated H3-K4 peptide (Millipore) was chosen as a substrate. The demethylase activity was estimated, under aerobic conditions, by measuring the release of $H_2O_2$ produced during the catalytic process, using the Amplex® Red peroxide/peroxidase-coupled assay kit (Invitrogen).

Briefly, a fixed amount of LSD1 was incubated on ice for 15 minutes, in the absence and/or in the presence of various concentrations of inhibitor (from 0 to 75 µM, depending on the inhibitor strength). Tranylcypromine (Biomol International) was used as a control for inhibition. Within the experiment, each concentration of inhibitor was tested in triplicate. After leaving the enzyme interacting with the inhibitor, 12.5 µM of di-methylated H3-K4 peptide was added to each reaction and the experiment was left for 1 hour at 37° C. in the dark. The enzymatic reactions were set up in a 50 mM sodium phosphate, pH 7.4 buffer. At the end of the incubation, Amplex® Red reagent and horseradish peroxidase (HPR) solution were added to the reaction according to the recommendations provided by the supplier (Invitrogen), and left to incubate for 30 extra minutes at room temperature in the dark. A 1 µM $H_2O_2$ solution was used as a control of the kit efficiency. The conversion of the Amplex® Red reagent to resorufin due to the presence of $H_2O_2$ in the assay, was monitored by fluorescence (excitation at 540 nm, emission at 590 nm) using a microplate reader (Infinite 200, Tecan). Arbitrary units were used to measure level of $H_2O_2$ produced in the absence and/or in the presence of inhibitor.

The maximum demethylase activity of LSD1 was obtained in the absence of inhibitor and corrected for background fluorescence in the absence of LSD1. The Ki of each inhibitor was estimated at half of the maximum activity.

A number of the compounds of the invention were tested for their ability to inhibit LSD1 and were found to have Ki values lower than 100 µM, including many of the compounds in examples that were tested. Compound of examples 3 and 17, were found to have Ki values for LSD1 of less than 10 µM. Compounds of examples 1, 8, 9, 11 were found to have Ki values for LSD1 of less than 1 micromolar. Parnate (2-trans phenylcyclopropylamine) was found to have a Ki of from about 15 to 35 micromolar depending on the enzyme preparation.

Previous studies reported in the literature indicated that substitutions on the amine group of phenylcyclopropylamines reduced the ability of the compound to inhibit monoamine oxidases, which have significant structural homology to LSD1. For example Zirkle et al. ((1962) J. Med. Chem. 1265-1284) found that a methyl substituent on the amine group decreased activity slightly whereas substitution with larger alkyl groups and groups bearing ring system like aralkyls reduced MAO activity substantially. The inventors of the instant invention have surprisingly found that ring bearing substitutions on the amine group of phenylcyclopropyl amine produce potent LSD1 inhibitors.

Previous reports of LSD1 have found that it is involved in cell proliferation and growth. Some studies have implicated LSD1 as a therapeutic target for cancer. Huang et al. (2007) *PNAS* 104:8023-8028 found that polyamines inhibitors of LSD1 modestly cause the reexpression of genes aberrantly silenced in cancer cells and particularly colorectal cancer (Huang et al. *Clin Cancer Res.* (2009) December 1; 15(23): 7217-28. Epub 2009 Nov. 24. PMID: 19934284). Scoumanne et al. ((2007) *J. Biol. Chem.* May 25; 282(21):15471-5) found that deficiency in LSD1 leads to a partial cell cycle arrest in G2/M and sensitizes cells to growth suppression induced by DNA damage. Kahl et al. ((2006) *Cancer Res.* 66(23):11341-7) found that LSD1 expression is correlated with prostate cancer aggressiveness. Metzger et al. reported that LSD1 modulation by siRNA and pargyline regulates androgen receptor (AR) and may have therapeutic potential in cancers where AR plays a role, like prostate, testis, and brain cancers. Lee et al. ((2006) *Chem. Biol.* 13:563-567) reported that tranylcypromine derepresses Egr-1 gene expression in some cancer lines. A body of evidence is accumulating that Egr-1 is a tumor suppressor gene in many contexts (see e.g., Calogero et al. (2004) *Cancer Cell International* 4:1 exogenous expression of EGR-1 resulted in growth arrest and eventual cell death in primary cancer cell lines; Lucerna et al. (2006) *Cancer Research* 66, 6708-6713 show that sustained expression of Egr-1 causes antiangiogenic effects and inhibits tumor growth in some models; Ferraro et al. ((2005) *J. Clin. Oncol.* March 20; 23(9):1921-6) reported that Egr-1 is downregulated in lung cancer patients with a higher risk of recurrence and may be more resistant to therapy. Thus, increasing Egr-1 expression via inhibition of LSD1 is a therapeutic approach for some cancers. Recent studies have also implicated LSD1 in brain cancer (Schulte et al. (2009) Cancer Res. March 1; 69(5):2065-71). Other studies have implicated LSD1 in breast cancer (Lims et al. Carcinogenesis. 2009 Dec. 30. [Epub ahead of print] PMID: 20042638).

Thus, a body of evidence has implicated LSD1 in a number of cancers, which suggests that LSD1 is a therapeutic target for cancer. The instant inventors have discovered a class of LSD1 inhibitors that can be used to treat diseases where LSD1 is implicated as a therapeutic target like cancer. According, the phenylcyclopropylamine compounds of the invention can be used to treat and/or prevent such diseases.

Example 81

Biological Assays—Monoamine Oxidase Assays

Human recombinant monoamine oxidase proteins MAO-A and MAO-B were purchased from Sigma Aldrich.

MAOs catalyze the oxidative deamination of 1°, 2° and 3° amines. In order to monitor MAO enzymatic activities and/or their inhibition rate by inhibitor(s) of interest, a fluorescent-based (inhibitor)-screening assay was set up. 3-(2-Aminophenyl)-3-oxopropamamine (kynuramine dihydrobromide, Sigma Aldrich), a non fluorescent compound was chosen as a substrate. Kynuramine is a non-specific substrate for both MAOs activities. While undergoing oxidative deamination by MAO activities, kynuramine is converted into 4-hydroxyquinoline (4-HQ), a resulting fluorescent product.

The monoamine oxidase activity was estimated by measuring the conversion of kynuramine into 4-hydroxyquinoline. Assays were conducted in 96-well black plates with clear bottom (Corning) in a final volume of 100 µL. The assay buffer was 100 mM HEPES, pH 7.5. Each experiment was performed in triplicate within the same experiment.

Briefly, a fixed amount of MAO (0.25 µg for MAO-A and 0.5 µg for MAO-B) was incubated on ice for 15 minutes in the reaction buffer, in the absence and/or in the presence of various concentrations of inhibitor (from 0 to 50 µM, depending on the inhibitor strength). Tranylcypromine (Biomol International) was used as a control for inhibition.

After leaving the enzyme(s) interacting with the inhibitor, 60 to 90 µM of kynuramine was added to each reaction for MAO-B and MAO-A assay respectively, and the reaction was left for 1 hour at 37° C. in the dark. The oxidative deamination of the substrate was stopped by adding 50 µL (v/v) of NaOH 2N. The conversion of kynuramine to 4-hydroxyquinoline, was monitored by fluorescence (excitation at 320 nm, emission at 360 nm) using a microplate reader (Infinite 200, Tecan). Arbitrary units were used to measure levels of fluorescence produced in the absence and/or in the presence of inhibitor.

The maximum of oxidative deamination activity was obtained by measuring the amount of 4-hydroxyquinoline formed from kynuramine deamination in the absence of inhibitor and corrected for background fluorescence in the absence of MAO enzymes. The Ki of each inhibitor was measure at Vmax/2.

Using the above described assay a number of the compounds of the invention were tested for their ability to inhibit MAO-B and were found to have Ki values lower than 100 µM, including many of the compounds in examples tested. Compound of examples 1, 4, 16, 11, and 17 were found to have Ki (IC50) values for MAO-B of less than 100 µM. Trans-2-phenylcyclopropylamine(tranylcypromine) was found to have a Ki for MAO-A of about 2 micromolar and a Ki of about 0.6 micromolar for MAO-B.

Previous reports in the literature (Zirkle et al. (1962) J. Med. Chem. 1265-1284) indicated that substitutions on the amine group of phenylcyclopropylamine with small alkyl groups like methyl reduce MAO inhibitory activity slightly whereas disubstitution of the amine with methyl or mono substitution with larger ring bearing substituents like benzyl reduce MAO inhibitory activity substantially. The inventors of the instant invention found that larger ring bearing substituents on the amine group of phenylcyclopropylamine could produce potent inhibitors of monoamine oxidases and particularly MAO-B.

A number of the compounds of the invention were tested for their ability to inhibit MAO-A using the above described assay and were found to have Ki values for MAO-A higher than that for MAO-B (i.e., inhibit MAO-B better than MAO-A) e.g., like the compounds of Examples 11 and 13 which both a better MAO-B inhibitors than MAO-A inhibitors which MAO-B IC50 values below 50 micromolar.

Thus, unexpectedly compounds having large ring bearing substituents on the amine group of phenylcyclopropylamine were found to be potent LSD1 inhibitors as well as potent MAO-B inhibitors.

The invention therefore provides inhibitors selective for LSD1. LSD1 selective inhibitors have IC50 values for LSD1 which are at least 2-fold lower than the IC50 value for MAO-A and/or MAO-B. One example of an LSD1 selective inhibitor is given in Example 2 which has an IC50 for LSD1 which is about 10-fold lower than for MAO-A and MAO-B. Another example of an LSD1 selective inhibitor is in Example 16 which has an IC50 for LSD1 which is more than 5-fold lower than the IC50 for MAO-A and MAO-B. Yet another example of a selective LSD1 inhibitor is given in Example 17 which has an IC50 which is more than 3-fold lower for LSD1 than MAO-A and MAO-B.

The invention also provides dual inhibitors selective for LSD1 and MAO-B. Dual LSD1/MAO-B selective inhibitors have IC50 values for LSD1 and MAO-B which are at least 2-fold lower than the IC50 value for MAO-A. One example of a dual LSD1/MAO-B selective inhibitor is given in Example 11 which has an IC50 for LSD1 and MAO-B which is about 2-fold lower than for MAO-A. Another example of a dual LSD1/MAO-B inhibitor is given in Example 7 where the MAO-B IC50 is less than half the value it is for MAO-A and the LSD1 IC50 is about 1 micromolar.

TABLE 1

IC50 Values (micromolar) for Selected Examples

| Example Compound No. | MAO-A | MAO-B | LSD1 |
|---|---|---|---|
| 2 | 10 | 10 | 0.8 |
| 4 | 1.4 | 7 | 0.33 |
| 6 | 3.2 | 1 | 2.8 |
| 7 | 31 | 11 | 1 |
| 8 | 13 | 13 | 0.21 |
| 9 | 39 | 17 | 0.7 |
| 10 | 29 | 14 | 0.7 |
| 11 | >50 | 28 | 0.8 |
| 12 | nd | nd | 4.5 |
| 16 | 18 | 16 | 2.0 |
| 17 | 16 | 10 | 2.3 |
| 19 | 3 | 4 | 0.4 |
| 20 | 1 | 2 | 0.28 |
| 21 | 3 | 6 | 0.41 |
| 22 | 12 | 8 | 0.5 |
| 23 | 1.7 | 2.3 | 0.74 |
| 24 | nd | nd | 4.6 |
| 25 | 12.8 | 5.33 | 0.21 |
| 29 | 3 | 3 | 4.6 |
| 30 | 9 | 6 | 3 |
| 31 | 3.8 | 3 | 0.46 |
| 32 | 5.5 | 6.1 | 1.12 |
| 33 | 33.8 | 8 | 0.55 |
| 34 | 1.2 | 1.9 | 0.14 |
| 35 | 1.6 | 3.3 | 0.18 |
| 36 | 13 | 35.5 | 0.25 |
| 37 | >>50 | 50 | 0.25 |
| 38 | 8.5 | 18.2 | 0.19 |
| 39 | 2.4 | 5.4 | 0.16 |
| 40 | 27.8 | 15.5 | 0.39 |
| 41 | 8.1 | 8.1 | 0.16 |
| 42 | >>50 | 34.3 | 0.09 |
| 43 | 2.8 | 24 | 0.06 |
| 44 | 2.5 | 2.4 | 0.30 |
| 45 | 1.8 | 2.2 | 0.40 |
| 46 | 2.4 | 3.5 | 0.67 |
| 47 | 24 | 14 | 0.96 |
| 48 | nd | nd | 4.5 |
| 49 | 37 | 9.6 | 0.30 |
| 50 | 7 | 10.4 | 0.36 |
| 51 | 24.5 | >50 | 1.95 |

TABLE 1-continued

IC50 Values (micromolar) for Selected Examples

| Example Compound No. | MAO-A | MAO-B | LSD1 |
|---|---|---|---|
| 52 | 38.8 | >>50 | 0.22 |
| 53 | 16.4 | >50 | 0.06 |
| 54 | 18.5 | >>50 | 0.05 |
| 55 | 2.8 | 21.6 | 0.45 |
| 56 | 1.8 | 9.8 | 0.51 |
| 57 | 3.4 | 8.6 | 0.51 |
| 58 | 10 | 13.8 | 0.08 |
| 59 | 26.6 | 9.5 | 0.28 |
| 60 | 1.7 | 2.5 | 0.30 |
| 61 | 7.4 | 1.5 | 0.04 |
| 62 | 21.3 | 25.3 | 0.07 |
| 63 | 8.1 | 23.8 | 0.07 |
| 64 | nd | nd | 0.21 |
| 65 | nd | nd | 0.147 |
| 66 | >>50 | 7.9 | 0.06 |
| 67 | nd | nd | nd |
| 68 | nd | nd | nd |
| 69 | nd | nd | nd |
| 70 | nd | nd | nd |
| 71 | 3 | 9.8 | 0.18 |
| 72 | 2.1 | 2.1 | 0.91 |
| 73 | 5.9 | 2.3 | 0.05 |
| 74 | nd | nd | 26% at 2.5 microM |
| 75 | nd | nd | 0.21 |
| 76 | 16 | 7.4 | 0.005 |
| 77 | nd | nd | nd |
| 78 | >50 | >50 | 0.28 |
| 79 | 38 | >50 | 0.014 |
| Tranylcypromine | 2 | 0.6 | 25 |

All results reported in Table 1 are the average of at-least two determinations of the IC50 value and usually more, unless otherwise noted, and nd signifies not determined. The IC50 LSD1 values for the inhibitors of examples 20, 21, 23, and 25 represent only one measurement.

As can be seen from Table 1, the compounds of Formula I can have IC50 values for LSD1 of less than that for parnate, less than 10 micromolar, less than 1 micromolar, and less than 500 nanomolar. Typically the IC50 values of the compounds of Formula I for LSD1 are less than 1 micromolar.

As can be seen from Table 1, the compounds of Formula I can have IC50 values for MAO-A of less than 20 micromolar, less than 10 micromolar, and less than 5 micromolar. Typically the IC50 values of the compounds of Formula I for MAO-A are greater than 1 micromolar.

As can be seen from Table 1, the compounds of Formula I can have IC50 values for MAO-B of less than 20 micromolar, less than 10 micromolar, and less than 5 micromolar. Typically the IC50 values of the compounds of Formula I for MAO-B are greater than 1 micromolar.

Most of the compounds of the Examples are selective LSD1 inhibitors in that they inhibit LSD1 to a greater extent than MAO-A and MAO-B. Some of the compounds of the Examples inhibit both MAO-B and LSD1 to a greater extent than MAO-A.

As the skilled artisan readily recognizes the compounds disclosed herein are surprisingly and significantly more potent than tranylcypromine for LSD1 inhibition. Han et al. (Euro. J. Pharma. (2008) doi:10.1016/j.ejphar.2008.12.025) reported that phenylcyclopropylamine displays neuroprotective activity in PC12 cells thus the compounds of Formula I may be used as a neuroprotectant (e.g., used to treat and/or prevent conditions characterized by neurodegeneration). Furthermore, since the compounds of Formula I are potent LSD1 inhibitor they can be used to treat and/or prevent diseases where LSD1 inhibition is desirable, e.g., cancer.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

The invention claimed is:

1. A compound of Formula I:

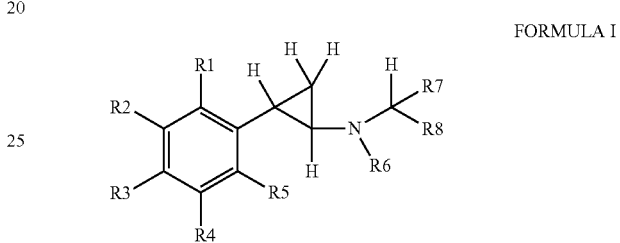

FORMULA I wherein:
each of R1-R5 is independently selected from the group consisting of —H, halo, alkyl, alkoxy, haloalkyl, and haloalkoxy, wherein the alkyl group in said alkyl, alkoxy, haloalkyl, or haloalkoxy has from 1 to 4 carbon atoms;

R6 is —H;

R7 is —H;

R8 is a -L-heterocyclyl, wherein said heterocyclyl is pyridyl, thiazolyl, hi phenyl, quinolinyl, indolyl, 2,3-dihydrobenzofuranyl, benzo[d][1,3]dioxolyl, 2,3-dihydrobenzo[b][1,4]dioxinyl, 3,4-dihydro-2H-benzo[b][1,4]dioxepinyl, or chromanyl, wherein the ring or ring system of said -L-heterocyclyl has from 1-3 substituents and wherein said 1-3 substituents are selected from the group consisting of halo, alkyl, alkoxy, haloalkyl, haloalkoxy, amino, cyano, and hydroxyl wherein the alkyl group in said alkyl, alkoxy, haloalkyl, or haloalkoxy has from 1 to 4 carbon atoms; or R8 is -L-aryl, wherein said aryl is phenyl or napthalenyl, wherein the ring or ring system of said -L-aryl has from 1-3 substituents and wherein said 1-3 substituents are selected from the group consisting of halo, alkyl, alkoxy, haloalkyl, haloalkoxy, amino, cyano, and hydroxyl, wherein the alkyl group in said alkyl, alkoxyl, haloalkyl, or haloalkoxy has from 1 to 4 carbon atoms;

L is a covalent bond or $CH_2$;

or a pharmaceutically acceptable salt thereof;

with the provision that when L is a bond and R1, R2, R3, R4, R5, R6, and R7 are all hydro, then R8 is not 2,4-dimethoxyphenyl, 4-bromophenyl, 4-methoxyphenyl, or 4-chlorophenyl.

2. The compound of claim 1, wherein R8 is an -L-heterocyclyl, wherein said heterocyclyl is pyridyl, thiazolyl, thiophenyl, quinolinyl, indolyl, 2,3-dihydrobenzofuranyl, benzo[d][1,3]dioxolyl, 2,3-dihydrobenzo[b][1,4]dioxinyl, 3,4-dihydro-2H-benzo[b][1,4]dioxepinyl, or chromanyl, wherein the ring or ring system of said -L-heterocyclyl has from 1-3 substituents and wherein said 1-3 substituents are selected from the group consisting of halo, alkyl, alkoxy, haloalkyl, haloalkoxy, amino, cyano, and hydroxyl wherein the alkyl group in said alkyl, alkoxy, haloalkyl, or haloalkoxy has from 1 to 4 carbon atoms.

3. The compound of claim 1, wherein R8 is -L-aryl, wherein said aryl is phenyl or naphthalenyl, wherein the ring or car ring system of said -L-aryl has from 1-3 substituents and wherein said 1-3 substituents are selected from the group consisting of halo, alkyl, alkoxy, haloalkyl, haloalkoxy, amino, cyano, and hydroxyl, wherein the alkyl group in said alkyl, alkoxy, haloalkyl, or haloalkoxy has from 1 to 4 carbon atoms.

4. The compound of claim 1, wherein the substituents on the cyclopropyl ring have the trans configuration.

5. The compound of claim 1 wherein said compound is selected from the group consisting of:
(trans)-N-(4-fluorobenzyl)-2-phenylcyclopropanamine;
(trans)-N-(4-fluorobenzyl)-2-phenylcyclopropanaminium;
4-(((trans)-2-phenylcyclopropylamino)methyl)benzonitrile;
(trans)-N-(4-cyanobenzyl)-2-phenylcyclopropanaminium;
(trans)-2-phenyl-N-(4-(trifluoromethyl)benzyl)cyclopropanamine;
(trans)-2-phenyl-N-(4-(trifluoromethyl)benzyl)cyclopropanaminium;
(trans)-N-((6-methylpyridin-2-yl)methyl)-2-phenylcyclopropanamine;
(trans)-N-((3-bromothiophen-2-yl)methyl)-2-phenylcyclopropanamine;
(trans)-N-((4-bromothiophen-2-yl)methyl)-2-phenylcyclopropanamine;
(trans)-N-(3,4-dichlorobenzyl)-2-phenylcyclopropanamine;
(trans)-N-(3-fluorobenzyl)-2-phenylcyclopropanaminium;
(trans)-N-(2-fluorobenzyl)-2-phenylcyclopropanamine;
(trans)-N-(3-methoxybenzyl)-2-phenylcyclopropanamine;
(trans)-2-phenyl-N-((6-(trifluoromethyl)pyridin-3-yl)methyl)cyclopropanamine;
(trans)-N-((6-chloropyridin-3-yl)methyl)-2-phenylcyclopropanamine;
(trans)-N-((4-methylpyridin-2-yl)methyl)-2-phenylcyclopropanamine;
(trans)-N-((6-methoxypyridin-2-yl)methyl)-2-phenylcyclopropanamine;
2-(((trans)-2-phenylcyclopropylamino)methyl)pyridin-3-ol;
(trans)-N-((6-bromopyridin-2-yl)methyl)-2-phenylcyclopropanamine;
(trans)-2-phenyl-N-((5-(trifluoromethyl)pyridin-2-yl)methyl)cyclopropanamine;
(trans)-N-((3-fluoropyridin-2-yl)methyl)-2-phenylcyclopropanamine;
(trans)-N-((6-methoxypyridin-3-yl)methyl)-2-phenylcyclopropanamine;
(trans)-N4(5-methoxypyridin-3-yl)methyl)-2-phenylcyclopropanamine;
(trans)-N-((2-methoxypyridin-3-yl)methyl)-2-phenylcyclopropanamine;
3-(((trans)-2-phenylcyclopropylamino)methyl)benzonitrile;
(trans)-N-(2-methoxybenzyl)-2-phenylcyclopropanamine;
3-(((trans)-2-phenylcyclopropylamino)methyl)pyridin-2-amine;
(trans)-N4(2-chloropyridin-3-yl)methyl)-2-phenylcyclopropanamine;
(trans)-N-(3,4-dimethoxybenzyl)-2-phenylcyclopropanamine;
(trans)-N-(2,6-difluoro-4-methoxybenzyl)-2-phenylcyclopropanamine;
(trans)-2-phenyl-N-(4-(trifluoromethoxy)benzyl)cyclopropanamine;
(trans)-N-(5-fluoro-2-methoxybenzyl)-2-phenylcyclopropanamine;
(trans)-N-(2-fluoro-4-methoxybenzyl)-2-phenylcyclopropanamine;
(trans)-N-((4-methoxynaphthalen-1-yl)methyl)-2-phenylcyclopropanamine;
(trans)-N-(2-fluoro-6-methoxybenzyl)-2-phenylcyclopropanamine;
(trans)-N-((2-methoxynaphthalen-1-yl)methyl)-2-phenylcyclopropanamine;
(trans)-N-((4,7-dimethoxynaphthalen-1-yl)methyl)-2-phenylcyclopropanamine;
(trans)-N-(4-methoxy-3-methylbenzyl)-2-phenylcyclopropanamine;
(trans)-N-(3-chloro-4-methoxybenzyl)-2-phenylcyclopropanamine;
(trans)-N-(3-fluoro-4-methoxybenzyl)-2-phenylcyclopropanamine;
(trans)-N-(4-methoxy-2-methylbenzyl)-2-phenylcyclopropanamine;
(trans)-N-(2,2-dimethylchroman-6-yl)methyl)-2-phenylcyclopropanamine;
(trans)-N-(4-methoxy-2,3-dimethylbenzyl)-2-phenylcyclopropanamine:
(trans)-N-(4-methoxy-2,5-dimethylbenzyl)-2-phenylcyclopropanamine;
(trans)-N-(2-fluoro-4,5-dimethoxybenzyl)-2-phenylcyclopropanamine;
(trans)-N-(3-chloro-4,5-dimethoxybenzyl)-2-phenylcyclopropanamine;
(trans)-N-(2-chloro-3,4-dimethoxybenzyl)-2-phenylcyclopropanamine;
(trans)-N-(2,4-dimethoxy-6-methylbenzyl)-2-phenylcyclopropanamine;
(trans)-N-(2,5-dimethoxybenzyl)-2-phenylcyclopropanamine;
(trans)-N-(2,3-dimethoxybenzyl)-2-phenylcyclopropanamine;
(trans)-N-(2-chloro-3-methoxybenzyl)-2-phenylcyclopropanamine; and
pharmaceutically acceptable salts of any thereof.

6. A pharmaceutical composition comprising a compound of formula I,

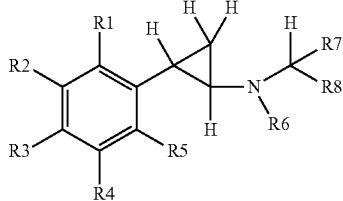

FORMULA I wherein:
each of R1-R5 is independently selected from the group consisting of —H, halo, alkyl, alkoxy, haloalkyl, and haloalkoxy, wherein the alkyl group in said alkyl, alkoxy, haloalkyl, or haloalkoxy has from 1 to 4 carbon atoms;
R6 is —H;
R7 is —H;
R8 is a -L-heterocyclyl, wherein said heterocyclyl is pyridyl, thiazolyl, thiophenyl, quinolinyl, indolyl, 2,3-dihydrobenzofuranyl, benzo[d][1,3]dioxolyl, 2,3-dihydrobenzo[b][1,4]dioxinyl, 3,4-dihydro-2H-benzo[b][1,4]dioxepinyl, or chromanyl, wherein the ring or ring system of said -L-heterocyclyl has from 0-3 substituents and wherein said 0-3 substituents are selected from the group consisting of halo, alkyl, alkoxy, haloalkyl, haloalkoxy, amino, cyano, and hydroxyl, wherein the alkyl group in said alkyl, alkoxy, haloalkyl, or haloalkoxy has from 1 to 4 carbon atoms; or
R8 is -L-aryl, wherein said aryl is phenyl or napthalenyl, wherein the ring or ring system of said -L-aryl has from 1-3 substituents and wherein said 1-3 substituents are selected from the group consisting of halo, alkyl, alkoxy, haloalkyl, haloalkoxy, amino, cyano, and hydroxyl, wherein the alkyl group in said alkyl, alkoxy, haloalkyl, or haloalkoxy has from 1 to 4 carbon atoms;
L is a covalent bond or CH$_2$;
or a pharmaceutically acceptable salt thereof;
with the provision that when L is a bond and R2, R3, R4, R5, R6, and R7 are all hydro, then R8 is not 2,4-dimethoxyphenyl, 4-bromophenyl, 4-methoxyphenyl, or 4-chlorophenyl,
and a pharmaceutically acceptable carrier.

7. The pharmaceutical composition of claim 6 wherein R8 is an -L-heterocyclyl, wherein said heterocyclyl is pyridyl, thiazolyl, thiophenyl, quinolinyl, indolyl, 2,3-dihydrobenzofuranyl, benzo[d][1,3]dioxolyl, 2,3-dihydrobenzo[b][1,4]dioxinyl, 3,4-dihydro-2H-benzo[b][1,4]dioxepinyl, or chromanyl, wherein the ring or ring system of said -L-heterocyclyl has from 0-3 substituents and wherein said 0-3 substituents are selected from the group consisting of halo, alkyl, alkoxy, haloalkyl, haloalkoxy, amino, cyano, and hydroxyl, wherein the alkyl group in said alkyl, alkoxy, haloalkyl, or haloalkoxy has from 1 to 4 carbon atoms.

8. The pharmaceutical composition of claim 6 wherein the substituents on the cyclopropyl ring have the trans configuration.

9. The compound of claim 1, wherein:
R8 is a -L-heterocyclyl, wherein said heterocyclyl is pyridyl, thiazolyl, thiophenyl, quinolinyl, indolyl, 2,3-dihydrobenzofuranyl, benzo[d][1,3]dioxolyl, 2,3-dihydrobenzo[b][1,4]dioxinyl, 3,4-dihydro-2H-benzo[b][1,4]dioxepinyl, or chromanyl, wherein the ring or ring system of said -L-heterocyclyl has from 1-3 substituents and wherein said 1-3 substituents are selected from the group consisting of halo, alkyl, alkoxy, haloalkyl, haloalkoxy, amino, cyano, and hydroxyl, wherein the alkyl group in said alkyl, alkoxy, haloalkyl, or haloalkoxy has from 1 to 4 carbon atoms; or
R8 is -L-phenyl wherein the phenyl ring of said -L-phenyl has from 1-3 substituents and wherein said 1-3 substituents are selected from the group consisting of halo, alkyl, alkoxy, haloalkyl, haloalkoxy, amino, cyano, and hydroxyl, wherein the alkyl group in said alkyl, alkoxy, haloalkyl, or haloalkoxy has from 1 to 4 carbon atoms.

10. The compound of claim 9, wherein L is a covalent bond.

11. The compound of claim 2, wherein L is a covalent bond.

12. The pharmaceutical composition of claim 6, wherein:
R8 is a -L-heterocyclyl, wherein said heterocyclyl is pyridyl, thiazolyl, thiophenyl, quinolinyl, indolyl, 2,3-dihydrobenzofuranyl, benzo[d][1,3]dioxolyl, 2,3-dihydrobenzo[b][1,4]dioxinyl, 3,4-dihydro-2H-benzo[b][1,4]dioxepinyl, or chromanyl, wherein the ring or ring system of said -L-heterocyclyl has from 0-3 substituents and wherein said 0-3 substituents are selected from the group consisting of halo, alkyl, alkoxy, haloalkyl, haloalkoxy, amino, cyano, and hydroxyl, wherein the alkyl group in said alkyl, alkoxy, haloalkyl, or haloalkoxy has from 1 to 4 carbon atoms; or
R8 is -L-phenyl wherein the phenyl ring of said -L-phenyl has from 1-3 substituents and wherein said 1-3 substituents are selected from the group consisting of halo, alkyl, alkoxy, haloalkyl, haloalkoxy, amino, cyano, and hydroxyl, wherein the alkyl group in said alkyl, alkoxy, haloalkyl, or haloalkoxy has from 1 to 4 carbon atoms.

13. The pharmaceutical composition of claim 12, wherein L is a covalent bond.

14. The compound of claim 1, wherein L is a covalent bond.

15. The compound of claim 1, wherein each of R1-R5 is —H.

16. The compound of claim 1, wherein R8 is an -L-heterocyclyl, wherein said heterocyclyl is pyridyl, thiazolyl, thiophenyl, quinolinyl, or indolyl, wherein the ring or ring system of said -L-heterocyclyl has from 1-3 substituents and wherein said 1-3 substituents are selected from the group consisting of halo, alkyl, alkoxy, haloalkyl, haloalkoxy, amino, cyano, and hydroxyl, wherein the alkyl group in said alkyl, alkoxy, haloalkyl, or haloalkoxy has from 1 to 4 carbon atoms.

17. The compound of claim 2, wherein;
L is a covalent bond;
the substituents on the cyclopropyl ring have the trans configuration.

18. The pharmaceutical composition of claim 6, wherein L is a covalent bond.

19. The pharmaceutical composition of claim 6, wherein each of R1-R5 is —H.

20. The pharmaceutical composition of claim 6, wherein R8 is an -L-heterocyclyl, wherein said heterocyclyl is pyridyl, thiazolyl, thiophenyl, quinolinyl, or indolyl, wherein the ring or ring system of said -L-heterocyclyl has from 0-3 substituents and wherein said 0-3 substituents are selected from the group consisting of halo, alkyl, alkoxy, haloalkyl, haloalkoxy, amino, cyano, and hydroxyl, wherein the alkyl group in said alkyl, alkoxy, haloalkyl, or haloalkoxy has from 1 to 4 carbon atoms.

21. The pharmaceutical composition of claim 7, wherein:
L is a covalent bond;
and
the substituents on the cyclopropyl ring have the trans configuration.

22. The pharmaceutical composition of claim 6 wherein said compound is selected from the group consisting of:
(trans)-N-(4-fluorobenzyl)-2-phenylcyclopropanamine;
(trans)-N-(4-fluorobenzyl)-2-phenylcyclopropanaminium;
4-(((trans)-2-phenylcyclopropylamino)methyl)benzonitrile;
(trans)-N-(4-cyanobenzyl)-2-phenylcyclopropanaminium;
(trans)-2-phenyl-N-(4-(trifluoromethyl)benzyl)cyclopropanamine;
(trans)-2-phenyl-N-(4-(trifluoromethyl)benzyl)cyclopropanaminium:
(trans)-N-((6-methylpyridin-2-yl)methyl)-2-phenylcyclopropanamine;
(trans)-N-((3-bromothiophen-2-yl)methyl)-2-phenylcyclopropanamine;
(trans)-N-((4-bromothiophen-2-yl)methyl)-2-phenylcyclopropanamine;
(trans)-N-(3,4-dichlorobenzyl)-2-phenylcyclopropanamine;
(trans)-N-(3-fluorobenzyl)-2-phenylcyclopropanaminium;
(trans)-N-(2-fluorobenzyl)-2-phenylcyclopropanamine;
(trans)-N-(3-methoxybenzyl)-2-phenylcyclopropanamine;
(trans)-2-phenyl-N-((6-(trifluoromethyl)pyridin-3-yl)methyl)cyclopropanamine;
(trans)-N-((6-chloropyridin-3-yl)methyl)-2-phenylcyclopropanamine;
(trans)-N-((4-methylpyridin-2-yl)methyl)-2-phenylcyclopropanamine;
(trans)-N-((6-methoxypyridin-2-yl)methyl)-2-phenylcyclopropanamine;
2-(((trans)-2-phenylcyclopropylamino)methyl)pyridin-3-ol;
(trans)-N-((6-bromopyridin-2-yl)methyl)-2-phenylcyclopropanamine;
(trans)-2-phenyl-N-((5-(trifluoromethyl)pyridin-2-yl)methyl)cyclopropanamine;
(trans)-N-((3-fluoropyridin-2-yl)methyl)-2-phenylcyclopropanamine;
(trans)-N-((6-methoxypyridin-3-yl)methyl)-2-phenylcyclopropanamine;
(trans)-N-((5-methoxypyridin-3-yl)methyl)-2-phenylcyclopropanamine;
(trans)-N-((2-methoxypyridin-3-yl)methyl)-2-phenylcyclopropanamine;
3-(((trans)-2-phenylcyclopropylamino)methyl)benzonitrile;
(trans)-N-(2-methoxybenzyl)-2-phenylcyclopropanamine;
3-(((trans)-2-phenylcyclopropylamino)methyl)pyridin-2-amine;
(trans)-N-((2-chloropyridin-3-yl)methyl)-2-phenylcyclopropanamine;
(trans)-N-(3,4-dimethoxybenzyl)-2-phenylcyclopropanamine;
(trans)-N-(2,6-difluoro-4-methoxybenzyl)-2-phenylcyclopropanamine;
(trans)-2-phenyl-N-(4-(trifluoromethoxy)benzyl)cyclopropanamine;
(trans)-N-(5-fluoro-2-methoxybenzyl)-2-phenylcyclopropanamine;
(trans)-N-(2-fluoro-4-methoxybenzyl)-2-phenylcyclopropanamine;
(trans)-N-((4-methoxynaphthalen-1-yl)methyl)-2-phenylcyclopropanamine;
(trans)-N-(2-fluoro-6-methoxybenzyl)-2-phenylcyclopropanamine;
(trans)-N-((2-methoxynaphthalen-1-yl)methyl)-2-phenylcyclopropanamine;
(trans)-N-(4,7-dimethoxynaphthalen-1-yl)methyl)-2-phenylcyclopropanamine;
(trans)-N-(4-methoxy-3-methylbenzyl)-2-phenylcyclopropanamine;
(trans)-N-(3-chloro-4-methoxybenzyl)-2-phenylcyclopropanamine;
(trans)-N-(3-fluoro-4-methoxybenzyl)-2-phenylcyclopropanamine;
(trans)-N-(4-methoxy-2-methylbenzyl)-2-phenylcyclopropanamine;
(trans)-N-((2,2-dimethylchroman-6-yl)methyl)-2-phenylcyclopropanamine;
(trans)-N-(4-methoxy-2,3-dimethylbenzyl)-2-phenylcyclopropanamine;
(trans)-N-(4-methoxy-2,5-dimethylbenzyl)-2-phenylcyclopropanamine;
(trans)-N-(2-fluoro-4,5-dimethoxybenzyl)-2-phenylcyclopropanamine;
(trans)-N-(3-chloro-4,5-dimethoxybenzyl)-2-phenylcyclopropanamine;
(trans)-N-(2-chloro-3,4-dimethoxybenzyl)-2-phenylcyclopropanamine;
(trans)-N-(2,4-dimethoxy-6-methylbenzyl)-2-phenylcyclopropanamine;
(trans)-N-(2,5-dimethoxybenzyl)-2-phenylcyclopropanamine;
(trans)-N-(2,3-dimethoxybenzyl)-2-phenylcyclopropanamine;
(trans)-N-(2-chloro-3-methoxybenzyl)-2-phenylcyclopropanamine;
(trans)-2-phenyl-N-(pyridin-2-ylmethyl)cyclopropanamine;
(trans)-2-phenyl-N-(pyridin-3-ylmethyl)cyclopropanamine;
(trans)-2-phenyl-N-(pyridin-4-ylmethyl)cyclopropanamine;
(trans)-2-phenyl-N-(thiazol-2-ylmethyl)cyclopropanamine;
(trans)-2-phenyl-N-(thiophen-2-ylmethyl)cyclopropanamine;
(trans)-2-phenyl-N-(quinolin-4-ylmethyl)cyclopropanamine;
(trans)-2-phenyl-N-(quinolin-2-ylmethyl)cyclopropanamine;
(trans)-2-phenyl-N-(quinolin-3-ylmethyl)cyclopropanamine;
(trans)-N-((3H-indol-3-yl)methyl)-2-phenylcyclopropanamine;
(trans)-N-((2,3-dihydrobenzofuran-5-yl)methyl)-2-phenylcyclopropanamine;
(trans)-N-(benzo[d][1,3]dioxol-5-ylmethyl)-2-phenylcyclopropanamine;
(trans)-N-((2,3-dihydrobenzo[b][1,4]dioxin-6-yl)methyl)-2-phenylcyclopropanamine;
(trans)-N-((3,4-dihydro-2H-benzo[b][1,4]dioxepin-6-yl)methyl)-2-phenylcyclopropanamine;

(trans)-N-((3,4-dihydro-2H-benzo[b][1,4]dioxepin-7-yl)
methyl)-2-phenylcyclopropanamine;
(trans)-N-((1H-indol-5-yl)methyl)-2-phenylcyclopropan-
amine; and
pharmaceutically acceptable salts of any thereof.

23. A compound of formula I,

FORMULA I

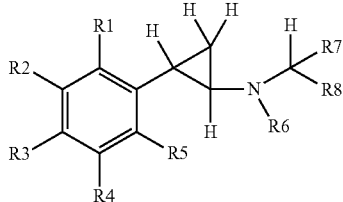

wherein:
each of R1-R5 is independently selected from the group
consisting of —H, halo, alkyl, alkoxy, haloalkyl, and
haloalkoxy, wherein the alkyl group in said alkyl,
alkoxy, haloalkyl, or haloalkoxy has from 1 to 4 carbon
atoms;
R6 is —H;
R7 is —H;
R8 is a -L-heterocyclyl, wherein said heterocyclyl is
pyridyl, thiazolyl, thiophenyl, quinolinyl, indolyl, 2,3-
dihydrobenzofuranyl, benzo[d][1,3]dioxolyl, 2,3-dihy-
drobenzo[b][1,4]dioxinyl, 3,4-dihydro-2H-benzo[b][1,
4]dioxepinyl, or chromanyl, wherein the ring or ring
system of said -L-heterocyclyl has from 0-3 substituents
and wherein said 0-3 substituents are selected from the
group consisting of halo, alkyl, alkoxy, haloalkyl,
haloalkoxy, amino, cyano, and hydroxyl, wherein the
alkyl group in said alkyl, alkoxy, haloalkyl, or
haloalkoxy has from 1 to 4 carbon atoms; or
R8 is -L-aryl, wherein said aryl is phenyl or naphthalenyl,
wherein the ring or ring system of said -L-aryl has from
1-3 substituents and wherein said 1-3 substituents are
selected from the group consisting of halo, alkyl, alkoxy,
haloalkyl, haloalkoxy, amino, cyano, and hydroxyl,
wherein the alkyl group in said alkyl, alkoxy, haloalkyl,
or haloalkoxy has from 1 to 4 carbon atoms;
L is a covalent bond or —CH$_2$;
or a pharmaceutically acceptable salt thereof;
with the provision that when L is a bond and R1, R2, R3,
R4, R5, R6, and R7 are all hydro, then R8 is not 2,4-
dimethoxyphenyl, 4-bromophenyl, 4-methoxyphenyl,
4-chlorophenyl, or furan-2-yl.

24. The compound of claim 23, wherein L is a covalent bond.

25. The compound of claim 23, wherein each of R1-R5 is —H.

26. The compound of claim 23, wherein R8 is a -L-hetero-
cyclyl, wherein said heterocyclyl is pyridyl, thiazolyl,
thiophenyl, quinolinyl, indolyl, 2,3-dihydrobenzofuranyl,
benzo[d][1,3]dioxolyl, 2,3-dihydrobenzo[b][1,4]dioxinyl,
3,4-dihydro-2H-benzo[b][1,4]dioxepinyl, or chromanyl,
wherein the ring or ring system of said -L-heterocyclyl has
from 0-3 substituents and wherein said 0-3 substituents are
selected from the group consisting of halo, alkyl, alkoxy,
haloalkyl, haloalkoxy, amino, cyano, and hydroxyl, wherein
the alkyl group in said alkyl, alkoxy, haloalkyl, or haloalkoxy
has from 1 to 4 carbon atoms.

27. The compound of claim 26, wherein R8 is a -L-hetero-
cyclyl, wherein said heterocyclyl is pyridyl, thiazolyl,
thiophenyl, quinolinyl, or indolyl, wherein the ring or ring
system of said -L-heterocyclyl has from 0-3 substituents and
wherein said 0-3 substituents are selected from the group
consisting of halo, alkyl, alkoxy, haloalkyl, haloalkoxy,
amino, cyano, and hydroxyl, wherein the alkyl group in said
alkyl alkoxy, haloalkyl, or haloalkoxy has from 1 to 4 carbon
atoms.

28. The compound of claim 23, wherein the substituents on
the cyclopropyl ring have the trans configuration.

29. The compound of claim 26, wherein:
L is a covalent bond;
the substituents on the cyclopropyl ring have the trans configuration.

30. The compound of claim 23 wherein said compound is selected from the group consisting of:
(trans)-N-(4-fluorobenzyl)-2-phenylcyclopropanamine;
(trans)-N-(4-fluorobenzyl)-2-phenylcyclopropan-
aminium;
4-(((trans)-2-phenylcyclopropylamino)methyl)benzoni-
trile;
(trans)-N-(4-cyanobenzyl)-2-phenylcyclopropan-
aminium;
(trans)-2-phenyl-N-(4-(trifluoromethyl)benzyl)cyclopro-
panamine;
(trans)-2-phenyl-N-(4-(trifluoromethyl)benzyl)cyclopro-
panaminium;
(trans)-N-((6-methylpyridin-2-yl)methyl)-2-phenylcyclo-
propanamine;
(trans)-N-((3-bromothiophen-2-yl)methyl)-2-phenylcy-
clopropanamine;
(trans)-N-((4-bromothiophen-2-yl)methyl)-2-phenylcy-
clopropanamine;
(trans)-N-(3,4-dichlorobenzyl)-2-phenylcyclopropan-
amine;
(trans)-N-(3-fluorobenzyl)-2-phenylcyclopropan-
aminium;
(trans)-N-(2-fluorobenzyl)-2-phenylcyclopropanamine;
(trans)-N-(3-methoxybenzyl)-2-phenylcyclopropan-
amine;
(trans)-2-phenyl-N-((6-(trifluoromethyl)pyridin-3-yl)me-
thyl)cyclopropanamine;
(trans)-N-((6-chloropyridin-3-yl)methyl)-2-phenylcyclo-
propanamine;
(trans)-N-((4-methylpyridin-2-yl)methyl)-2-phenylcyclo-
propanamine;
(trans)-N-((6-methoxypyridin-2-yl)methyl)-2-phenylcy-
clopropanamine;
2-(((trans)-2-phenylcyclopropylamino)methyl)pyridin-3-
ol;
(trans)-N-((6-bromopyridin-2-yl)methyl)-2-phenylcyclo-
propanamine;
(trans)-2-phenyl-N-((5-(trifluoromethyl)pyridin-2-yl)me-
thyl)cyclopropanamine;
(trans)-N-((3-fluoropyridin-2-yl)methyl)-2-phenylcyclo-
propanamine;
(trans)-N-((6-methoxypyridin-3-yl)methyl)-2-phenylcy-
clopropanamine;
(trans)-N-((5-methoxypyridin-3-yl)methyl)-2-phenylcy-
clopropanamine;
(trans)-N4(2-methoxypyridin-3-yl)methyl)-2-phenylcy-
clopropanamine;
3-(((trans)-2-phenylcyclopropylamino)methyl)benzoni-
trile;
(trans)-N-(2-methoxybenzyl)-2-phenylcyclopropan-
amine;
3-(((trans)-2-phenylcyclopropylamino)methyl)pyridin-2-
amine;

(trans)-N-((2-chloropyridin-3-yl)methyl)-2-phenylcyclopropanamine;
(trans)-N-(3,4-dimethoxybenzyl)-2-phenylcyclopropanamine;
(trans)-N-(2,6-difluoro-4-methoxybenzyl)-2-phenylcyclopropanamine;
(trans)-2-phenyl-N-(4-(trifluoromethoxy)benzyl)cyclopropanamine;
(trans)-N-(5-fluoro-2-methoxybenzyl)-2-phenylcyclopropanamine;
(trans)-N-(2-fluoro-4-methoxybenzyl)-2-phenylcyclopropanamine;
(trans)-N-((4-methoxynaphthalen-1-yl)methyl)-2-phenylcyclopropanamine;
(trans)-N-(2-fluoro-6-methoxybenzyl)-2-phenylcyclopropanamine;
(trans)-N-((2-methoxynaphthalen-1-yl)methyl)-2-phenylcyclopropanamine;
(trans)-N-((4,7-dimethoxynaphthalen-1-yl)methyl)-2-phenylcyclopropanamine;
(trans)-N-(4-methoxy-3-methylbenzyl)-2-phenylcyclopropanamine;
(trans)-N-(3-chloro-4-methoxybenzyl)-2-phenylcyclopropanamine;
(trans)-N-(3-fluoro-4-methoxybenzyl)-2-phenylcyclopropanamine;
(trans)-N-(4-methoxy-2-methylbenzyl)-2-phenylcyclopropanamine;
(trans)-N-((2,2-dimethylchroman-6-yl)methyl)-2-phenylcyclopropanamine;
(trans)-N-(4-methoxy-2,3-dimethylbenzyl)-2-phenylcyclopropanamine;
(trans)-N-(4-methoxy-2,5-dimethylbenzyl)-2-phenylcyclopropanamine;
(trans)-N-(2-fluoro-4,5-dimethoxybenzyl)-2-phenylcyclopropanamine;
(trans)-N-(3-chloro-4,5-dimethoxybenzyl)-2-phenylcyclopropanamine;
(trans)-N-(2-chloro-3,4-dimethoxybenzyl)-2-phenylcyclopropanamine;
(trans)-N-(2,4-dimethoxy-6-methylbenzyl)-2-phenylcyclopropanamine;
(trans)-N-(2,5-dimethoxybenzyl)-2-phenylcyclopropanamine;
(trans)-N-(2,3-dimethoxybenzyl)-2-phenylcyclopropanamine;
(trans)-N-(2-chloro-3-methoxybenzyl)-2-phenylcyclopropanamine:
(trans)-2-phenyl-N-(pyridin-2-ylmethyl)cyclopropanamine;
(trans)-2-phenyl-N-(pyridin-3-ylmethyl)cyclopropanamine;
(trans)-2-phenyl-N-(pyridin-4-ylmethyl)cyclopropanamine;
(trans)-2-phenyl-N-(thiazol-2-ylmethyl)cyclopropanamine;
(trans)-2-phenyl-N-(thiophen-2-ylmethyl)cyclopropanamine;
(trans)-2-phenyl-N-(quinolin-4-ylmethyl)cyclopropanamine;
(trans)-2-phenyl-N-(quinolin-2-ylmethyl)cyclopropanamine;
(trans)-2-phenyl-N-(quinolin-3-ylmethyl)cyclopropanamine;
(trans)-N-((3H-indol-3-yl)methyl)-2-phenylcyclopropanamine;
(trans)-N-((2,3-dihydrobenzofuran-5-yl)methyl)-2-phenylcyclopropanamine;
(trans)-N-(benzo[d][1,3]dioxol-5-ylmethyl)-2-phenylcyclopropanamine;
(trans)-N-((2,3-dihydrobenzo[b][1,4]dioxin-6-yl)methyl)-2-phenylcyclopropanamine;
(trans)-N-((3,4-dihydro-2H-benzo[b][1,4]dioxepin-6-yl)methyl)-2-phenylcyclopropanamine;
(trans)-N-((3,4-dihydro-2H-benzo[b][1,4]dioxepin-7-yl)methyl)-2-phenylcyclopropanamine;
(trans)-N-((1H-indol-5-yl)methyl)-2-phenylcyclopropanamine; and
pharmaceutically acceptable salts of any thereof.

\* \* \* \* \*